US012767728B2

(12) United States Patent
Lamberth et al.

(10) Patent No.: US 12,767,728 B2
(45) Date of Patent: Oct. 20, 2026

(54) BISPECIFIC FACTOR VIII MIMETIC ANTIBODIES

(71) Applicant: Novo Nordisk A/S, Bagsvaerd (DK)

(72) Inventors: Kasper Lamberth, Stenloese (DK); Jacob Lund, Roskilde (DK); Gustav Roeder, Frederikssund (DK); Bjarne Gram Hansen, Alleroed (DK); Per J. Greisen, Sammamish, WA (US); Nikolai Lorenzen, Broenshoej (DK)

(73) Assignee: Novo Nordisk A/S, Bagsvaerd (DK)

( * ) Notice: Subject to any disclaimer, the term of this patent is extended or adjusted under 35 U.S.C. 154(b) by 1116 days.

(21) Appl. No.: 17/795,269

(22) PCT Filed: Jan. 29, 2021

(86) PCT No.: PCT/EP2021/052070
§ 371 (c)(1),
(2) Date: Jul. 26, 2022

(87) PCT Pub. No.: WO2021/152066
PCT Pub. Date: Aug. 5, 2021

(65) Prior Publication Data

US 2025/0376538 A1 Dec. 11, 2025

(30) Foreign Application Priority Data

Jan. 30, 2020 (EP) .................................... 20154607

(51) Int. Cl.
*C07K 16/36* (2006.01)

(52) U.S. Cl.
CPC .......... *C07K 16/36* (2013.01); *C07K 2317/31* (2013.01); *C07K 2317/33* (2013.01); *C07K 2317/75* (2013.01)

(58) Field of Classification Search
None
See application file for complete search history.

(56) References Cited

U.S. PATENT DOCUMENTS

| | | | | |
|---|---|---|---|---|
| 6,180,370 | B1 * | 1/2001 | Queen | A61P 19/02 435/69.6 |
| 9,334,331 | B2 | 5/2016 | Igawa et al. | |
| 10,759,870 | B2 | 9/2020 | Teranishi et al. | |
| 12,545,743 | B2 * | 2/2026 | Igawa | C07K 16/36 |
| 2018/0000228 | A1 | 1/2018 | Ewert et al. | |
| 2018/0022825 | A1 | 1/2018 | Ewert et al. | |

FOREIGN PATENT DOCUMENTS

| | | | | |
|---|---|---|---|---|
| EP | 1220923 | A2 | 7/2002 | |
| EP | 1660536 | A2 | 5/2006 | |
| WO | 2005025615 | | 3/2005 | |
| WO | 2012067176 | A1 | 5/2012 | |
| WO | 2018098363 | | 5/2018 | |
| WO | WO-2018141863 | A1 * | 8/2018 | A61P 7/04 |
| WO | 2019065795 | | 4/2019 | |
| WO | 2020025672 | A1 | 2/2020 | |

OTHER PUBLICATIONS

Janeway, Charles A. "Immunobiology: The Immune System in Health and Disease." 2001 (Year: 2001).*
Kipriyanov, Sergey M., and Fabrice Le Gall. "Generation and production of engineered antibodies." Molecular biotechnology 26.1 (2004): 39-60.(Year: 2004).*
Hou et al., "Research Progress on Structural modification of recombinant factor VIII and its antibody mimetics", Progress in Pharmacy, Oct. 2019, No. 10, pp. 749-758.
NCBI GenBank: AAZ08810.1, "immunoglobulin heavy chain variable region, partial [*Homo sapiens*]", Jul. 26, 2016, 2 pages.
Avery et al., "Establishing in vitro in vivo correlations to screen monoclonal antibodies for physicochemical properties related to favorable human pharmacokinetics", MAbs, Jan. 29, 2018, vol. 10, No. 2, pp. 244-255.
Blair, "Emicizumab: A Review in Haemophilia A" Drugs, Sep. 2019, vol. 79, No. 15, pp. 1697-1707.
Dobson et al., "Engineering the surface properties of a human monoclonal antibody prevents self-association and rapid clearance in vivo", Nature, Dec. 20, 2016, vol. 6, Article No. 38644, pp. 1-14.
Finlay et al., "Anti-PD1 'SHR-1210' aberrantly targets pro-angiogenic receptors and this polyspecificity can be ablated by paratope refinement", MAbs, Dec. 2018, vol. 11, No. 1, pp. 26-44.
Kitazawa et al., "Factor VIIIa-mimetic cofactor activity of a bispecific antibody to factors IX/IXa and X/Xa, emicizumab, depends on its ability to bridge the antigens", Thrombosis and Haemostasis, Jul. 2017, vol. 117, No. 07, pp. 1348-1357.
Kolkman et al., "Insertion Loop 256?268 in Coagulation Factor IX Restricts Enzymatic Activity in the Absence but Not In the Presence of Factor VIII", Biochemistry, May 31, 2000, vol. 39, pp. 7398-7405.
Pilunni et al., "When innovation goes fast. The case of hemophilia", Current Opinion in Pharmacology, Apr. 2019, vol. 45, pp. 95-101.
Sampei et al., "Identification and Multidimensional Optimization of an Asymmetric Bispecific IgG Antibody Mimicking the Function of Factor VIII Cofactor Activity", PLOS ONE, Feb. 28, 2013, vol. 8, No. 2, e57479, pp. 1-13.
Scheiflinger et al., "Enhancement of the enzymatic activity of activated coagulation factor IX by anti-factor IX antibodies", J Thromb Haemost, Feb. 2008, vol. 6. pp. 315-322.

(Continued)

*Primary Examiner* — Misook Yu
*Assistant Examiner* — Lia E Taylor
(74) *Attorney, Agent, or Firm* — Jianjie Hu

(57) ABSTRACT

The present invention relates to bispecific antibodies capable of binding to coagulation Factor IX (FIX) and/or the activated form thereof Factor IXa (FIXa), and Factor X (FX) and/or the activated form thereof Factor Xa (FXa) and promoting FX activation by FIXa and methods and composition for treating subjects suffering from a coagulopathy such as haemophilia A with or without inhibitors.

21 Claims, 1 Drawing Sheet

Specification includes a Sequence Listing.

(56) References Cited

OTHER PUBLICATIONS

Shima et al., "Factor VIII-Mimetic Function of Humanized Bispecific Antibody in Hemophilia A", N Engl J Med, May 26, 2016, vol. 374, pp. 2044-2053.
Zogg et al., "Activation mechanisms of coagulation factor IX", Biol Chem, May 2009, vol. 390, No. 5-6, pp. 391-400.
Rudikoff, et al., "Single amino acid substitution altering antigen-binding specificity", Proceedings of the National Academy of Sciences, USA, Mar. 1982, vol. 79, No. 6, pp. 1979-1983.
Winkler et al., "Changing the antigen binding specificity by single point mutations of an anti-p24 (HIV-1) antibody", The Journal of Immunology, Oct. 2000, vol. 165, No. 8, pp. 4505-4514.

* cited by examiner

Sequence alignment of variable domains (CDR1, 2 and 3 highlighted)

Figure 1A Alignment of heavy chain variable domain (VH) sequence of anti-FIX(a) antibodies with CDR sequences shown underlined and in bold for the uppermost sequence

| | |
|---|---|
| SEQ ID NO. 25 mAb1_FIX_VH | EVQLVESGGGLVQPGRSLRLSCAASGFTFH**DYAMH**WVRQVPGKGLEWVS**GISWRGDIGGYVKSVKG**RFTISRDNAKNSLYLQMNSLRAEDTALYYCVK**SYGSGSFYNAFDS**WGQGTLVTVSS |
| SEQ ID NO. 33 mAb2_FIX_VH | EVQLVESGGGLVQPGRSLRLSCAASGFTFHDYAMHWVRQVPGKGLEWVSGISWRGDIGGYVKSVKGRFTISRDNAKNSLYLQMNSLRAEDTALYYCVKSYGSGSFYNAFDSWGQGTLVTVSS |
| SEQ ID NO. 41 mAb3_FIX_VH | EVQLVESGGGLVQPGRSLRLSCAASGFTFHDYAMHWVRQVPGKGLEWVSGISWRGDIGGYVKSVKGRFTISRDNAKNSLYLQMNSLRAEDTALYYCVKSYGSGSFYNAFDSWGQGTLVTVSS |
| SEQ ID NO. 49 mAb4_FIX_VH | EVQLVESGGGLVQPGRSLRLSCAASGFTFHDYAMHWVRQVPGKGLEWVSGISWRGDIGGYVKSVKGRFTISRDNAKNSLYLQMNSLRAEDTALYYCVKSYGSGSFYNAFDSWGQGTLVTVSS |
| SEQ ID NO. 57 mAb5_FIX_VH | EVQLVESGGGLVQPGRSLRLSCAASGFTFHDYAMHWVRQVPGKGLEWVSGISWRGDIGGYVKSVKGRFTISRDNAKNSLYLQMNSLRAEDTALYYCVKSYGSGSFYNAFDSWGQGTLVTVSS |
| SEQ ID NO. 65 mAb6_FIX_VH | EVQLVESGGGLVQPGRSLRLSCAASGFTFHDYAMHWVRQVPGKGLEWVSGISWRGDIGGYVKSVKGRFTISRDNAKNSLYLQMNSLRAEDTALYYCVKSYGSGSFYNAFDSWGQGTLVTVSS |
| SEQ ID NO. 73 mAb7_FIX_VH | EVQLVESGGGLVQPGRSLRLSCAASGFTFHDYAMHWVRQVPGKGLEWVSGISWRGDIGGYVKSVKGRFTISRDNAKNSLYLQMNSLRAEDTALYYCVKSYGSGSFYNAFDSWGQGTLVTVSS |
| SEQ ID NO. 81 mAb8_FIX_VH | EVQLVESGGGLVQPGRSLRLSCAASGFTFHDYAMHWVRQVPGKGLEWVSGISWRGDIGGYVKSVKGRFTISRDNAKNSLYLQMNSLRAEDTALYYCVKSYGSGSFYNAFDSWGQGTLVTVSS |

Figure 1B Alignment of light chain variable domain (VL) sequence of anti-FIX(a) antibodies with CDR sequences shown underlined and in bold for the uppermost sequence

| | |
|---|---|
| SEQ ID NO. 29 mAb1_FIX_VL | DIQMTQSPSTLSASVGDRVTITC**RASQSISSWLA**WYQQKPGKAPKFLIY**KGSKADR**GTPSRFSGSGSGTEFTLTISSLQPDDFATYYC**LEYESYIRT**FGQGTKVEIK |
| SEQ ID NO. 37 mAb2_FIX_VL | DIQMTQSPSTLSASVGDRVTITCRASQSISSWLAWYQQKPGKAPKFLIYKGSKQDRGTPSRFSGSGSGTEFTLTISSLQPDDFATYYCLEYSSYIRTFGQGTKVEIK |
| SEQ ID NO. 45 mAb3_FIX_VL | DIQMTQSPSTLSASVGDRVTITCRASQSISSWLAWYQQKPGKAPKFLIYKGSKTDRGTPSRFSGSGSGTEFTLTISSLQPDDFATYYCLEYESYIRTFGQGTKVEIK |
| SEQ ID NO. 53 mAb4_FIX_VL | DIQMTQSPSTLSASVGDRVTITCRASQSISSWLAWYQQKPGKAPKFLIYKSEKLDRGTPSRFSGSGSGTEFTLTISSLQPDDFATYYCLEYESYIRTFGQGTKVEIK |
| SEQ ID NO. 61 mAb5_FIX_VL | DIQMTQSPSTLSASVGDEVTITCRASQSISSWLAWYQQKPGKAPKFLIYKGEKLDRGTPSRFSGSGSGTEFTLTISSLQPDDFATYYCLEYSSYIRTFGQGTKVEIK |
| SEQ ID NO. 69 mAb6_FIX_VL | DIQMTQSPSTLSASVGDEVTITCRASQSISSWLAWYQQKPGKAPKFLIYKGSKLDRGTPSRFSGSGSGTEFTLTISSLQPDDFATYYCLEYSSYIRTFGQGTKVEIK |
| SEQ ID NO. 77 mAb7_FIX_VL | DIQMTQSPSTLSASVGDEVTITCRASQSISSWLAWYQQKPGKAPKFLIYKAEKLDRGTPSRFSGSGSGTEFTLTISSLQPDDFATYYCLEYESYIRTFGQGTKVEIK |
| SEQ ID NO. 85 mAb8_FIX_VL | DIQMTQSPSTLSASVGDRVTITCRASQSISSWLAWYQQKPGKAPKFLIYKAEKLDRGTPSRFSGSGSGTEFTLTISSLQPDDFATYYCLEYESYIRTFGQGTKVEIK |

Figure 1C Alignment of heavy chain variable domain (VH) sequence of anti-FX(a) antibodies with CDR sequences shown underlined and in bold for the uppermost sequence

| | |
|---|---|
| SEQ ID NO. 1 mAbA_FX_VH | EVQLVQSGAEVKKPGESLRISCKGSGYSFS**TSWIV**WVRQMPGKGLEWMG**MIDPSDSFTSYSPSFQG**HVTISADKSISTAYLQWSSLKASDTAMYYCAR**LHYYNSEEFDV**WGQGTLVTVSS |
| SEQ ID NO. 17 mAbB_FX_VH | EVQLVQSGAEVKKPGESLRISCKGSGYSFSTSWIVWVRQMPGKGLEWMGMIDPSDSYTSYSPSFQGHVTISADKSISTAYLQWSSLKASDTAMYYCARLHYYNSEEFDVWGQGTMVTVSS |

Figure 1D Alignment of light chain variable domain (VL) sequence of anti-FX(a) antibodies with CDR sequences shown underlined and in bold for the uppermost sequence

| | |
|---|---|
| SEQ ID NO. 5 mAbA_FX_VL | EIVLTQSPGTLSLSPGERATLSC**RASQSVSSSYLA**WYQQKPGQAPRLLIY**GQSSRTR**GIPDRFSGSGSGTDFTLTISRLEPEDFAVYYC**QQFGDSQLFT**FGQGTKLEIK |
| SEQ ID NO. 21 mAbB_FX_VL | EIVLTQSPGTLSLSPGERATLSCRASQSVSSSYLAWYQQKPGQAPRLLIYGQSSRTRGIPDRFSGSGSGTDFTLTISRLEPEDFAVYYCQQFGESQLFTFGQGTKLEIK |

BISPECIFIC FACTOR VIII MIMETIC ANTIBODIES

CROSS-REFERENCE TO RELATED APPLICATIONS

This application is a 35 U.S.C. § 371 National Stage application of International Application PCT/EP2021/052070 (WO 2021/152066), filed Jan. 29, 2021, which claims priority to European Patent Application 20154607.4, filed Jan. 30, 2020; the contents of which are incorporated herein by reference.

INCORPORATION BY REFERENCE OF THE SEQUENCE LISTING

The instant application contains a Sequence Listing which has been submitted in ASCII format via EFS-Web and is hereby incorporated by reference in its entirety. Said ASCII copy, created on Dec. 15, 2022, is named 190097US01_ST25.txt and is 53 kilobytes in size. The entire contents of the sequence listing are hereby incorporated by reference.

BACKGROUND

In patients with a coagulopathy, such as in human beings with haemophilia A and B, various steps of the coagulation cascade are rendered dysfunctional due to, for example, the absence or insufficient presence of a functional coagulation factor. Such dysfunction of one part of the coagulation cascade results in insufficient blood coagulation and potentially life-threatening bleeding, or damage to internal organs, such as the joints.

Coagulation Factor VIII (FVIII) deficiency, commonly referred to as haemophilia A, is a congenital bleeding disorder affecting approximately 420,000 people worldwide, of which around 105,000 are currently diagnosed.

Patients with haemophilia A may receive coagulation factor replacement therapy such as exogenous FVIII. Conventional treatment consists of replacement therapy, provided as prophylaxis or on demand treatment of bleeding episodes. Until recently prophylactic treatment for a patient with severe haemophilia A included up to three intravenous injections/week with either plasma derived FVIII or recombinant FVIII or long-acting variants thereof.

However, such patients are at risk of developing neutralizing antibodies, so-called inhibitors, to such exogenous factors, rendering formerly efficient therapy ineffective. Haemophilia A patients with inhibitors is a non-limiting example of a coagulopathy that is partly congenital and partly acquired. Patients that have developed inhibitors to FVIII cannot be treated with conventional replacement therapy. Exogenous coagulation factors may only be administered intravenously, which is of considerable inconvenience and discomfort to patients.

An inadequate FXa formation and decreased thrombin generation caused by reduced or absent FVIII activity is the reason underlying the bleeding diathesis in haemophilia A patients.

Proteolytic conversion of FX into its enzymatically active form FXa can be achieved by the intrinsic FX-activating complex comprising FIXa and its cofactor activated FVIII (FVIIIa). Cofactor binding increases the enzymatic activity of FIXa by about five orders of magnitude and is believed to result through multiple mechanisms as outlined by Scheiflinger et al. (2008) *J Thromb Haemost,* 6:315-322. Notably, FVIIIa has been found to stabilize a conformation of FIXa that has increased proteolytic activity towards FX (Kolkman J A, Mertens K (2000) *Biochemistry,* 39:7398-7405, Zogg T, Brandstetter H (2009) *Biol Chem,* 390:391-400). Based on this observation and realizing that antibodies are versatile binding proteins capable of mimicking a variety of protein-protein interactions, Scheiflinger et al. performed a screen for agonistic anti-FIX(a) antibodies characterized by an ability to enhance FX activation by FIXa in the presence of a phospholipid surface and calcium, but in the absence of the natural cofactor FVIIIa and from a screen of 5280 hybridoma supernatants, 88 were found to produce antibodies exhibiting various degrees of FIXa agonistic activity, cf. EP1220923 B1 and EP1660536 B1. Recently, a new drug, emicizumab (HEMLIBRA®) also known as ACE910, has been approved for subcutaneous prophylactic treatment of Haemophilia A with or without inhibitors against conventional replacement therapy factors. Emicizumab is a humanized, bispecific anti-FIX(a)/anti-FX(a) monoclonal antibody developed by Chugai Pharmaceuticals/Roche Pharmaceuticals for the treatment of haemophilia A. Emicizumab is designed to mimic FVIII cofactor function (see Sampei et al.: (2013) *PLOS One,* 8, e57479 and WO2012/067176). Treatment with 30-50 μg of emicizumab per milliliter plasma has been speculated correspond to at least 10 to 15 IU of equivalent factor VIII activity per decilitre plasma (Shima et al., N Engl J Med 2016; 374:2044-53). However, some patients have developed inhibitors (anti-drug antibodies) against emicizumab rendering treatment with this compound ineffective.

Besides the generation of inhibitors as exemplified for emicizumab, other antibody properties are also important for achieving an effective antibody-based treatment for the patient. In particular, it has been demonstrated how antibodies with high propensity for non-specific binding may lead to safety issues in the clinic. In some reports, a high level of non-specific binding caused a several-fold reduction in circulating half-life of the antibody and led to ineffective and cumbersome dosing regimens for the patient (See Dobson et al., *Nature*, volume 6, art. no.: 38644 (2016) and Avery et al., *MAbs* 2018, Vol. 10, No. 2, 244-255). WO2018/141863 and WO2019/065795 also disclose anti-FIX(a) anti-FX(a) bispecific antibodies and their use as procoagulants for the treatment of haemophilia.

There are still many unmet medical needs in the haemophilia community, in particular, in subjects with coagulopathies. The present invention relates to improved compounds capable of substituting for FVIII and thus being useful for the treatment of a coagulopathy such as haemophilia A.

SUMMARY

The present invention relates to compounds, which serve as a substitute for coagulation Factor VIII (FVIII) in patients suffering from a coagulopathy and in particular patients lacking functional FVIII, such as haemophilia A patients including haemophilia A patients with inhibitors.

One aspect of the present invention relates to compounds capable of enhancing the generation of FXa and thus partially or completely restoring coagulation in patients lacking functional FVIII.

In one aspect, the compound is an antibody or antigen-binding fragment thereof. In one such aspect, the compound is a multispecific antibody or antigen-binding fragment thereof such as a bispecific antibody or antigen-binding fragment thereof.

In one particular aspect, the invention relates to antibodies or antigen-binding fragment thereof which serve as a substitute for FVIII in patients lacking functional FVIII, such as haemophilia A patients.

In one such aspect, the antibody or antigen-binding fragment thereof is capable of binding FIX(a) and increases the enzymatic activity of FIXa towards FX, optionally also being capable of binding FX.

In one aspect, the invention relates to an antibody or antigen-binding fragment thereof that is capable of binding FIX(a) and FX(a), including bispecific antibodies or antigen-binding fragment thereof which increase the enzymatic activity of FIXa towards FX.

In one aspect, the invention relates to an antibody or antigen-binding fragment thereof that is capable of binding FIX(a) and FX(a), which has improved properties as compared to antibodies disclosed in the art. In one such aspect, said antibody or antigen-binding fragment thereof has improved procoagulant properties and/or decreased propensity for non-specific binding to e.g. DNA and/or insulin, and/or deceased propensity for self-association as compared to bispecific antibodies in the art including emicizumab.

A further aspect of the invention relates to the individual component (intermediate) antibodies or antigen-binding fragment thereof that are part of a bispecific antibody, such as a particular anti-FIX(a) antibody or antigen-binding fragment thereof or a particular anti-FX(a) antibody or antigen-binding fragment thereof.

A further aspect of the invention is directed to the antibodies or antigen-binding fragment thereof disclosed herein for prevention and/or treatment of a coagulopathy, a disease accompanying coagulopathy, or a disease caused by coagulopathy. In one aspect, the coagulopathy is haemophilia, such as haemophilia A with or without inhibitors.

A still further aspect of the invention relates to a pharmaceutical composition comprising an antibody or antigen-binding fragment thereof as disclosed herein formulated for the delivery of said antibody for the prevention and/or treatment of a coagulopathy, such as haemophilia A with or without inhibitors, as well as an injection device with content thereof.

A further aspect of the invention is directed to a kit comprising (i) an antibody or antigen-binding fragment thereof as disclosed herein such as a bispecific antibody and (ii) instructions for use.

The invention may also solve further problems that will be apparent from the disclosure of the exemplary embodiments.

BRIEF DESCRIPTION OF THE FIGURES

FIGS. 1A-D show aligments of sequences representing heavy- and light chain variable domains of the anti-FIX(a) (FIGS. 1A and 1B) and anti-FX(a) (FIGS. 1C and 1D) IgG antibodies as disclosed herein. CDR1, 2 and 3 sequences are highlighted in bold and underlined in uppermost sequence and is representative for the remaining sequences in the respective figures.

BRIEF DESCRIPTION OF THE SEQUENCES

SEQ ID NOs: 1-8 and 17-88 represent the sequences of the heavy chain variable domains (VH) and light chain variable domains (VL) and Complementarity Determining Regions (CDRs) of anti-FIX(a) and anti-FX(a) monoclonal antibodies (mAbs) described herein.

SEQ ID NO:89 represents the amino acid sequence of human coagulation Factor IX.

SEQ ID NO:90 represents the amino acid sequence of human coagulation Factor X.

SEQ ID NO:91 represents the human IgG4 heavy chain contant region with S228P and C-terminal lysine truncation.

SEQ ID NO:92 represents the human IgG4 heavy chain constant region with S228P, F405L, R409K and C-terminal lysine truncation.

SEQ ID NO:93 represents the human kappa light chain constant region.

SEQ ID NO:94 represents the human IgG1 heavy chain constant region with F405L and C-terminal lysine truncation.

SEQ ID NO:95 represents the human IgG1 heavy chain constant region with K409R and C-terminal lysine truncation.

SEQ ID NOs: 9-16 are omitted intentionally.

The tables in Example 6 link the SEQ ID NOs to individual (component) anti-FIX(a) and anti-FX(a) antibodies and bispecific antibodies of the invention.

DESCRIPTION

In subjects with a coagulopathy, such as in human beings with haemophilia A, the coagulation cascade is rendered dysfunctional due to the absence or insufficient presence of functional FVIII. Such dysfunction of one part of the coagulation cascade results in insufficient blood coagulation and potentially life-threatening bleeding, or damage to internal organs, such as the joints. The present invention relates to compounds, which serve as a substitute for coagulation Factor VIII (FVIII) in patients suffering from a coagulopathy and in particular patients lacking functional FVIII, such as haemophilia A patients including haemophilia A patients with inhibitors. In one aspect, such compound is an antibody.

In particular the inventors of the present invention have surprisingly identified antibodies which mimic FVIII cofactor activity with high potency and efficacy. In one particular aspect, the invention relates to antibodies which serve as a substitute for FVIII in patients lacking functional FVIII, such as haemophilia A patients. In one such aspect, the antibodies bind to and increase the enzymatic activity of coagulation Factor IXa (FIXa) towards coagulation Factor X (FX), optionally also binding FX. In one such aspect the antibodies of the invention are bispecific antibodies capable of binding to FIX/FIXa and FX.

A further aspect of the invention relates to the individual component (intermediate) antibodies or antigen-binding fragment thereof that are part of a multispecific antibody, such as a particular anti-FIX(a) antibody or antigen-binding fragment thereof or a particular anti-FX(a) antibody or antigen-binding fragment thereof.

A further aspect of the invention relates to the manufacture of the antibodies or antigen-binding fragment thereof—and components (intermediates) thereof—as disclosed herein.

A further aspect of the invention relates to an antibody that competes with an antibody or antigen-binding fragment thereof, as disclosed herein, for binding to FIX(a) and/or FX(a).

A further aspect of the invention relates to an antibody or antigen-binding fragment thereof which shares epitope residues on FIX(a) and/or FX(a) with an antibody or antigen-binding fragment hereof, as disclosed herein.

In one aspect, the antibody is a human or humanised antibody, such as a human or humanised bispecific antibody.

A further aspect of the invention is directed to the antibodies or antigen-binding fragment thereof disclosed herein for prevention and/or treatment of a coagulopathy, a disease accompanying coagulopathy, or a disease caused by coagulopathy. In one aspect the coagulopathy is haemophilia A with or without inhibitors.

A still further aspect of the invention relates to a pharmaceutical composition comprising a antibody or antigen-binding fragment thereof as disclosed herein formulated for the delivery of said antibody for the prevention and/or treatment of a coagulopathy, such as haemophilia A with or without inhibitors, as well as an injection device with content thereof.

A further aspect of the invention is directed to a kit comprising (i) an antibody or antigen-binding fragment thereof as disclosed herein such as a bispecific antibody and (ii) instructions for use.

Coagulation Factor IX

Coagulation Factor IX (FIX) is a vitamin K-dependent coagulation factor with structural similarities to Factor VII, prothrombin, Factor X, and Protein C. FIX circulates in plasma as a single-chain zymogen (SEQ ID NO:89). The circulating zymogen form consists of 415 amino acids divided into four distinct domains comprising an N-terminal γ-carboxyglutamic acid-rich (Gla) domain, two EGF domains and a C-terminal trypsin-like serine protease domain.

Activation of FIX occurs by limited proteolysis at Arg145 and Arg180 to release the activation peptide (residues 146 to 180 of SEQ ID NO:89). Thus, activated FIX (FIXa) is composed of residues 1-145 of SEQ ID NO:89 (light chain) and residues 181-415 of SEQ ID NO:89 (heavy chain).

Circulating FIX molecules thus comprise the FIX zymogen and the activated form of FIX which are herein generally referred to as FIX and FIXa with reference to SEQ ID NO:1.

Activated Factor IX is referred to as Factor IXa or FIXa. The term "FIX (SEQ ID NO:1) and/or the activated form thereof (FIXa)" may also be referred to as "FIX/FIXa" or simply "FIX(a)". FIXa is a trypsin-like serine protease that serves a key role in haemostasis by generating, as part of the tenase complex, most of the Factor Xa required to support proper thrombin formation during coagulation.

FIX is herein represented by SEQ ID NO:1 corresponding to the Ala148 allelic form of human FIX (Anson et al. EMBO J. 1984 3:1053-1060; McGraw et al., Proc Natl Acad Sci USA. 1985 82:2847-2851; Graham et al. *Am. J. Hum. Genet.* 1988 42:573-580). In the present invention FIX is intended to cover all natural variants of FIX, such as the T148 variant (Uniprot ID P00740).

Coagulation Factor X

FX is a vitamin K-dependent coagulation factor with structural similarities to Factor VII, prothrombin, FIX, and protein C. FX circulates in plasma as a two-chain zymogen including residues 1-139 of SEQ ID NO:2 (light chain) and residues 143-448 of SEQ ID NO:2 (heavy chain). Human FX zymogen comprises four distinct domains comprising an N-terminal gamma-carboxyglutamic acid rich (Gla) domain (residues 1-45), two EGF domains, EGF1 (residues 46-82) and EGF2 (residues 85-125), respectively, and a C-terminal trypsin-like serine protease domain (residues 195-448). Activation of FX occurs by limited proteolysis at Arg194, which results in the release of the activation peptide (residues 143-194). Thus, activated FX (FXa) is composed of residues 1-139 of SEQ ID NO:2 (light chain) and residues 195-448 of SEQ ID NO:2 (activated heavy chain). Circulating Factor X molecules thus comprises the FX zymogen and the activated form of FX which are herein referred to as FX and FXa, respectively, with reference to SEQ ID NO:2. In the present invention FX is intended to cover all natural variants of FX. The term "FX (SEQ ID NO:90) and/or the activated form thereof (FXa)" may also be referred to as "FX/FXa" or "FX(a)".

Antibodies

The term "antibody" herein refers to a protein, derived from an immunoglobulin sequence, which is capable of binding to an antigen or a portion thereof. The term antibody includes, but is not limited to, full length antibodies of any class (or isotype), that is, IgA, IgD, IgE, IgG, IgM and/or IgY. The term antibody includes—but is not limited to—antibodies that are bivalent, such as bispecific antibodies.

Natural full-length antibodies comprise at least four polypeptide chains: two heavy chains (HC) and two light chains (LC) that are connected by disulfide bonds. In some cases, natural antibodies comprise less than four chains, as in the case of the IgNARs found in Chondrichthyes. One class of immunoglobulins of particular pharmaceutical interest is the IgGs. In humans, the IgG class may be divided into four sub-classes IgG1, IgG2, IgG3 and IgG4, based on the sequence of their heavy chain constant regions. The light chains can be divided into two types, kappa and lambda chains, based on differences in their sequence composition. IgG molecules are composed of two heavy chains, interlinked by two or more disulfide bonds, and two light chains, each attached to a heavy chain by a disulfide bond. An IgG heavy chain may comprise a heavy chain variable domain ($V_H$) and up to three heavy chain constant ($C_H$) domains: $C_H1$, $C_H2$ and $C_H3$. A light chain may comprise a light chain variable domain ($V_L$) and a light chain constant domain ($C_L$). $V_H$ and $V_L$ regions can be further subdivided into regions of hypervariability, termed complementarity determining regions (CDRs) or hypervariable regions (HvRs), interspersed with regions that are more conserved, termed framework regions (FR). $V_H$ and $V_L$ domains are typically composed of three CDRs and four FRs, arranged from amino-terminus to carboxy-terminus in the following order: FR1, CDR1, FR2, CDR2, FR3, CDR3, FR4. The heavy and light chain variable domains containing the hypervariable regions (CDRs) form a structure that is capable of interacting with an antigen, whilst the constant region of an antibody may mediate binding of the immunoglobulin to host tissues or factors, including, but not limited to various cells of the immune system (effector cells), Fc receptors and the first component, C1q, of the C1 complex of the classical complement system.

Antibodies of the invention may be monoclonal antibodies (mAbs), in the sense that they represent a set of unique heavy and light chain variable domain sequences as expressed from a single B-cell or by a clonal population of B cells. Antibodies of the invention may be produced and purified using various methods that are known to a person skilled in the art. For example, antibodies may be produced from hybridoma cells. Antibodies may be produced by B-cell expansion. Antibodies or fragment thereof may be recombinantly expressed in mammalian or microbial expression systems, or by in vitro translation.

Antibodies or fragment thereof may also be recombinantly expressed as cell surface bound molecules, by means of e.g. phage display, bacterial display, yeast display, mammalian cell display or ribosome or mRNA display.

Antibodies of the current invention may be isolated. The term "isolated antibody" refers to an antibody that has been separated and/or recovered from (an) other component(s) in the environment in which it was produced and/or that has been purified from a mixture of components present in the environment in which it was produced.

Certain antigen-binding fragments of antibodies may be suitable in the context of the current invention, as it has been shown that the antigen-binding function of an antibody can be performed by fragments of a full-length antibody. The term "antigen-binding fragment" of an antibody refers to one or more fragment(s) of an antibody that retain(s) the ability to specifically bind to or recognise an antigen, such as FIX/FIXa, FX/FXa or another target molecule, as described herein. Examples of antigen-binding fragments include (but is not limited to) Fab, Fab', Fab2, Fab'2, Fv (typically the combination of $V_L$ and $V_H$ domains of a single arm of an antibody), single-chain Fv (scFv); see e.g. Bird et al. *Science* 1988; 242:423-426; and Huston et al. *PNAS* 1988; 85:5879-5883), dsFv, Fd (typically the $V_H$ and $C_H1$ domain), monovalent molecules comprising both a single $V_H$ and a single V_domain; minibodies, diabodies, triabodies, tetrabodies, and kappa bodies (see, e.g. III et al (1997) Protein Eng 10:949-57); as well as one or more isolated CDRs or a functional paratope, where the isolated CDRs or antigen-binding residues or polypeptides can be associated or linked together so as to form a functional antibody fragment. These antibody fragments may be obtained using conventional techniques known to those skilled in the art, and the fragments may be screened for utility in the same manner as intact antibodies.

"Fab fragments" of an antibody, including "Fab" and "Fab'2" fragments, can be derived from an antibody by cleavage of the heavy chain in the hinge region on the N-terminal or C-terminal side, respectively, of the hinge cysteine residues connecting the heavy chains of the antibody. A "Fab" fragment includes the variable and constant domains of the light chain and the variable domain and $C_H1$ domain of the heavy chain. "Fab'2" fragments comprise a pair of "Fab" fragments that are generally covalently linked by their hinge cysteines. A Fab' is formally derived from a Fab'2 fragment by cleavage of the hinge disulfide bonds connecting the heavy chains in the Fab'2. Other chemical couplings than disulfide linkages of antibody fragments are also known in the art. A Fab fragment retains the ability of the parent antibody to bind to its antigen, potentially with a lower affinity. Fab'2 fragments are capable of bivalent binding, whereas Fab and Fab' fragments can only bind monovalently. Generally, Fab fragments lack the constant $C_H2$ and $C_H3$ domains, i.e. the Fc part, where interaction with the Fc receptors and C1q would occur. Thus, Fab fragments are in general devoid of effector functions. Fab fragments may be produced by methods known in the art, either by enzymatic cleavage of an antibody, e.g. using papain to obtain the Fab or pepsin to obtain the Fab'2, Fab fragments including Fab, Fab', Fab'2 may be produced recombinantly using techniques that are well-known to the person skilled in the art.

An "Fv" (fragment variable) fragment is an antibody fragment that contains a complete antigen recognition and binding site, and generally comprises one heavy and one light chain variable domain in association that can be covalent in nature, for example in a single chain variable domain fragment (scFv). It is in this configuration that the three hypervariable regions of each variable domain interact to define an antigen-binding site on the surface of the $V_H$-$V_L$ dimer. Collectively, the six hypervariable regions or a subset thereof confer antigen binding specificity to the antibody.

"Single-chain Fv" or "scFv" antibody comprise the $V_H$ and $V_L$ domains of antibody, where these domains are present in a single polypeptide chain. Generally, the Fv polypeptide further comprises a polypeptide linker between the $V_H$ and $V_L$ domains that enables the scFv to form the desired structure for antigen binding. For a review of scFv, see Pluckthun, 1994, In: *The Pharmacology of Monoclonal Antibodies*, Vol. 113, Rosenburg and Moore eds. Springer-Verlag, New York, pp. 269-315.

"Single-chain Fab" or "scFab" antibody comprise the $V_H$, $C_H1$, $V_L$ and $C_L$ domains of an antibody, where these domains are present in a single polypeptide chain. Generally, the Fab polypeptide further comprises a polypeptide linker between either $V_H$ and $C_L$ or $V_L$ and $C_H1$ domains that enables the scFab to form the desired structure for antigen binding (Koerber et al. (2015) *J Mol Biol.* 427:576-86).

The term "diabodies" refers to small antibody fragments with two antigen-binding sites, in which fragments comprise a heavy chain variable domain (VA) connected to a light chain variable domain ($V_L$) in the same polypeptide chain ($V_H$ and $V_L$). By using a linker that is too short to allow pairing between the two variable domains on the same chain, the variable domains are forced to pair with complementary domains of another chain, creating two antigen-binding sites.

The expression "linear antibodies" refers to antibodies as described in Zapata et al. (1995) Protein Eng. 8:1057-1062. Briefly, these antibodies contain a pair of tandem Fd segments ($V_H$-$C_H1$-$V_H$-$C_H1$) that, together with complementary light chain polypeptides, form a pair of antigen binding regions. Linear antibodies can be bispecific or monospecific.

Antibody fragments may be obtained using conventional recombinant or protein engineering techniques and the fragments can be screened for binding to FIX and the activated form thereof, FX or another function, in the same manner as intact antibodies.

Antibody fragments of the invention may be made by truncation, e.g. by removal of one or more amino acids from the N and/or C-terminal ends of a polypeptide. Fragments may also be generated by one or more internal deletions.

An antibody of the invention may be, or may comprise, a fragment of the antibody, or a variant of any of the antibodies disclosed herein. An antibody of the invention may be, or may comprise, an antigen binding portion of one of these antibodies, or variants thereof. For example, an antibody of the invention may be a Fab fragment of one of these antibodies or variants thereof, or it may be a single chain antibody derived from one of these antibodies, or a variant thereof. Also, an antibody of the invention may be a combination of a full length antibody and fragment thereof.

The term "monospecific" antibody as used herein, refers to an antibody which is capable of binding to one particular epitope (including but not limited to bivalent antibodies).

The term "bispecific" antibody as used herein, refers to an antibody which is capable of binding to two different antigens or two different epitopes on the same antigen.

The term "trispecific" antibody as used herein, refers to an antibody which is capable of binding to three different antigens or three different epitopes on the same antigen or three different epitopes present on two different antigens.

The term "multispecific" antibody as used herein, refers to an antibody which is capable of binding to two or more different antigens or two or more different epitopes on the same antigen. Multispecific antibodies thus comprise bi- and trispecific antibodies.

Bispecific antibodies in full length IgG format can be generated by fusion of two individual hybridomas to form a hybrid quadroma which produces a mixture of antibodies including a fraction of bispecific heterodimerising antibodies (Chelius D. et al.; *MAbs.* 2010 May-June; 2(3): 309-319). Bispecific heterodimerising antibodies may alternatively be produced by using recombinant technologies. Heterodimerisation can also be achieved by engineering the dimerisation interface of the Fc region to promote heterodimerisation. One example hereof is the so-called knob-in-hole mutations where sterically bulky side chains (knobs) are introduced in one Fc matched by sterically small side chains (holes) on the opposite Fc thereby creating steric complementarity promoting heterodimerisation. Other methods for engineered heterodimerisation Fc interfaces are electrostatic complementarity, fusion to non-IgG heterodimerisation domains or utilising the natural Fab-arm exchange phenomenon of human IgG4 to control heterodimerisation. Examples of heterodimerised bispecific antibodies are well described in the literature, e.g. (Klein C, et al.; *MAbs.* 2012 November-December; 4(6): 653-663). Special attention has to be paid to the light chains in heterodimeric antibodies. Correct pairing of LCs and HCs can be accomplished by the use of a common light chain. Again engineering of the LC/HC interface can be used to promote heterodimerisation or light chain cross-over engineering as in CrossMabs. In vitro re-assembly under mildly reducing conditions of antibodies from two individual IgGs containing appropriate mutations can also be used to generate bispecific antibodies (e.g. Labrijn et al., *PNAS,* 110, 5145-5150 (2013)). Also the natural Fab-arm exchange method is reported to ensure correct light chains paring. Multispecific antibody-based molecules may also be expressed recombinantly as fusion proteins combining the natural modules of IgGs to form multispecific and multivalent antibody derivatives as described in the literature. Examples of fusion antibodies are DVD-Igs, IgG-scFV, Diabodies, DARTs etc. Specific detection or purification tags, half-life extension moieties or other components can be incorporated in the fusion proteins. Additional non-IgG modalities may also be incorporated in the fusion proteins. Bispecific full length antibodies based on Fc heterodimerisation are commonly referred to as asymmetic IgGs, irrespective of the LC paring methodology.

Generally, bispecific antibodies may be produced in a variety of molecular formats as reviewed by Brinkmann et al. (Brinkmann et al. The making of bispecific antibodies. *Mabs* 9, 182-212 (2017)).

Multispecific antibody-based molecules may also be produced by chemical conjugation or coupling of individual full length IgGs or coupling of fragments of IgGs to form multispecific and multivalent antibody derivatives as described in the literature. Examples are chemically coupled Fab fragments, IgG-dimer etc. Specific detection or purification tags, half-life extension molecules or other components can be incorporated in the conjugate proteins. Additional non-IgG polypeptide may also be incorporated in the fusion proteins. Multispecific molecules may also be produced by combining recombinant and chemical methods including those described above.

In one aspect, an antibody of the invention is a chimeric antibody, a human antibody or a humanised antibody. Such antibody can be generated by using, for example, suitable antibody display or immunization platforms or other suitable platforms or methods known in the field. The term "human antibody", as used herein, is intended to include antibodies having variable domains in which at least a portion of a framework region and/or at least a portion of a CDR region are derived from human germline immunoglobulin sequences. For example, a human antibody may have variable domains in which both the framework and CDR regions are derived from human germline immunoglobulin sequences. Furthermore, if the antibody contains a constant region, the constant region or a portion thereof is also derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo).

Such a human antibody may be a human monoclonal antibody. Such a human monoclonal antibody may be produced by a hybridoma which includes a B cell obtained from a transgenic nonhuman animal, e.g., a transgenic mouse, having a genome comprising human immunoglobulin heavy and light chain gene segments repertoires, fused to an immortalised cell.

Human antibodies may be isolated from sequence libraries built on selections of human germline sequences, further diversified with natural and synthetic sequence diversity.

Human antibodies may be prepared by in vitro immunisation of human lymphocytes followed by transformation of the lymphocytes with Epstein-Barr virus.

Human antibodies may be produced by recombinant methods known in the art.

The term "human antibody derivative" refers to any modified form of the human antibody, such as a conjugate of the antibody and another agent or antibody.

The term "humanised antibody", as used herein, refers to a human/non-human antibody that contains a sequence (CDR regions or parts thereof) derived from a non-human immunoglobulin. A humanised antibody is, thus, a human immunoglobulin (recipient antibody) in which residues from at least a hypervariable region of the recipient are replaced by residues from a hypervariable region of an antibody from a non-human species (donor antibody) such as from a mouse, rat, rabbit or non-human primate, which have the desired specificity, affinity, sequence composition and functionality. In some instances, framework (FR) residues of the human immunoglobulin are replaced by corresponding non-human residues. An example of such a modification is the introduction of one or more so-called back-mutations, which are typically amino acid residues derived from the donor antibody. Humanisation of an antibody may be carried out using recombinant techniques known to the person skilled in the art (see, e.g., Antibody Engineering, Methods in Molecular Biology, vol. 248, edited by Benny K. Lo). A suitable human recipient framework for both the light and heavy chain variable domain may be identified by, for example, sequence or structural homology. Alternatively, fixed recipient frameworks may be used, e.g., based on knowledge of structure, biophysical and biochemical properties. The recipient frameworks can be germline derived or derived from a mature antibody sequence. CDR regions from the donor antibody can be transferred by CDR grafting. The CDR grafted humanised antibody can be further optimised for e.g. affinity, functionality and biophysical properties by identification of critical framework positions where re-introduction (back-mutation) of the amino acid residue from the donor antibody has beneficial impact on the properties of the humanised antibody. In addition to donor antibody derived back-mutations, the humanised antibody can be engineered by introduction of germline residues in the CDR or framework regions, elimination of immunogenic epitopes, affinity maturation, etc.

Furthermore, humanised antibodies may comprise residues that are not found in the recipient antibody or in the donor antibody. These modifications are made to further refine antibody performance. In general, a humanised antibody will comprise at least one-typically two-variable domains, in which all or substantially all of the CDR regions correspond to those of a non-human immunoglobulin and in which all or substantially all of the FR residues are those of a human immunoglobulin sequence. The humanised antibody can, optionally, also comprise at least a portion of an immunoglobulin constant region (Fc), typically that of a human immunoglobulin.

The term “humanised antibody derivative” refers to any modified form of the humanised antibody, such as a conjugate of the antibody and a chemical agent or a conjugate of the antibody with another antibody.

The term “chimeric antibody”, as used herein, refers to an antibody comprising portions of antibodies derived from two or more species. For example, the genes encoding such antibody comprise genes encoding variable domains and genes encoding constant domains originated from two different species. For example, the genes encoding variable domains of a mouse monoclonal antibody may be joined to the genes encoding the constant domains of an antibody of human origin.

The fragment crystallisable region (“Fc region”/“Fc domain”) of an antibody is the C-terminal region of an antibody, which comprises the hinge and the constant $C_H2$ and $C_H3$ domains.

The Fc domain may interact with cell surface receptors called Fc receptors, as well as some proteins of the complement system. The Fc region enables antibodies to interact with the immune system. In one aspect of the invention, antibodies may be engineered to include modifications within the Fc region, typically to alter one or more of its functional properties, such as serum half-life, complement fixation, Fc-receptor binding, protein stability and/or antigen-dependent cellular cytotoxicity, or lack thereof, among others. Furthermore, an antibody of the invention may be chemically modified (e.g., one or more chemical moieties can be attached to the antibody) or be modified to alter its glycosylation, again to alter one or more functional properties of the antibody. An IgG1 antibody may carry a modified Fc domain comprising one or more, and perhaps all of the following mutations that will result in decreased affinity to certain Fc-gamma receptors (L234A, L235E, and G237A) and in reduced C1q-mediated complement fixation (A330S and P331S), respectively (residue numbering according to the EU index). Alternatively, other amino acid substitutions, and combinations thereof and combinations with the above mentioned, known in the art to lead to altered (reduced or increased) Fc-gamma receptor binding may be used.

The isotype of an antibody of the invention may be IgG, such as IgG1, such as IgG2, such as IgG4. If desired, the class of an antibody may be “switched” by known techniques. For example, an antibody that was originally produced as an IgM molecule may be class switched to an IgG antibody. Class switching techniques also may be used to convert one IgG subclass to another, for example: from IgG1 to IgG2 or IgG4; from IgG2 to IgG1 or IgG4; or from IgG4 to IgG1 or IgG2. Engineering of antibodies to generate constant region chimeric molecules, by combination of regions from different IgG subclasses, can also be performed. In one embodiment the hinge region of the antibody is modified such that the number of cysteine residues in the hinge region is altered, e.g., increased or decreased. This approach is described further for instance in U.S. Pat. No. 5,677,425 by Bodmer et al.

The constant region may be modified to stabilise the antibody, e.g., to reduce the risk of a bivalent antibody separating into half antibodies. For example, in an IgG4 constant region, residue S228 (according to the EU numbering index and S241 according to Kabat) may be mutated to a proline (P) residue to stabilise inter heavy chain disulphide bridge formation at the hinge (see, e.g., Angal et al. *Mol Immunol.* 1993; 30:105-8).

Antibodies or fragment thereof may be defined in terms of their complementarity-determining regions (CDRs). The term “complementarity-determining region” or “hypervariable region”, when used herein, refers to the regions of an antibody in which amino acid residues involved in antigen-binding are situated. The region of hypervariability or CDRs can be identified as the regions with the highest variability in amino acid alignments of antibody variable domains. Databases can be used for CDR identification such as the Kabat database, the CDRs e.g. being defined as comprising amino acid residues 24-34 (L1), 50-56 (L2) and 89-97 (L3) of the light-chain variable domain and 31-35 (H1), 50-65 (H2) and 95-102 (H3) in the heavy-chain variable domain; (Kabat et al. 1991*; Sequences of Proteins of Immunological Interest*, Fifth Edition, U.S. Department of Health and Human Services, NIH Publication No. 91-3242). Alternatively CDRs can be defined as those residues from a “hypervariable loop” (residues 26-33 (L1), 50-52 (L2) and 91-96 (L3) in the light-chain variable domain and 26-32 (H1), 53-55 (H2) and 96-101 (H3) in the heavy-chain variable domain; Chothia and Lesk, *J. Mol. Biol.* 1987; 196:901-917). Typically, the numbering of amino acid residues in this region is performed by the method described in Kabat et al. supra. Phrases such as “Kabat position”, “Kabat residue”, and “according to Kabat” herein refer to this numbering system for heavy chain variable domains or light chain variable domains. Using the Kabat numbering system, the actual linear amino acid sequence of a peptide may contain fewer or additional amino acids corresponding to a shortening of, or insertion into, a framework (FR) or CDR of the variable domain. For example, a heavy chain variable domain may include amino acid insertions (residue 52a, 52b and 52c according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a “standard” Kabat numbered sequence.

The term “framework region” or “FR” residues refer to those $V_H$ or $V_L$ amino acid residues that are not within the CDRs, as defined herein.

The term “procoagulant antibody” refers to an antibody which potentiates blood coagulation for example by accelerating the process of blood coagulation and/or increasing the enzymatic activity of one or more coagulation factors.

The term “procoagulant activity” refers to the ability of a compound, such as an antibody, to potentiate blood coagulation for example by accelerating the process of blood coagulation and/or increasing the enzymatic activity of one or more coagulation factors.

The activity of procoagulant antibodies including bi-, tri and multispecific antibodies may be determined by methods known in the art. Standard assays include whole blood-Thrombin-Generation Test (TGT), measuring of clotting time by thrombelastography (TEG) and FXa generation assays (see e.g. WO2018/141863).

The term “stimulating the enzymatic activity of FIXa” refers to stimulation as determined using the methodology of Example 9.

The term “antigen” (Ag) refers to the molecular entity used for immunisation of an immunocompetent vertebrate to produce the antibody (Ab) that recognizes the Ag. Herein, Ag is termed more broadly and is generally intended to include target molecules that are specifically recognized by the Ab, thus including fragments or mimics of the molecule used in the immunisation process, or other process, e.g. phage display, used for generating the Ab.

The present invention encompasses variants of the antibodies, or antigen-binding fragments thereof of the invention, which may comprise 1, 2 or 3 amino acid substitutions and/or deletions and/or insertions in the individual sequences disclosed herein.

In one aspect, "Substitution" variants involve the replacement of one or more amino acid(s) with the same number of amino acid(s). Substitutions may be, but are not limited to, conservative substitutions. For example, an amino acid may be substituted to an amino acid with similar biochemical properties, for example, a basic amino acid may be substituted to another basic amino acid (e.g. lysine to arginine), an acidic amino acid may be substituted to another acidic amino acid (e.g glutamate to aspartate), a neutral amino acid may be substituted to another neutral amino acid (e.g threonine to serine), a charged amino acid may be substituted to another charged amino acid (e.g. glutamate to aspartate), a hydrophilic amino acid may be substituted to another hydrophilic amino acid (e.g. asparagine to glutamine), a hydrophobic amino acid may be substituted to another hydrophobic amino acid (e.g. alanine to valine), a polar amino acid may be substituted to another polar amino acid (e.g. serine to threonine), an aromatic amino acid may be substituted to another aromatic amino acid (e.g. phenylalanine to tryptophan) and an aliphatic amino acid may be substituted to another aliphatic amino acid (e.g. leucine to isoleucine).

In another aspect, variants comprises a structural analog of the amino acid which appears in the sequence of the antibodies, or antigen-binding fragments thereof of the invention.

The term "binding affinity" is herein used as a measure of the strength of a non-covalent interaction between two molecules, e.g. an antibody, or fragment thereof, and an antigen.

The term "binding affinity" is used to describe monovalent interactions.

Binding affinity between two molecules, e.g. an antibody, or fragment thereof, and an antigen, through a monovalent interaction may be quantified by determining the equilibrium dissociation constant ($K_D$). $K_D$ can be determined by measurement of the kinetics of complex formation and dissociation, e.g. by the Surface Plasmon Resonance (SPR) method or the Isothermal Titration calorimetry (ITC) method. The rate constants corresponding to the association and the dissociation of a monovalent complex are referred to as the association rate constant $k_a$ (or $k_{on}$) and dissociation rate constant $k_d$ (or $k_{off}$), respectively. $K_D$ is related to $k_a$ and $k_d$ through the equation $K_D=k_d/k_a$.

Following the above definition, binding affinities associated with different molecular interactions, such as comparison of the binding affinity of different antibodies for a given antigen, may be compared by comparison of the $K_D$ values for the individual antibody/antigen complexes.

The value of the dissociation constant can be determined directly by well-known methods. Standard assays to evaluate the binding ability of ligands such as antibodies towards targets are known in the art and include, for example, ELISAs, Western blots, RIAs, and flow cytometry analysis. The binding kinetics and binding affinity of the antibody also can be assessed by standard assays known in the art, such as SPR. Preferably, however, isothermal titration calorimetry (ITC) may be used to measure affinities for an antibody/target interaction as well as to derive thermodynamic parameters for the interaction.

A competitive binding assay can be conducted in which the binding of the antibody to the target is compared to the binding of the target by another ligand of that target, such as another antibody.

The $K_D$ of an antibody of the invention for its target may be less than 100 μM such as less than 10 μM, such as less than 9 μM, such as less than 8 μM, such as less than 7 μM, such as less than 6 μM, such as less than 5 μM, such as less than 4 μM, such as less than 3 μM, such as less than 2 μM, such as less than 1 μM, such as less than 0.9 μM, such as less than 0.8 μM, such as less than 0.7 μM, such as less than 0.6 μM, such as less than 0.5 μM, such as less than 0.4 μM, such as less than 0.3 μM, such as less than 0.2 μM, such as less than 0.1 μM.

In one such embodiment the antibody is a bispecific antibody comprising an anti-FX arm with a $K_D$ towards FX of less than 100 μM such as less than 10 μM, such as less than 9 μM, such as less than 8 μM, such as less than 7 μM, such as less than 6 μM, such as less than 5 μM, such as less than 4 μM, such as less than 3 μM, such as less than 2 μM, such as less than 1 UM, such as less than 0.9 μM, such as less than 0.8 μM, such as less than 0.7 μM, such as less than 0.6 μM, such as less than 0.5 μM, such as less than 0.4 μM, such as less than 0.3 UM, such as less than 0.2 μM, such as less than 0.1 μM, such as less than 0.09 μM, such as less than 0.08 μM, such as less than 0.07 μM, such as less than 0.06 μM, such as less than 0.05 μM, such as less than 0.04 μM, such as less than 0.03 μM, such as less than 0.02 μM, such as less than 0.01 μM, such as less than 9 nM, such as less than 8 nM, such as less than 7 nM, such as less than 6 nM, such as less than 5 nM, such as less than 4 nM, such as less than 3 nM, such as less than 2 nM, such as less than 1 nM such as less than 0.5 nM. The antibodies and antibody fragment thereof as described herein may be combined with other antibodies and antibody fragments known in the art creating bispecific, trispecific or multispecific antibody molecules. Compounds mimicking FVIII cofactor function have previously been created using antibodies targeting FIX(a) and FX(a), which in some embodiments may potentially each substitute for the FIX(a) or FX(a) antibodies described herein. It is thus clear that the antibodies targeting FIX(a) and FX(a) of the present invention and in particular the antigen-binding fragments thereof are of separate interest as individual component (intermediate) molecules, as part of a bi-, tri- or multispecific antibody comprising at least one FIX(a) and/or FX(a) binding domain.

Pharmaceutical Formulations

In another aspect, the present invention provides compositions and formulations comprising compounds of the invention, such as the antibodies described herein. For example, the invention provides a pharmaceutical composition that comprises one or more antibodies of the invention, formulated together with a pharmaceutically acceptable carrier.

Accordingly, one object of the invention is to provide a pharmaceutical formulation comprising such an antibody which is present in a concentration from 0.25 mg/ml to 250 mg/ml, and wherein said formulation has a pH from 2.0 to 10.0. The formulation may further comprise one or more of a buffer system, a preservative, a tonicity agent, a chelating agent, a stabilizer, or a surfactant, as well as various combinations thereof. The use of preservatives, isotonic agents, chelating agents, stabilizers and surfactants in pharmaceutical compositions is well-known to the skilled person. Reference may be made to Remington: The Science and Practice of Pharmacy, 19th edition, 1995.

In one embodiment the pharmaceutical formulation is an aqueous formulation. Such a formulation is typically a solution or a suspension, but may also include colloids, dispersions, emulsions, and multi-phase materials. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment the pharmaceutical formulation is a freeze-dried formulation, to which a solvent and/or a diluent is added prior to use.

In a further aspect, the pharmaceutical formulation comprises an aqueous solution of such an antibody, and a buffer, wherein the antibody is present in a concentration from 1 mg/ml or above, and wherein said formulation has a pH from about 2.0 to about 10.0.

In one embodiment the present invention relates to an injection device with content of said composition. In some embodiments the pharmaceutical composition of the invention is intended for use and/or contained in an injection device. In some embodiments, the injection device is a disposable, pre-filled, multi-dose pen of the FlexTouch® type (supplier Novo Nordisk A/S, Denmark). In some embodiments the injection device is a single shot device.

In some embodiments the injection device is a fixed dose device, such as one configured to deliver multiple predetermined doses of drug, sometimes referred to as a multiple fixed dose device or a fixed dose, multi-shot device.

In one embodiment the pharmaceutical composition of the invention is administered using an injection device comprising a tube having a needle gauge of 20 or greater.

In one embodiment a bispecific antibody according to table 1 herein is administered using an injection device comprising a tube having a needle gauge of 20 or greater.

In one embodiment a bispecific antibody according to table 1 herein is administered using an injection device comprising a tube having a needle gauge of 20 to 36. In one such embodiment the bispecific antibody is selected from a list consisting of bimAb1A, bimAb2A, bimAb3A, bimAb4A, bimAb5A, bimAb6A, bimAb7A, bimAb8A, bimAb1B, bimAb2B, bimAb3B bimAb4B, bimAb5B, bimAb6B, bimAb7B and bimAb8B.

Administration and Dosages

A compound of the invention, such as an antibody, may be administered parenterally, such as intravenously, such as intramuscularly, such as subcutaneously. Alternatively, an antibody of the invention may be administered via a non-parenteral route, such as perorally or topically. An antibody of the invention may be administered prophylactically. An antibody of the invention may be administered therapeutically (on demand).

The dose of the compounds to be delivered may be from about 0.01 mg to 500 mg of the compound per day, preferably from about 0.1 mg to 250 mg per day, and more preferably from about 0.5 mg to about 250 mg per day, per week, per second week or per month as loading and maintenance doses, depending on the severity of the condition. A suitable dose may also be adjusted for a particular compound based on the properties of that compound, including its in vivo half-life or mean residence time and its biological activity. For example, compounds to be delivered could in one embodiment be administered once weekly, or in another embodiment once every second week or in another embodiment once monthly and in either of said embodiments in a dose of for example 0.005, 0.0075, 0.01, 0.015, 0.02, 0.025, 0.03, 0.035, 0.04, 0.045, 0.05, 0.075, 0.1, 0.125, 0.15, 0.175, 0.2, 0.25, 0.3, 0.35, 0.4, 0.45, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5 or 10 mg per kg body weight.

The compositions containing the compounds as disclosed herein can be administered for prophylactic and/or in some embodiments therapeutic treatments. In therapeutic applications, compositions are administered to a subject already suffering from a disease, such as any bleeding disorder as described above, in an amount sufficient to cure, alleviate or partially arrest the disease and its complications. An amount adequate to accomplish this is defined as "therapeutically effective amount". As will be understood by the person skilled in the art amounts effective for this purpose will depend on the severity of the disease or injury as well as the weight and general state of the subject.

EMBODIMENTS

The invention is further described by the following embodiments:

1. An antibody or antigen-binding fragment thereof capable of binding to Factor IX (FIX) according to SEQ ID NO:89 and/or the activated form thereof (FIXa).
2. The antibody or antigen-binding fragment thereof according to embodiment 1, wherein the antibody is a Fab.
3. The antibody or antigen-binding fragment thereof according to embodiment 1 or 2, wherein the antibody or antigen-binding fragment thereof comprises
   - the CDR sequences of the heavy chain variable domain identified by SEQ ID NO:25 and the CDR sequences of the light chain variable domain identified by SEQ ID NO: 29; or
   - the CDR sequences of the heavy chain variable domain identified by SEQ ID NO:33 and the CDR sequences of the light chain variable domain identified by SEQ ID NO: 37; or
   - the CDR sequences of the heavy chain variable domain identified by SEQ ID NO:41 and the CDR sequences of the light chain variable domain identified by SEQ ID NO: 45; or
   - the CDR sequences of the heavy chain variable domain identified by SEQ ID NO:49 and the CDR sequences of the light chain variable domain identified by SEQ ID NO: 53; or
   - the CDR sequences of the heavy chain variable domain identified by SEQ ID NO:57 and the CDR sequences of the light chain variable domain identified by SEQ ID NO: 61; or
   - the CDR sequences of the heavy chain variable domain identified by SEQ ID NO:65 and the CDR sequences of the light chain variable domain identified by SEQ ID NO: 69; or
   - the CDR sequences of the heavy chain variable domain identified by SEQ ID NO:73 and the CDR sequences of the light chain variable domain identified by SEQ ID NO: 77; or
   - the CDR sequences of the heavy chain variable domain identified by SEQ ID NO:81 and the CDR sequences of the light chain variable domain identified by SEQ ID NO: 85.

4. The antibody or antigen-binding fragment thereof according to any of the previous embodiments, wherein the antibody or antigen-binding fragment thereof comprises
   - a heavy chain variable domain identified by SEQ ID NO:25 and a light chain variable domain identified by SEQ ID NO:29; or
   - a heavy chain variable domain identified by SEQ ID NO:33 and a light chain variable domain identified by SEQ ID NO:37; or
   - a heavy chain variable domain identified by SEQ ID NO:41 and a light chain variable domain identified by SEQ ID NO:45; or
   - a heavy chain variable domain identified by SEQ ID NO:49 and a light chain variable domain identified by SEQ ID NO:53; or
   - a heavy chain variable domain identified by SEQ ID NO:57 and a light chain variable domain identified by SEQ ID NO:61; or
   - a heavy chain variable domain identified by SEQ ID NO:65 and a light chain variable domain identified by SEQ ID NO:69; or
   - a heavy chain variable domain identified by SEQ ID NO:73 and a light chain variable domain identified by SEQ ID NO:77; or
   - a heavy chain variable domain identified by SEQ ID NO:81 and a light chain variable domain identified by SEQ ID NO:85.
5. An antibody or antigen-binding fragment thereof capable of binding to FX (SEQ ID NO: 90) and/or the activated form thereof (FXa).
6. The antibody according to embodiment 5, wherein the antibody is a Fab.
7. The antibody or antigen-binding fragment thereof according to any of embodiments 5 or 6, wherein
   - the antibody or antigen-binding fragment thereof comprises the CDR sequences of the heavy chain variable domain identified by SEQ ID NO:1 and the CDR sequences of the light chain variable domain identified by SEQ ID NO:5;
   - or
   - the heavy chain variable domain identified by SEQ ID NO:17 and the CDR sequences of the light chain variable domain identified by SEQ ID NO:21.
8. The antibody or antigen-binding fragment thereof according to any of the previous embodiments, wherein the antibody or antigen-binding fragment thereof comprises
   - a heavy chain variable domain identified by SEQ ID NO:1 and a light chain variable domain identified by SEQ ID NO:5; or
   - a heavy chain variable domain identified by SEQ ID NO: 17 and a light chain variable domain identified by SEQ ID NO:21.
9. A multispecific antibody or antigen-binding fragment thereof capable of binding to FIX according to SEQ ID NO:89 or the activated form thereof (FIXa), and FX (SEQ ID NO: 90) or the activated form thereof (FXa).
10. The multispecific antibody or antigen-binding fragment thereof according to embodiment 9, wherein the antibody comprises an antibody or antigen-binding fragment thereof according to any of the previous embodiments 1-4.
11. The multispecific antibody or antigen-binding fragment thereof according to embodiment 9, wherein the antibody comprises an antibody or antigen-binding fragment thereof according to any of the previous embodiments 5-8.
12. The multispecific antibody or antigen-binding fragment thereof according to embodiment 9, wherein the antibody comprises an antibody or antigen-binding fragment thereof according to any of the previous embodiments 1~4 and an antigen-binding fragment according to any of the previous embodiments 5-8.
13. The multispecific antibody or antigen-binding fragment thereof according to any of embodiments 9-12 comprising
   - the anti-FIX(a) antibody heavy chain CDR3 sequence identified by SEQ ID NO:28, optionally comprising 1, 2 or 3 amino acid substitutions and/or deletions and/or insertions, and
   - the anti-FIX(a) antibody light chain CDR3 sequence identified by SEQ ID NO:32, optionally comprising 1, 2 or 3 amino acid substitutions and/or deletions and/or insertions, and
   - the anti-FX(a) antibody heavy chain CDR3 sequence identified by SEQ ID NO:20, optionally comprising 1, 2 or 3 amino acid substitutions and/or deletions and/or insertions, and
   - the anti-FX(a) antibody light chain CDR3 sequence identified by SEQ ID NO:24, optionally comprising 1, 2 or 3 amino acid substitutions and/or deletions and/or insertions; or
   - the anti-FIX(a) antibody heavy chain CDR3 sequence identified by SEQ ID NO:28, optionally comprising 1, 2 or 3 amino acid substitutions and/or deletions and/or insertions, and
   - the anti-FIX(a) antibody light chain CDR3 sequence identified by SEQ ID NO:32, optionally comprising 1, 2 or 3 amino acid substitutions and/or deletions and/or insertions, and
   - the anti-FX(a) antibody heavy chain CDR3 sequence identified by SEQ ID NO:4, optionally comprising 1, 2 or 3 amino acid substitutions and/or deletions and/or insertions, and
   - the anti-FX(a) antibody light chain CDR3 sequence identified by SEQ ID NO:8, optionally comprising 1, 2 or 3 amino acid substitutions and/or deletions and/or insertions; or
   - the anti-FIX(a) antibody heavy chain CDR3 sequence identified by SEQ ID NO:36, optionally comprising 1, 2 or 3 amino acid substitutions and/or deletions and/or insertions, and
   - the anti-FIX(a) antibody light chain CDR3 sequence identified by SEQ ID NO:40, optionally comprising 1, 2 or 3 amino acid substitutions and/or deletions and/or insertions, and
   - the anti-FX(a) antibody heavy chain CDR3 sequence identified by SEQ ID NO:20, optionally comprising 1, 2 or 3 amino acid substitutions and/or deletions and/or insertions, and
   - the anti-FX(a) antibody light chain CDR3 sequence identified by SEQ ID NO:24, optionally comprising 1, 2 or 3 amino acid substitutions and/or deletions and/or insertions; or
   - the anti-FIX(a) antibody heavy chain CDR3 sequence identified by SEQ ID NO:36, optionally comprising 1, 2 or 3 amino acid substitutions and/or deletions and/or insertions, and the anti-FIX(a) antibody light chain CDR3 sequence identified by SEQ ID NO:40, optionally comprising 1, 2 or 3 amino acid substitutions and/or deletions and/or insertions, and the anti-FIX(a) antibody light chain CDR3 sequence identified by SEQ ID NO:4, optionally comprising 1, 2 or 3 amino acid substitutions and/or deletions and/or insertions, and the anti-FX(a) antibody light chain CDR3 sequence identified by SEQ ID NO:8, optionally comprising 1, 2 or 3 amino acid substitutions and/or deletions and/or insertions; or the anti-FIX(a) antibody heavy chain CDR3 sequence identified by SEQ ID NO:44, optionally comprising 1, 2 or 3 amino acid substitutions and/or deletions and/or insertions, and the anti-FIX(a) antibody light chain CDR3 sequence identified by SEQ ID NO:48, optionally comprising 1, 2 or 3 amino acid substitutions and/or deletions and/or insertions, and the anti-FX(a) antibody heavy chain CDR3 sequence identified by SEQ ID NO:20, optionally comprising 1, 2 or 3 amino acid substitutions and/or deletions and/or insertions, and the anti-FX(a) antibody light chain CDR3 sequence identified by SEQ ID NO:24, optionally comprising 1, 2 or 3 amino acid substitutions and/or deletions and/or insertions; or the anti-FIX(a) antibody heavy chain CDR3 sequence identified by SEQ ID NO:44 optionally comprising 1, 2 or 3 amino acid substitutions and/or deletions and/or insertions, and the anti-FIX(a) antibody light chain CDR3 sequence identified by SEQ ID NO:48, optionally comprising 1, 2 or 3 amino acid substitutions and/or deletions and/or insertions, and the anti-FX(a) antibody heavy chain CDR3 sequence identified by SEQ ID NO:4, optionally comprising 1, 2 or 3 amino acid substitutions and/or deletions and/or insertions, and the anti-FX(a) antibody light chain CDR3 sequence identified by SEQ ID NO:8, optionally comprising 1, 2 or 3 amino acid substitutions and/or deletions and/or insertions; or the anti-FIX(a) antibody heavy chain CDR3 sequence identified by SEQ ID NO:52, optionally comprising 1, 2 or 3 amino acid substitutions and/or deletions and/or insertions, and the anti-FIX(a) antibody light chain CDR3 sequence identified by SEQ ID NO:56, optionally comprising 1, 2 or 3 amino acid substitutions and/or deletions and/or insertions, and the anti-FX(a) antibody heavy chain CDR3 sequence identified by SEQ ID NO:20, optionally comprising 1, 2 or 3 amino acid substitutions and/or deletions and/or insertions, and the anti-FX(a) antibody light chain CDR3 sequence identified by SEQ ID NO:24, optionally comprising 1, 2 or 3 amino acid substitutions and/or deletions and/or insertions; or the anti-FIX(a) antibody heavy chain CDR3 sequence identified by SEQ ID NO:52, optionally comprising 1, 2 or 3 amino acid substitutions and/or deletions and/or insertions, and the anti-FIX(a) antibody light chain CDR3 sequence identified by SEQ ID NO:56, optionally comprising 1, 2 or 3 amino acid substitutions and/or deletions and/or insertions, and the anti-FX(a) antibody heavy chain CDR3 sequence identified by SEQ ID NO:4, optionally comprising 1, 2 or 3 amino acid substitutions and/or deletions and/or insertions, and the anti-FX(a) antibody light chain CDR3 sequence identified by SEQ ID NO:8, optionally comprising 1, 2 or 3 amino acid substitutions and/or deletions and/or insertions; or the anti-FIX(a) antibody heavy chain CDR3 sequence identified by SEQ ID NO:60, optionally comprising 1, 2 or 3 amino acid substitutions and/or deletions and/or insertions, and the anti-FIX(a) antibody light chain CDR3 sequence identified by SEQ ID NO:64, optionally comprising 1, 2 or 3 amino acid substitutions and/or deletions and/or insertions, and the anti-FX(a) antibody heavy chain CDR3 sequence identified by SEQ ID NO:20, optionally comprising 1, 2 or 3 amino acid substitutions and/or deletions and/or insertions, and the anti-FX(a) antibody light chain CDR3 sequence identified by SEQ ID NO:24, optionally comprising 1, 2 or 3 amino acid substitutions and/or deletions and/or insertions; or the anti-FIX(a) antibody heavy chain CDR3 sequence identified by SEQ ID NO:60, optionally comprising 1, 2 or 3 amino acid substitutions and/or deletions and/or insertions, and the anti-FIX(a) antibody light chain CDR3 sequence identified by SEQ ID NO:64, optionally comprising 1, 2 or 3 amino acid substitutions and/or deletions and/or insertions, and the anti-FX(a) antibody heavy chain CDR3 sequence identified by SEQ ID NO:4, optionally comprising 1, 2 or 3 amino acid substitutions and/or deletions and/or insertions, and the anti-FX(a) antibody light chain CDR3 sequence identified by SEQ ID NO:8, optionally comprising 1, 2 or 3 amino acid substitutions and/or deletions and/or insertions; or the anti-FIX(a) antibody heavy chain CDR3 sequence identified by SEQ ID NO:68, optionally comprising 1, 2 or 3 amino acid substitutions and/or deletions and/or insertions, and the anti-FIX(a) antibody light chain CDR3 sequence identified by SEQ ID NO:72, optionally comprising 1, 2 or 3 amino acid substitutions and/or deletions and/or insertions, and the anti-FX(a) antibody heavy chain CDR3 sequence identified by SEQ ID NO:20, optionally comprising 1, 2 or 3 amino acid substitutions and/or deletions and/or insertions, and the anti-FX(a) antibody light chain CDR3 sequence identified by SEQ ID NO:24, optionally comprising 1, 2 or 3 amino acid substitutions and/or deletions and/or insertions; or the anti-FIX(a) antibody heavy chain CDR3 sequence identified by SEQ ID NO:68, optionally comprising 1, 2 or 3 amino acid substitutions and/or deletions and/or insertions, and the anti-FIX(a) antibody light chain CDR3 sequence identified by SEQ ID NO:72, optionally comprising 1, 2 or 3 amino acid substitutions and/or deletions and/or insertions, and the anti-FIX(a) antibody light chain CDR3 sequence identified by SEQ ID NO:4, optionally comprising 1, 2 or 3 amino acid substitutions and/or deletions and/or insertions and the anti-FX(a) antibody light chain CDR3 sequence identified by SEQ ID NO:8, optionally comprising 1, 2 or 3 amino acid substitutions and/or deletions and/or insertions; or the anti-FIX(a) antibody heavy chain CDR3 sequence identified by SEQ ID NO:76, optionally comprising 1, 2 or 3 amino acid substitutions and/or deletions and/or insertions, and the anti-FIX(a) antibody light chain CDR3 sequence identified by SEQ ID NO:80, optionally comprising 1, 2 or 3 amino acid substitutions and/or deletions and/or insertions, and the anti-FX(a) antibody heavy chain CDR3 sequence identified by SEQ ID NO:20, optionally comprising 1, 2 or 3 amino acid substitutions and/or deletions and/or insertions, and the anti-FX(a) antibody light chain CDR3 sequence identified by SEQ ID NO:24, optionally comprising 1, 2 or 3 amino acid substitutions and/or deletions and/or insertions; or the anti-FIX(a) antibody heavy chain CDR3 sequence identified by SEQ ID NO:76, optionally comprising 1, 2 or 3 amino acid substitutions and/or deletions and/or insertions, and the anti-FIX(a) antibody light chain CDR3 sequence identified by SEQ ID NO:80, optionally comprising 1, 2 or 3 amino acid substitutions and/or deletions and/or insertions, and the anti-FX(a) antibody heavy chain CDR3 sequence identified by SEQ ID NO:4, optionally comprising 1, 2 or 3 amino acid substitutions and/or deletions and/or insertions, and the anti-FX(a) antibody light chain CDR3 sequence identified by SEQ ID NO:8, optionally comprising 1, 2 or 3 amino acid substitutions and/or deletions and/or insertions; or the anti-FIX(a) antibody heavy chain CDR3 sequence identified by SEQ ID NO:84, optionally comprising 1, 2 or 3 amino acid substitutions and/or deletions and/or insertions, and the anti-FIX(a) antibody light chain CDR3 sequence identified by SEQ ID NO:88, optionally comprising 1, 2 or 3 amino acid substitutions and/or deletions and/or insertions, and the anti-FX(a) antibody heavy chain CDR3 sequence identified by SEQ ID NO:20, optionally comprising 1, 2 or 3 amino acid substitutions and/or deletions and/or insertions, and the anti-FX(a) antibody light chain CDR3 sequence identified by SEQ ID NO:24, optionally comprising 1, 2 or 3 amino acid substitutions and/or deletions and/or insertions; or the anti-FIX(a) antibody heavy chain CDR3 sequence identified by SEQ ID NO:84, optionally comprising 1, 2 or 3 amino acid substitutions and/or deletions and/or insertions, and the anti-FIX(a) antibody light chain CDR3 sequence identified by SEQ ID NO:88, optionally comprising 1, 2 or 3 amino acid substitutions and/or deletions and/or insertions, and the anti-FX(a) antibody heavy chain CDR3 sequence identified by SEQ ID NO:4, optionally comprising 1, 2 or 3 amino acid substitutions and/or deletions and/or insertions, and the anti-FX(a) antibody light chain CDR3 sequence identified by SEQ ID NO:8, optionally comprising 1, 2 or 3 amino acid substitutions and/or deletions and/or insertions.

14. The multispecific antibody or antigen-binding fragment thereof according to any of embodiments 9-13 comprising the anti-FIX(a) antibody heavy chain CDR1-3 sequences identified by SEQ ID NOs: 26, 27 and 28, respectively, optionally comprising 1, 2 or 3 amino acid substitutions and/or deletions and/or insertions, and the anti-FIX(a) antibody light chain CDR1-3 sequences identified by SEQ ID NOs: 30, 31 and 32, respectively, optionally comprising 1, 2 or 3 amino acid substitutions and/or deletions and/or insertions, and the anti-FX(a) antibody heavy chain CDR1-3 sequences identified by SEQ ID NOs: 18, 19 and 20, respectively, optionally comprising 1, 2 or 3 amino acid substitutions and/or deletions and/or insertions, and the anti-FX(a) antibody light chain CDR1-3 sequences identified by SEQ ID NOs: 22, 23 and 24, respectively, optionally comprising 1, 2 or 3 amino acid substitutions and/or deletions and/or insertions; or the anti-FIX(a) antibody heavy chain CDR1-3 sequences identified by SEQ ID NOs: 26, 27 and 28, respectively, optionally comprising 1, 2 or 3 amino acid substitutions and/or deletions and/or insertions, and the anti-FIX(a) antibody light chain CDR1-3 sequences identified by SEQ ID NOs: 30, 31 and 32, respectively, optionally comprising 1, 2 or 3 amino acid substitutions and/or deletions and/or insertions, and the anti-FX(a) antibody heavy chain CDR1-3 sequences identified by SEQ ID NOs: 2, 3 and 4, respectively, optionally comprising 1, 2 or 3 amino acid substitutions and/or deletions and/or insertions, and the anti-FX(a) antibody light chain CDR1-3 sequences identified by SEQ ID NOs: 6, 7 and 8, respectively, optionally comprising 1, 2 or 3 amino acid substitutions and/or deletions and/or insertions; or the anti-FIX(a) antibody heavy chain CDR1-3 sequences identified by SEQ ID NOs: 34, 35 and 36, respectively, optionally comprising 1, 2 or 3 amino acid substitutions and/or deletions and/or insertions, and the anti-FIX(a) antibody light chain CDR1-3 sequences identified by SEQ ID NOs: 38, 39 and 40, respectively, optionally comprising 1, 2 or 3 amino acid substitutions and/or deletions and/or insertions, and the anti-FX(a) antibody heavy chain CDR1-3 sequences identified by SEQ ID NOs: 18, 19 and 20, respectively, optionally comprising 1, 2 or 3 amino acid substitutions and/or deletions and/or insertions, and the anti-FX(a) antibody light chain CDR1-3 sequences identified by SEQ ID NOs: 22, 23 and 24, respectively, optionally comprising 1, 2 or 3 amino acid substitutions and/or deletions and/or insertions; or the anti-FIX(a) antibody heavy chain CDR1-3 sequences identified by SEQ ID NOs: 34, 35 and 36, respectively, optionally comprising 1, 2 or 3 amino acid substitutions and/or deletions and/or insertions, and the anti-FIX(a) antibody light chain CDR1-3 sequences identified by SEQ ID NOs: 38, 39 and 40, respectively, optionally comprising 1, 2 or 3 amino acid substitutions and/or deletions and/or insertions, and the anti-FX(a) antibody heavy chain CDR1-3 sequences identified by SEQ ID NOs: 2, 3 and 4, respectively, optionally comprising 1, 2 or 3 amino acid substitutions and/or deletions and/or insertions, and the anti-FX(a) antibody light chain CDR1-3 sequences identified by SEQ ID NOs: 6, 7 and 8, respectively, optionally comprising 1, 2 or 3 amino acid substitutions and/or deletions and/or insertions; or the anti-FIX(a) antibody heavy chain CDR1-3 sequences identified by SEQ ID NOs: 42, 43 and 44, respectively, optionally comprising 1, 2 or 3 amino acid substitutions and/or deletions and/or insertions, and the anti-FIX(a) antibody light chain CDR1-3 sequences identified by SEQ ID NOs: 46, 47 and 48, respectively, optionally comprising 1, 2 or 3 amino acid substitutions and/or deletions and/or insertions, and the anti-FX(a) antibody heavy chain CDR1-3 sequences identified by SEQ ID NOs: 18, 19 and 20, respectively, optionally comprising 1, 2 or 3 amino acid substitutions and/or deletions and/or insertions, and the anti-FX(a) antibody light chain CDR1-3 sequences identified by SEQ ID NOs: 22, 23 and 24, respectively, optionally comprising 1, 2 or 3 amino acid substitutions and/or deletions and/or insertions; or the anti-FIX(a) antibody heavy chain CDR1-3 sequences identified by SEQ ID NOs: 42, 43 and 44, respectively, optionally comprising 1, 2 or 3 amino acid substitutions and/or deletions and/or insertions, and the anti-FIX(a) antibody light chain CDR1-3 sequences identified by SEQ ID NOs: 46, 47 and 48, respectively, optionally comprising 1, 2 or 3 amino acid substitutions and/or deletions and/or insertions, and the anti-FX(a) antibody heavy chain CDR1-3 sequences identified by SEQ ID NOs: 2, 3 and 4, respectively, optionally comprising 1, 2 or 3 amino acid substitutions and/or deletions and/or insertions, and the anti-FX(a) antibody light chain CDR1-3 sequences identified by SEQ ID NOs: 6, 7 and 8, respectively, optionally comprising 1, 2 or 3 amino acid substitutions and/or deletions and/or insertions, or the anti-FIX(a) antibody heavy chain CDR1-3 sequences identified by SEQ ID NOs: 50, 51 and 52, respectively, optionally comprising 1, 2 or 3 amino acid substitutions and/or deletions and/or insertions, and the anti-FIX(a) antibody light chain CDR1-3 sequences identified by SEQ ID NOs: 54, 55 and 56, respectively, optionally comprising 1, 2 or 3 amino acid substitutions and/or deletions and/or insertions, and the anti-FX(a) antibody heavy chain CDR1-3 sequences identified by SEQ ID NOs: 18, 19 and 20, respectively, optionally comprising 1, 2 or 3 amino acid substitutions and/or deletions and/or insertions, and the anti-FX(a) antibody light chain CDR1-3 sequences identified by SEQ ID NOs: 22, 23 and 24, respectively, optionally comprising 1, 2 or 3 amino acid substitutions and/or deletions and/or insertions; or the anti-FIX(a) antibody heavy chain CDR1-3 sequences identified by SEQ ID NOs: 50, 51 and 52, respectively, optionally comprising 1, 2 or 3 amino acid substitutions and/or deletions and/or insertions, and the anti-FIX(a) antibody light chain CDR1-3 sequences identified by SEQ ID NOs: 54, 55 and 56, respectively, optionally comprising 1, 2 or 3 amino acid substitutions and/or deletions and/or insertions, and the anti-FX(a) antibody heavy chain CDR1-3 sequences identified by SEQ ID NOs: 2, 3 and 4, respectively, optionally comprising 1, 2 or 3 amino acid substitutions and/or deletions and/or insertions, and the anti-FX(a) antibody light chain CDR1-3 sequences identified by SEQ ID NOs: 6, 7 and 8, respectively, optionally comprising 1, 2 or 3 amino acid substitutions and/or deletions and/or insertions; or the anti-FIX(a) antibody heavy chain CDR1-3 sequences identified by SEQ ID NOs: 58, 59 and 60, respectively, optionally comprising 1, 2 or 3 amino acid substitutions and/or deletions and/or insertions, and the anti-FIX(a) antibody light chain CDR1-3 sequences identified by SEQ ID NOs: 62, 63 and 64, respectively, optionally comprising 1, 2 or 3 amino acid substitutions and/or deletions and/or insertions, and the anti-FX(a) antibody heavy chain CDR1-3 sequences identified by SEQ ID NOs: 18, 19 and 20, respectively, optionally comprising 1, 2 or 3 amino acid substitutions and/or deletions and/or insertions, and the anti-FX(a) antibody light chain CDR1-3 sequences identified by SEQ ID NOs: 22, 23 and 24, respectively, optionally comprising 1, 2 or 3 amino acid substitutions and/or deletions and/or insertions; or the anti-FIX(a) antibody heavy chain CDR1-3 sequences identified by SEQ ID NOs: 58, 59 and 60, respectively, optionally comprising 1, 2 or 3 amino acid substitutions and/or deletions and/or insertions, and the anti-FIX(a) antibody light chain CDR1-3 sequences identified by SEQ ID NOs: 62, 63 and 64, respectively, optionally comprising 1, 2 or 3 amino acid substitutions and/or deletions and/or insertions, and the anti-FX(a) antibody heavy chain CDR1-3 sequences identified by SEQ ID NOs: 2, 3 and 4, respectively, optionally comprising 1, 2 or 3 amino acid substitutions and/or deletions and/or insertions, and the anti-FX(a) antibody light chain CDR1-3 sequences identified by SEQ ID NOs: 6, 7 and 8, respectively, optionally comprising 1, 2 or 3 amino acid substitutions and/or deletions and/or insertions; or the anti-FIX(a) antibody heavy chain CDR1-3 sequences identified by SEQ ID NOs: 66, 67 and 68, respectively, optionally comprising 1, 2 or 3 amino acid substitutions and/or deletions and/or insertions, and the anti-FIX(a) antibody light chain CDR1-3 sequences identified by SEQ ID NOs: 70, 71 and 72, respectively, optionally comprising 1, 2 or 3 amino acid substitutions and/or deletions and/or insertions, and the anti-FX(a) antibody heavy chain CDR1-3 sequences identified by SEQ ID NOs: 18, 19 and 20, respectively, optionally comprising 1, 2 or 3 amino acid substitutions and/or deletions and/or insertions, and the anti-FX(a) antibody light chain CDR1-3 sequences identified by SEQ ID NOs: 22, 23 and 24, respectively, optionally comprising 1, 2 or 3 amino acid substitutions and/or deletions and/or insertions; or the anti-FIX(a) antibody heavy chain CDR1-3 sequences identified by SEQ ID NOs: 66, 67 and 68, respectively, optionally comprising 1, 2 or 3 amino acid substitutions and/or deletions and/or insertions, and the anti-FIX(a) antibody light chain CDR1-3 sequences identified by SEQ ID NOs: 70, 71 and 72, respectively, optionally comprising 1, 2 or 3 amino acid substitutions and/or deletions and/or insertions, and the anti-FX(a) antibody heavy chain CDR1-3 sequences identified by SEQ ID NOs: 2, 3 and 4, respectively, optionally comprising 1, 2 or 3 amino acid substitutions and/or deletions and/or insertions, and the anti-FX(a) antibody light chain CDR1-3 sequences identified by SEQ ID NOs: 6, 7 and 8, respectively, optionally comprising 1, 2 or 3 amino acid substitutions and/or deletions and/or insertions; or the anti-FIX(a) antibody heavy chain CDR1-3 sequences identified by SEQ ID NOs: 74, 75 and 76, respectively, optionally comprising 1, 2 or 3 amino acid substitutions and/or deletions and/or insertions, and the anti-FIX(a) antibody light chain CDR1-3 sequences identified by SEQ ID NOs: 78, 79 and 80, respectively, optionally comprising 1, 2 or 3 amino acid substitutions and/or deletions and/or insertions, and the anti-FX(a) antibody heavy chain CDR1-3 sequences identified by SEQ ID NOs: 18, 19 and 20, respectively, optionally comprising 1, 2 or 3 amino acid substitutions and/or deletions and/or insertions, and the anti-FX(a) antibody light chain CDR1-3 sequences identified by SEQ ID NOs: 22, 23 and 24, respectively, optionally comprising 1, 2 or 3 amino acid substitutions and/or deletions and/or insertions; or the anti-FIX(a) antibody heavy chain CDR1-3 sequences identified by SEQ ID NOs: 74, 75 and 76, respectively, optionally comprising 1, 2 or 3 amino acid substitutions and/or deletions and/or insertions, and the anti-FIX(a) antibody light chain CDR1-3 sequences identified by SEQ ID NOs: 78, 79 and 80, respectively, optionally comprising 1, 2 or 3 amino acid substitutions and/or deletions and/or insertions, and the anti-FX(a) antibody heavy chain CDR1-3 sequences identified by SEQ ID NOs: 2, 3 and 4, respectively, optionally comprising 1, 2 or 3 amino acid substitutions and/or deletions and/or insertions, and the anti-FX(a) antibody light chain CDR1-3 sequences identified by SEQ ID NOs: 6, 7 and 8, respectively, optionally comprising 1, 2 or 3 amino acid substitutions and/or deletions and/or insertions; or the anti-FIX(a) antibody heavy chain CDR1-3 sequences identified by SEQ ID NOs: 82, 83 and 84, respectively, optionally comprising 1, 2 or 3 amino acid substitutions and/or deletions and/or insertions, and the anti-FIX(a) antibody light chain CDR1-3 sequences identified by SEQ ID NOs: 86, 87 and 88, respectively, optionally comprising 1, 2 or 3 amino acid substitutions and/or deletions and/or insertions, and the anti-FX(a) antibody heavy chain CDR1-3 sequences identified by SEQ ID NOs: 18, 19 and 20, respectively, optionally comprising 1, 2 or 3 amino acid substitutions and/or deletions and/or insertions, and the anti-FX(a) antibody light chain CDR1-3 sequences identified by SEQ ID NOs: 22, 23 and 24, respectively, optionally comprising 1, 2 or 3 amino acid substitutions and/or deletions and/or insertions; or the anti-FIX(a) antibody heavy chain CDR1-3 sequences identified by SEQ ID NOs: 82, 83 and 84, respectively, optionally comprising 1, 2 or 3 amino acid substitutions and/or deletions and/or insertions, and the anti-FIX(a) antibody light chain CDR1-3 sequences identified by SEQ ID NOs: 86, 87 and 88, respectively, optionally comprising 1, 2 or 3 amino acid substitutions and/or deletions and/or insertions, and the anti-FX(a) antibody heavy chain CDR1-3 sequences identified by SEQ ID NOs: 2, 3 and 4, respectively, optionally comprising 1, 2 or 3 amino acid substitutions and/or deletions and/or insertions, and the anti-FX(a) antibody light chain CDR1-3 sequences identified by SEQ ID NOs: 6, 7 and 8, respectively, optionally comprising 1, 2 or 3 amino acid substitutions and/or deletions and/or insertions.

15. The multispecific antibody or antigen-binding fragment thereof according to embodiment 14 wherein the antibody is a bispecific antibody capable of specifically binding FIX(a) and FX(a) wherein the binding domains are those of the mAb pairs consisting of:

mAb1/mAbA, mAb2/mAbA, mAb3/mAbA, mAb4/mAbA, mAb5/mAbA, mAb6/mAbA, mAb7/mAbA, mAb8/mAbA, mAb1/mAbB, mAb2/mAbB, mAb3/mAbB, mAb4/mAbB, mAb5/mAbB, mAb6/mAbB, mAb7/mAbB or mAb8/mAbB.

16. The multispecific antibody or antigen-binding fragment thereof according to any of embodiments 9-15 wherein the antibody or antigen-binding fragment thereof is a procoagulant antibody.

17. The multispecific antibody or antigen-binding fragment thereof according to any of embodiments 9-16 wherein the antibody or antigen-binding fragment thereof is capable of increasing the enzymatic activity of FIXa towards FX.

18. The multispecific antibody or antigen-binding fragment thereof according to any of embodiments 9-17 wherein the antibody or antigen-binding fragment thereof is capable of functionally substituting for FVIII and/or FVIIIa.

19. The multispecific antibody or antigen-binding fragment thereof according to any of embodiments 9-18 wherein the antibody or antigen-binding fragment thereof is a bispecific antibody.

20. The antibody according to any of the previous embodiments wherein the antibody isotype is IgG1, IgG2, IgG3 or IgG4 or a combination thereof such an antibody comprising an IgG1 $F_c$ region and a IgG4 $F_c$ region, and optionally comprising 1 or 2 substitution(s) in the $C_H3$ domain.

21. A pharmaceutical composition comprising an antibody or antigen-binding fragment thereof according to any of the previous embodiments and optionally one or more pharmaceutically acceptable carrier(s).
22. The pharmaceutical composition comprising an antibody or antigen-binding fragment thereof according to embodiment 21 for use in the treatment of a coagulopathy or blood coagulation disorder, such as haemophilia A with or without inhibitors.
23. The antibody or antigen-binding fragment thereof or composition according to any of the previous embodiments for use in a method of treatment of a coagulopathy or blood coagulation disorder, such as on demand or prophylactic treatment.
24. The antibody or antigen-binding fragment thereof or composition according to any of the previous embodiments for use in the treatment of haemophilia A with or without inhibitors, such as on demand or prophylactic treatment.
25. A method of treating a subject suffering from a coagulopathy or blood coagulation disorder, comprising administering to said subject an antibody or antigen-binding fragment thereof or composition according to any of the previous embodiments.
26. A method according to embodiment 25 wherein the coagulopathy or blood coagulation disorder is haemophilia A or haemophilia A with inhibitors.
27. Use of an antibody or antigen-binding fragment thereof or composition according to any of embodiments 1-20 for the manufacture of a medicament for use in the treatment of a subject in need thereof, such as on demand or prophylactic treatment.
28. Use of an antibody or antigen-binding fragment thereof or composition according to any of embodiments 1-21 for the manufacture of a medicament for use in the treatment of haemophilia A with or without inhibitors, such as on demand or prophylactic treatment.
29. A eukaryotic cell which expresses the antibody or antigen-binding fragment thereof, according to any of embodiments 1-20.
30. A kit comprising the antibody or antigen-binding fragment thereof or composition according to any of embodiments 1-21 and instructions for use.
31. The antibody or antigen-binding fragment thereof according to any of embodiments 1-8 wherein the antibody or antigen-binding fragment thereof is a component (intermediate) for use in a multispecific antibody, such as a procoagulant bispecific antibody.
32. The antibody or antigen-binding fragment thereof according to any of embodiments 1-8 wherein the antibody or antigen-binding fragment thereof is a component (intermediate) for use in the manufacture of a multispecific antibody, such as a procoagulant bispecific antibody.
33. The multispecific antibody or antigen-binding fragment thereof according to any of embodiments 9-20, such as a procoagulant bispecific antibody, wherein the procoagulant activity of said antibody is improved over the multispecific antibodies disclosed in WO2018/141863 and WO2019/065795.
34. The multispecific antibody or antigen-binding fragment thereof according to embodiment 33 wherein said improvement is determined using an assay as disclosed herein, such as in a HA-PPP TGT assay (as described in example 7 herein).
35. The multispecific antibody or antigen-binding fragment thereof according to any of embodiment 9-20 wherein said antibody or antigen-binding fragment thereof is capable of providing a mean peak thrombin (in nM) of
    a) at least 80, 81, 82, 83, 84, 95, 86, 87, 88, 89, 90, 91, 92, 93, 94, 95, 96, 97, 98, 99 100, 101, 102, 103, 104, 105, 106, 107, 108, 109 or 110 when using tissue factor as trigger, or
    b) at least 350, 355, 360, 365, 370, 375, 380, 385 or 390 when using FXIa as trigger, at a compound concentration of 700 nM in a TGT assay (in HA-PPP) according to example 7 herein.
36. The multispecific antibody or antigen-binding fragment thereof according to any of embodiments 9-20 wherein said antibody or antigen-binding fragment thereof has an equivalent FVIII activity as determined according to Example 8 herein which is improved over emicizumab and the multispecific antibodies disclosed in WO2018/141863 and WO2019/065795 (both of which are incorporated herein by reference).
37. The antibody according to any of embodiments 9-20 wherein the antibody isotype is IgG4, optionally comprising 1 or 2 substitutions in one $C_H3$ domain.
38. An injection device comprising an antibody or antigen-binding fragment thereof or composition according to any of embodiments 9-20.
39. The injection device according to embodiment 38 wherein said device is a disposable and/or pre-filled and/or multi-dose device, such as a pen.
40. The injection device according to embodiment 39 wherein said device is a pre-filled pen.
41. The injection device according to embodiment 39-40 wherein said device is a multi-dose pen.
42. The injection device according to any of embodiments 38-41 wherein said injection device comprises a tube having a needle gauge of 20 to 36.
43. The multispecific antibody or antigen-binding fragment thereof according to embodiment 13 or 14 wherein the substitution is a conservative substitution.

In one embodiment the multispecific antibodies, such as bispecific antibodies, of the invention do not interfere with the effect of FVIII, such as recombinant FVIII administered to a patient suffering from haemophilia A, when said antibodies are used in clinically relevant dosages in the treatment of haemophilia A.

In one embodiment an antibody or antigen-binding fragment thereof of the invention when present at 43.64 μg/mL plasma, in a patient suffering from haemophilia A, corresponds to at least 20-50, such as 20-40, such as 25-35, such as at least 20, 21, 22, 23, 24, 25, 26, 27, 28, 29, 30, 31, 32, 33, 34, 35, 36, 37, 38, 39 or 40 IU of equivalent factor VIII activity per decilitre plasma.

In one embodiment an antibody or antigen-binding fragment thereof of the invention when present at 30 μg/mL plasma, in a patient suffering from haemophilia A, corresponds to at least 10-50, such as 15-40, such as 15-30, such as 15-20, such as at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 IU of equivalent factor VIII activity per decilitre plasma.

In one embodiment an antibody or antigen-binding fragment thereof of the invention when present at 15 μg/mL plasma, in a patient suffering from haemophilia A, corresponds to at least 10-50, such as 15-40, such as 15-30, such as 15-20, such as at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 IU of equivalent factor VIII activity per decilitre plasma.

In one embodiment an antibody or antigen-binding fragment thereof of the invention has reduced immunogenicity as compared to procoagulant antibodies of the art.

In one embodiment an antibody or antigen-binding fragment thereof of the invention are used for prophylactic treatment of haemophilia A with or without inhibitors.

In one embodiment an antibody or antigen-binding fragment thereof of the invention are capable of stimulating the enzymatic activity of FIXa towards FX.

In one embodiment an anti-FIX(a) antibody or antigen-binding fragment thereof as listed in example 6 table 2 are capable of stimulating the enzymatic activity of FIXa towards FX.

In a preferred embodiment antibodies of the invention have the IgG4/kappa format, optionally comprising one or more substitutions in the Fc the constant region(s).

The heavy chain constant domain regions ($C_H1$-$C_H2$-$C_H3$) were for the anti-FIX(a) arm human IgG4 with a S228P (EU-numbering) substitution and with truncation of the C-terminal lysine:

```
                                     (SEQ ID NO: 91)
ASTKGPSVFPLAPCSRSTSESTAALGCLVKDYFPEPVTVSWNSGA

LTSGVHTFPAVLQSSGLYSLSSVVTVPSSSLGTKTYTCNVDHKPS

NTKVDKRVESKYGPPCPPCPAPEFLGGPSVFLFPPKPKDTLMISR

TPEVTCVVVDVSQEDPEVQFNWYVDGVEVHNAKTKPREEQFNSTY

RVVSVLTVLHQDWLNGKEYKCKVSNKGLPSSIEKTISKAKGQPRE

PQVYTLPPSQEEMTKNQVSLTCLVKGFYPSDIAVEWESNGQPENN

YKTTPPVLDSDGSFFLYSRLTVDKSRWQEGNVFSCSVMHEALHNH

YTQKSLSLSLG.
```

In one embodiment the heavy chain constant domain regions ($C_H1$-$C_H2$-$C_H3$) were for the anti-FX(a) arm human IgG4 with the S228P substitution and with two additional substitutions, F405L and R409K (EU numbering), in the $C_H3$ domain to facilitate hetero-dimerization of the heavy chains (described in example 4) and with truncation of the C-terminal lysine:

```
                                     (SEQ ID NO: 92)
ASTKGPSVFPLAPCSRSTSESTAALGCLVKDYFPEPVTVSWNSGA

LTSGVHTFPAVLQSSGLYSLSSVVTVPSSSLGTKTYTCNVDHKPS

NTKVDKRVESKYGPPCPPCPAPEFLGGPSVFLFPPKPKDTLMISR

TPEVTCVVDVSQEDPEVQFNWYVDGVEVHNAKTKPREEQFNSTYR

VVSVLTVLHQDWLNGKEYKCKVSNKGLPSSIEKTISKAKGQPREP

QVYTLPPSQEEMTKNQVSLTCLVKGFYPSDIAVEWESNGQPENNY

KTTPPVLDSDGSFLLYSKLTVDKSRWQEGNVFSCSVMHEALHNHY

TQKSLSLSLG.
```

and, the light chain constant region ($C_L$) was human kappa:

```
                                     (SEQ ID NO: 93)
RTVAAPSVFIFPPSDEQLKSGTASVVCLLNNFYPREAKVQWKVDN

ALQSGNSQESVTEQDSKDSTYSLSSTLTLSKADYEKHKVYACEVT

HQGLSSPVTKSFNRGEC.
```

In another embodiment antibodies can also be expressed in the IgG4 format with heavy chain constant domain regions ($C_H1$-$C_H2$-$C_H3$) for the anti-FIX(a) arm carrying S228P, F405L and R409K substitutions and with heavy chain constant domain regions for the anti-FX(a) arm carrying the S228P substitution, with or without C-terminal lysine deletion.

In one embodiment antibodies can also be expressed in the IgG1/kappa format. In that case the heavy chain constant domain regions of the anti-FIX(a) arm is human IgG1 F405L with truncation of the C-terminal lysine:

```
                                     (SEQ ID NO: 94)
ASTKGPSVFPLAPSSKSTSGGTAALGCLVKDYFPEPVTVSWNSGA

LTSGVHTFPAVLQSSGLYSLSSVVTVPSSSLGTQTYICNVNHKPS

NTKVDKKVEPKSCDKTHTCPPCPAPELLGGPSVFLFPPKPKDTLM

ISRTPEVTCVVVDVSHEDPEVKFNWYVDGVEVHNAKTKPREEQYN

STYRWSVLTVLHQDWLNGKEYKCKVSNKALPAPIEKTISKAKGQP

REPQVYTLPPSRDELTKNQVSLTCLVKGFYPSDIAVEWESNGQPE

NNYKTTPPVLDSDGSFLLYSKLTVDKSRWQQGNVFSCSVMHEALH

NHYTQKSLSLSPG.
```

and the heavy chain constant domain regions of the anti-FX(a) arm is human IgG1 K409R with truncation of the C-terminal lysine:

```
                                     (SEQ ID NO: 95)
ASTKGPSVFPLAPSSKSTSGGTAALGCLVKDYFPEPVTVSWNSGA

LTSGVHTFPAVLQSSGLYSLSSVVTVPSSSLGTQTYICNVNHKPS

NTKVDKKVEPKSCDKTHTCPPCPAPELLGGPSVFLFPPKPKDTLM

ISRTPEVTCVVVDVSHEDPEVKFNWYVDGVEVHNAKTKPREEQYN

STYRWSVLTVLHQDWLNGKEYKCKVSNKALPAPIEKTISKAKGQP

REPQVYTLPPSRDELTKNQVSLTCLVKGFYPSDIAVEWESNGQPE

NNYKTTPPVLDSDGSFFLYSRLTVDKSRWQQGNVFSCSVMHEALH

NHYTQKSLSLSPG.
```

Antibodies can also be expressed in the IgG1 format with heavy chain constant domain regions ($C_H1$-$C_H2$-$C_H3$) for the anti-FIX(a) arm carrying the K409R substitution and with heavy chain constant domain regions for the anti-FX(a) arm carrying the F405L substitution, with or without C-terminal lysine deletion.

The constant domain regions may further comprise additional substitutions or other modifications e.g. to modulate effector functions, half-life or other properties.

In one embodiment, the potency of bispecific antibodies capable of binding to FIX(a) and FX(a), such as—but not limited to—those disclose herein, may be determined in a chromogenic potency assay comprising a) human Factor X, lyophilized in presence of a fibrin polymerization inhibitor, b) human Factor IXa, c) human thrombin, d) calcium and e) synthetic phospholipids, f) a chromogenic substrate, specific for Factor Xa (SXa-11) (Hyphen Biomed) and the anti-FIX/anti-FX bispecific antibody to be assessed. For any dilutions suitable buffers such as Tris-BSA can be used. In such assay, the level of FX activation is dependent on the potency of the bispecific antibody. Activated FX (FXa) hydrolyses the chromogenic substrate whereby pNA is released allowing for a photospectometric readout at 405 nm (e.g. using a Tecan Sunrise ELISA reader). The readout is dependent on FXa concentration and thus proportional to the potency of the bispecific antibody being tested. A bispecific reference antibody with a pre-determined potency should be included.

The present disclosure also provides kits that comprise antibodies or antigen-binding fragments thereof as disclosed herein suitable for treatment as described herein. In some embodiments, a kit comprises (i) an antibody, such as a bispecific antibody or antigen-binding fragment thereof or pharmaceutical compositions as disclosed herein, or encoding nucleic acids or vectors, or a combination thereof, and (ii) instructions for use. A skilled person will readily recognize that the antibodies, bispecific molecules (e.g., bispecific antibodies) and pharmaceutical compositions as disclosed herein or the encoding nucleic acids or vectors, or a combination thereof can be readily incorporated into one of the established kit formats which are well-known in the art.

All references, including publications, patent applications and patents, cited herein are hereby incorporated by reference to the same extent as if each reference was individually and specifically indicated to be incorporated by reference and was set forth in its entirety herein

EXAMPLES

List of Abbreviations

ACN: Acetonitrile
bimAb: Bispecific monoclonal Antibody
CDR: Complementarity Determining Region
LC-MS Liquid chromatography-mass spectrometry
FACS: Fluorescence-activated cell sorting
FIX: Coagulation Factor IX
FIXa: Coagulation Factor IXa
FX: Coagulation Factor X
FXa: Coagulation Factor Xa
HA: Haemophilia A
HA-PPP: HA-induced human platelet-poor plasma
hFIXa: human Coagulation Factor IXa
HPLC: High Performance Liquid Chromatography
mAb: monoclonal Antibody
MACS: Magnetic-activated cell sorting
PCR: Polymerase Chain Reaction
SEC: Size Exclusion Chromatography
SIA: Sequence Identical Analogue
SPR: Surface Plasmon Resonance

Example 1: Development of Anti-FIX(a) and Anti-FX(a) Antibodies

FIX(a) and FX(a) binding antibodies as disclosed herein were identified using various antibody development methods. In order to generate a diverse set of antibodies, immunisations of mice and rabbits were performed and phage display and Adimab yeast antibody expression platforms were also utilized.

Adimab Yeast Antibody Platform

The Adimab platform is a yeast antibody expression system encompassing a fully human naïve IgG1/kappa library with a diversity of 1010. The antibody selection process was directed using MACS and FACS based methods which allowed monitoring of applied selection criteria in real time. Since selections were based on MACS and FACS, labelled antigens (e.g. biotin) were needed. Selection campaigns were performed using biotin-labelled active-site inhibited hFIXa (FIXa-EGR-biotin), or antibody mediated immobilization of hFIXa. Hits were evaluated for binding using Bio-layer interferometry (Octet fortebio systems).

Phage Display

The utilized antibody phage display platform is a proprietary fully human Fab display library. The library has a size of 1010 and was constructed by a combinational approach utilizing chemical synthesis of the light chain, as well as the heavy chain CDR1 and CDR2, complemented with PCR amplification of the heavy chain CDR3 from human peripheral blood mononuclear cells. To maximise epitope diversity, different panning strategies were explored, including panning using biotinylated FIXa-EGR, FX, active-site inhibited FXa, or antigen capture using anti-FIXa antibodies. Initial hits were identified by phage ELISA. After sequence analysis, unique hits were cloned and recombinantly expressed as IgG1 antibodies, and ranked using SPR (Biacore) or Bio-layer interferometry (Octet fortebio systems).

In Vivo Platforms

Mice and rabbits were used for the generation of antibodies using in vivo platforms. For the generation of anti-FIX/FIXa antibodies, mice or rabbits were immunized with human FIXa, FIXa-EGR or FIX using standard protocols. The spleen cells from mice were fused with myeloma cells using standard techniques and the resulting antibody containing hybridoma supernatants were screened for binding to FIXa using ELISA. FIXa binding rabbit B-cells were single cell sorted using FACS by gating on cells binding randomly biotinylated FIXa-EGR (detected by streptavidin conjugated fluorophore). Sorted rabbit B cells were cultured for seven days in 384w plates using feeder cells and conditioned medium from splenocytes, prior to screening against FIXa in ELISA. Rabbit B-cells and mouse hybridoma clones, expressing FIXa binding antibody hits, were either used for VH/VL sequencing followed by recombinant expression (for rabbit or hybridoma mAbs) or further propagated for mAb production (mouse hybridomas).

For the generation of anti-FX antibodies, mice and rabbits were immunised with FX using standard protocols. Rabbit B-cells were isolated by FACS based single-cell sorting and using randomly biotinylated FX (detected by streptavidin conjugated flourophore) while spleen cells from immunized mice were used for standard hybridoma development. Resulting antibody producing B-cell or mouse hybridoma clones were screened for FX binding using ELISA and Octet fortebio systems. Rabbit B-cell or mouse hybridoma clones expressing antibody hits were either used for VH/VL sequencing followed by recombinant expression (for rabbit or hybridoma mAbs) or further propagated for mAb production (mouse hybridomas).

Sequencing of Hybridoma-Derived Antibodies

Anti-FIXa and anti-FX antibody producing hybridomas were sequenced and expressed in HEK293 cells using standard techniques. Expressed antibodies were evaluated for antigen binding using Octet fortebio systems.

Total RNA was extracted from antibody producing clones and the variable domain ($V_H$ and $V_L$) encoding DNA sequences were amplified using RT-PCR. $V_H$ and $V_L$ sequences were determined and inserted into a pTT-based mammalian expression vector (Durocher et al (2002) Nucleic Acid Res. 30: E9) or into a pcDNA3.4 mammalian expression vector (Invitrogen) containing antibody constant region encoding DNA sequences. For PTT/pcDNA3.4 mAb expression vectors, the $V_H$ and $V_L$ DNA sequences were inserted in-frame with human IgG1 or IgG4 S228P ($C_H1C_H2C_H3$, optionally with additional amino acid substitutions and deletions, e.g. substitutions in the $C_H3$ domain and deletion of the C-terminal lysine) or human $C_L$ kappa constant region encoding DNA sequences, respectively. For the corresponding pTT/pcDNA3.4 Fab expression vectors the $V_H$ DNA sequences were inserted in-frame with human IgG4 $C_H1$ encoding DNA sequences.

Example 2: Recombinant Expression of Antibodies and Antibody Fab Fragments

Antibodies and antibody Fab fragments were expressed using transient transfection of HEK293 suspension cells (293Expi, Invitrogen) essentially following manufacturer's instructions. 293Expi cells were typically subcultivated every 3-4 days in Expi293F expression medium (Invitrogen, catalogue number A1435104) supplemented with 1% P/S (GIBCO catalogue number 15140-122). Expi293F cells were transfected at a cell density of 2.5-3 mill/mL using Expifectamine. For each litre of Expi293F cells, the transfection was performed by diluting a total of 1 mg of plasmid DNA ($V_H$-$C_H1$ (for Fab) or $V_H$-$C_H1$-$C_H2$-$C_H3$ (for mAb) and LC plasmids in 1:1 ratio) into 50 mL Optimem (GIBCO, cat. no. 51985-026, dilution A) and by diluting 2.7 mL Expifectamine into 50 mL Optimem (dilution B). For Fab and mAb producing co-transfections, $V_H$-$C_H1$ and LC plasmids (Fab) and $V_H$-$C_H1$-$C_H2$-$C_H3$ and LC plasmids (mAb), respectively, were used in a 1:1 ratio. Dilution A and B were mixed and incubated at room temperature for 10-20 minutes. The transfection mix was hereafter added to the Expi293F cells and cells were incubated at 37° C. in a humidified incubator with orbital rotation (85-125 rpm). One day post-transfection, transfected cells were supplemented with 5 ml of ExpiFectamine 293 Transfection Enhancer 1 and 50 ml of ExpiFectamine 293 Transfection Enhancer 2. Cell culture supernatants were typically harvested 4-5 days post-transfection by centrifugation followed by filtration.

Example 3: Fab and Antibody Purification and Characterization

All purification steps were carried out at 4° C. For lab scale, Milli-Q water was used for buffer preparation. The HPLC system used for SE-HPLC analysis was Aglient 1100. Aggregation and LC/MS were assessed for QC.

Capturing of Fab was performed with HiTrap Protein G HP affinity chromatography with binding buffer in 1×PBS (10 mM $Na_2HPO_4$, 1.8 mM $KH_2PO_4$, 137 mM NaCl, 2.7 mM KCl), pH 7.4. One step elution was performed with 0.1M Glycine, pH 2.8. The final product was desalted via 52 mL GE Hiprep 16 desalting column into formulation buffer (25 mM HEPES, 150 mM NaCl) with pH 7.4 and concentrated by centrifugal ultrafilter (30 KD C.O.) for storage at −80° C.

To assess the quality of the purified Fab, SDS-PAGE and high-performance size-exclusion chromatography (SE-HPLC) analysis were performed. Batches that did not meet the quality standards (e.g., <95% monomeric by SE-HPLC) were further purified by size-exclusion chromatography. LC/MS was carried out to verify identity of Fab protein. Molecular weights (MWs) of all Fab's were shown to be consistent with theoretical MW of heavy chain and light chain, respectively.

Antibody Purification and Characterization

Purification of the antibodies was conducted by affinity chromatography using a Protein A MabSelect SuRe resins (GE Healthcare, cat. no. 17-5438-01). For small-scale antibody productions, protein A based purification was performed in 96 well plates while for larger productions, the ÄktaExplorer chromatography system (GE Healthcare, cat. no. 18-1112-41) was used. The buffer systems used for the affinity purification step were 1) an equilibration buffer composed of 20 mM NaPhosphate pH 7.2, 150 mM NaCl and 2) an elution buffer composed of 10 mM Formic acid pH 3.5 and 3) a pH-adjustment buffer composed of 0.4 μM NaPhosphate pH 9.0. Cell supernatants were applied directly without any adjustments onto a pre-equilibrated MabSelect SuRe column. The column was washed with approximately 10 column volumes of equilibration buffer and the antibodies were eluted isocratically in approx. 2-5 column volume of elution buffer. The pH of the pooled fractions was adjusted to neutral using the described pH-adjustment buffer immediately after elution.

The purified antibodies were characterized using different methods such as SDS-PAGE/Coomassie, size-exclusion high-pressure liquid-chromatography (SE-HPLC) and liquid-chromatography mass spectrometry (LC-MS) analyses. The SDS-PAGE/Coomassie analysis was performed using NuPage 4-12% Bis-Tris gels (Invitrogen, cat. no. NP0321BOX). Here, all antibodies displayed expected light chain and heavy chain components. Intact molecular mass determinations were performed using a Liquid Chromatography Electrospray Ionisation Time-of-Flight Mass Spectrometry method setup on an Agilent 6210 instrument and a desalting column MassPREP (Waters, cat. no. USRM10008656). The buffer system used was an equilibration buffer composed of 0.1% Formic acid in LC-MS graded-$H_2O$ and an elution buffer composed of 0.1% formic acid in LC-MS graded-ACN. Analyses were performed with and without N-Glycosidase F (Roche Diagnostics, cat. no. 11365177001) and reducing agent (i.e. mercaptoethanol or DTT). All antibodies displayed expected intact molecular masses in accordance with sequence and one heavy chain N-glycan. Purity was determined based on SE-HPLC. The final protein purity was analysed based on SE-HPLC method setup on an Agilent LC 1100/1200 system and using a BIOSep-SEC-S3000 300×7.8 mm column (Phenomenex, cat. no. 00H-2146-K0) and a running buffer composed of 200 mM NaPhosphate pH 6.9, 300 mM NaCl and 10% isopropanol. UV280 and fluorescence (Ex 280 nm/Em 354 nm) detectors was used for detection. The antibodies eluted as single symmetric peaks with retention times reflecting the size of the antibodies. Purity estimates were all between 95-99% for the different antibodies. To measure the final protein concentrations, a NanoDrop spectrophotometer (Thermo Scientific) was used together with specific extinction coefficients for each of the antibodies.

Example 4: Bispecific Antibodies Prepared by In Vitro Assembly

Bispecific antibodies were generated by in vitro assembly of a first and a second antibody by the Duobody® method (Genmab) described (Labrijn et al. *PNAS* 2013, vol. 110, pp. 5145-5150) for bispecific human IgG1 antibodies and using a slightly modified variant for bispecific human IgG4 antibodies as detailed in the following.

For IgG1 the heavy chain constant region of the first antibody is human IgG1 K409R (anti-FIX/FIXa) and the heavy chain constant region of the second antibody is human IgG1 F405L (anti-FX/FXa). The IgG1 may be a IgG1 variant with reduced effector functions, as referred to earlier.

For human IgG4, the heavy chain constant region of the first antibody is IgG4 S228P (anti-FIX/FIXa) and the heavy chain constant region of the second antibody is IgG4 S228P F405L+R409K (anti-FX). The two parental antibodies are produced as described in Examples 1-3. The Fab arm exchange reaction is carried out in HEPES buffer (pH 7.4) under reducing conditions using 75 mM 2-mercaptoethylamine (2-MEA) and incubation at 30° C. for 4 hours.

Example 5: Preparation of Monovalent (One-Armed) Antibodies

To avoid any potential avidity effects associated with conventional monospecific and bivalent antibodies, e.g. in FXa generation assays (Example 9), a monovalent one-armed (OA) antibody format was used, as described by Martens et al.: A Novel One-Armed Anti-c-Met Antibody Inhibits Glioblastoma Growth In vivo. *Clin. Cancer Res.* 12, 6144-6152 (2006), where a full heavy chain, a truncated heavy chain (lacking the Fab region) and a light chain are co-expressed. Instead of co-expression of the three chains described by Martens et al. monovalent antibodies of the present invention were prepared using the Duobody® principle as described for bispecific antibodies (Example 4). Thus, monovalent antibodies were prepared by mixing a full monospecific and bivalent antibody and a truncated heavy chain dimer (formally derived from a full antibody by removing the Fab region) and allow exchange of chains to proceed under the same experimental conditions as described in Example 4. Formation of the monovalent antibody requires that the antibody and truncated heavy chain dimer carry appropriate complementary mutations to promote hetero-dimerization, i.e. F405L/K409R for human IgG1 and F405L+R409K/WT for human IgG4, as described in Example 4.

In case of monovalent antibodies of the IgG1 subtype the truncation of the heavy chain can be from the N-terminus to a position in-between Cys 220 and the upper hinge Cys 226 (EU numbering). A specific example of a truncated human IgG1 heavy chain is one where residues 1-220 are truncated.

In case of monovalent antibodies of the human IgG4 subtype the truncation of the heavy chain can be from the N-terminus to a position in-between Cys 200 and the upper hinge Cys 226 (EU numbering). A specific example of a truncated human IgG4 heavy chain is one where residues 1-214 are truncated.

Example 6: Overview of Bispecific Antibody (Component) IDs and SEQ ID NOS

TABLE 1

Overview of bispecific antibody components and corresponding VH/VL SEQ ID NOs

| BimAb ID | Component anti-FIX(a) antibody: mAb ID | Component anti-FIX(a) antibody: VH SEQ ID NO \| VL SEQ ID NO | Component anti-FX(a) antibody: mAb ID | Component anti-FX(a) antibody: VH SEQ ID NO \| VL SEQ ID NO |
|---|---|---|---|---|
| bimAb6B | mAb6 | 65\|69 | mAbB | 17\|21 |
| bimAb5B | mAb5 | 57\|61 | mAbB | 17\|21 |
| bimAb4B | mAb4 | 49\|53 | mAbB | 17\|21 |
| bimAb3B | mAb3 | 41\|45 | mAbB | 17\|21 |
| bimAb2B | mAb2 | 33\|37 | mAbB | 17\|21 |
| bimAb1B | mAb1 | 25\|29 | mAbB | 17\|21 |
| bimAb8B | mAb8 | 81\|85 | mAbB | 17\|21 |
| bimAb7B | mAb7 | 73\|77 | mAbB | 17\|21 |
| bimAb1A | mAb1 | 25\|29 | mAbA | 1\|5 |
| bimAb2A | mAb2 | 33\|37 | mAbA | 1\|5 |
| bimAb3A | mAb3 | 41\|45 | mAbA | 1\|5 |
| bimAb4A | mAb4 | 49\|53 | mAbA | 1\|5 |
| bimAb5A | mAb5 | 57\|61 | mAbA | 1\|5 |
| bimAb6A | mAb6 | 65\|69 | mAbA | 1\|5 |
| bimAb7A | mAb7 | 73\|77 | mAbA | 1\|5 |
| bimAb8A | mAb8 | 81\|85 | mAbA | 1\|5 |

TABLE 2

Overview of anti-FIX(a) antibody VH, VL and CDR sequences ('#' represents SEQ ID NO)

| mAb ID | VH/VL Domain | Sequence | # | CDR1 Sequence | # | CDR2 Sequence | # | CDR3 Sequence | # |
|---|---|---|---|---|---|---|---|---|---|
| mAb1 | VH | EVQLVESGGGLVQPGRSLRLSCAASGFTFHDYAMHWVRQVPGKGLEWVSGISWRGDIGGYVKSVKGRFTISRDNAKNSLYLQMNSLRAEDTALYYCVKSYGSGSFYNAFDSWGQGTLVTVSS | 25 | DYAMH | 26 | GISWRGDIGGYVKSVKG | 27 | SYGSGSFYNAFDS | 28 |
| mAb1 | VL | DIQMTQSPSTLSASVGDRVTITCRASQSISSWLAWYQQKPGKAPKFLIYKGSKADRGTPSRFSGSGSGTEFTLTISSLQPDDFATYYCLEYESYIRTFGQGTKVEIK | 29 | RASQSISSWLA | 30 | KGSKADR | 31 | LEYESYIRT | 32 |
| mAb2 | VH | EVQLVESGGGLVQPGRSLRLSCAASGFTFHDYAMHWVRQVPGKGLEWVSGISWRGDIGGYVKSVKGRFTISRDNAKNSLYLQMNSLRAEDTALYYCVKSYGSGSFYNAFDSWGQGTLVTVSS | 33 | DYAMH | 34 | GISWRGDIGGYVKSVKG | 35 | SYGSGSFYNAFDS | 36 |

TABLE 2-continued

Overview of anti-FIX(a) antibody VH, VL and CDR sequences ('#' represents SEQ ID NO)

| mAb ID | VH/VL Domain | Sequence | # | CDR1 Sequence | # | CDR2 Sequence | # | CDR3 Sequence | # |
|---|---|---|---|---|---|---|---|---|---|
| mAb2 | VL | DIQMTQSPSTLSASVGDR VTITCRASQSISSWLAWY QQKPGKAPKFLIYKGSKQ DRGTPSRFSGSGSGTEF TLTISSLQPDDFATYYCLE YSSYIRTFGQGTKVEIK | 37 | RASQSISSW LA | 38 | KGSKQDR | 39 | LEYSSYIRT | 40 |
| mAb3 | VH | EVQLVESGGGLVQPGRS LRLSCAASGFTFHDYAMH WVRQVPGKGLEWVSGIS WRGDIGGYVKSVKGRFTI SRDNAKNSLYLQMNSLR AEDTALYYCVKSYGSGSF YNAFDSWGQGTLVTVSS | 41 | DYAMH | 42 | GISWRGDIG GYVKSVKG | 43 | SYGSGSFY NAFDS | 44 |
| mAb3 | VL | DIQMTQSPSTLSASVGDR VTITCRASQSISSWLAWY QQKPGKAPKFLIYKGSKT DRGTPSRFSGSGSGTEF TLTISSLQPDDFATYYCLE YESYIRTFGQGTKVEIK | 45 | RASQSISSW LA | 46 | KGSKTDR | 47 | LEYESYIRT | 48 |
| mAb4 | VH | EVQLVESGGGLVQPGRS LRLSCAASGFTFHDYAMH WVRQVPGKGLEWVSGIS WRGDIGGYVKSVKGRFTI SRDNAKNSLYLQMNSLR AEDTALYYCVKSYGSGSF YNAFDSWGQGTLVTVSS | 49 | DYAMH | 50 | GISWRGDIG GYVKSVKG | 51 | SYGSGSF YNAFDS | 52 |
| mAb4 | VL | DIQMTQSPSTLSASVGDR VTITCRASQSISSWLAWY QQKPGKAPKFLIYKSEKL DRGTPSRFSGSGSGTEF TLTISSLQPDDFATYYCLE YESYIRTFGQGTKVEIK | 53 | RASQSISSW LA | 54 | KSEKLDR | 55 | LEYESYIRT | 56 |
| mAb5 | VH | EVQLVESGGGLVQPGRS LRLSCAASGFTFHDYAMH WVRQVPGKGLEWVSGIS WRGDIGGYVKSVKGRFTI SRDNAKNSLYLQMNSLR AEDTALYYCVKSYGSGSF YNAFDSWGQGTLVTVSS | 57 | DYAMH | 58 | GISWRGDIG GYVKSVKG | 59 | SYGSGSF YNAFDS | 60 |
| mAb5 | VL | DIQMTQSPSTLSASVGDE VTITCRASQSISSWLAWY QQKPGKAPKFLIYKGEKL DRGTPSRFSGSGSGTEF TLTISSLQPDDFATYYCLE YSSYIRTFGQGTKVEIK | 61 | RASQSISSW LA | 62 | KGEKLDR | 63 | LEYSSYIRT | 64 |
| mAb6 | VH | EVQLVESGGGLVQPGRS LRLSCAASGFTFHDYAMH WVRQVPGKGLEWVSGIS WRGDIGGYVKSVKGRFTI SRDNAKNSLYLQMNSLR AEDTALYYCVKSYGSGSF YNAFDSWGQGTLVTVSS | 65 | DYAMH | 66 | GISWRGDIG GYVKSVKG | 67 | SYGSGSF YNAFDS | 68 |
| mAb6 | VL | DIQMTQSPSTLSASVGDE VTITCRASQSISSWLAWY QQKPGKAPKFLIYKGSKL DRGTPSRFSGSGSGTEF TLTISSLQPDDFATYYCLE YSSYIRTFGQGTKVEIK | 69 | RASQSISSW LA | 70 | KGSKLDR | 71 | LEYSSYIRT | 72 |
| mAb7 | VH | EVQLVESGGGLVQPGRS LRLSCAASGFTFHDYAMH WVRQVPGKGLEWVSGIS WRGDIGGYVKSVKGRFTI SRDNAKNSLYLQMNSLR AEDTALYYCVKSYGSGSF YNAFDSWGQGTLVTVSS | 73 | DYAMH | 74 | GISWRGDIG GYVKSVKG | 75 | SYGSGSFYN AFDS | 76 |

TABLE 2-continued

Overview of anti-FIX(a) antibody VH, VL and CDR sequences ('#' represents SEQ ID NO)

| mAb ID | VH/VL Domain | Sequence | # | CDR1 Sequence | # | CDR2 Sequence | # | CDR3 Sequence | # |
|---|---|---|---|---|---|---|---|---|---|
| mAb7 | VL | DIQMTQSPSTLSASVGDE VTITCRASQSISSWLAWY QQKPGKAPKFLIYKAEKL DRGTPSRFSGSGSGTEF TLTISSLQPDDFATYYCLE YESYIRTFGQGTKVEIK | 77 | RASQSISSW LA | 78 | KAEKLDR | 79 | LEYESYIRT | 80 |
| mAb8 | VH | EVQLVESGGGLVQPGRS LRLSCAASGFTFHDYAMH WVRQVPGKGLEWVSGIS WRGDIGGYVKSVKGRFTI SRDNAKNSLYLQMNSLR AEDTALYYCVKSYGSGSF YNAFDSWGQGTLVTVSS | 81 | DYAMH | 82 | GISWRGDIG GYVKSVKG | 83 | SYGSGSFY NAFDS | 84 |
| mAb8 | VL | DIQMTQSPSTLSASVGDR VTITCRASQSISSWLAWY QQKPGKAPKFLIYKAEKL DRGTPSRFSGSGSGTEF TLTISSLQPDDFATYYCLE YESYIRTFGQGTKVEIK | 85 | RASQSISSW LA | 86 | KAEKLDR | 87 | LEYESYIRT | 88 |

TABLE 3

Overview of anti-FX(a) antibody VH, VL and CDR sequences ('#' represents SEQ ID NO)

| mAb ID | VH/VL Domain | Sequence | # | CDR1 Sequence | # | CDR2 Sequence | # | CDR3 Sequence | # |
|---|---|---|---|---|---|---|---|---|---|
| mAbA | VH | EVQLVQSGAEVKKPGES LRISCKGSGYSFSTSWIV WVRQMPGKGLEWMGMI DPSDSFTSYSPSFQGHV TISADKSISTAYLQWSSLK ASDTAMYYCARLHYYNS EEFDVWGQGTLVTVSS | 1 | TSWIV | 2 | MIDPSDSF TSYSPSFQ G | 3 | LHYYNS EEFDV | 4 |
| mAbA | VL | EIVLTQSPGTLSLSPGER ATLSCRASQSVSSSYLA WYQQKPGQAPRLLIYGQ SSRTRGIPDRFSGSGSG TDFTLTISRLEPEDFAVYY CQQFGDSQLFTFGQGTK LEIK | 5 | RASQSVSSS YLA | 6 | GQSSRTR | 7 | QQFGDS QLFT | 8 |
| mAbB | VH | EVQLVQSGAEVKKPGES LRISCKGSGYSFSTSWIV WVRQMPGKGLEWMGMI DPSDSYTSYSPSFQGHV TISADKSISTAYLQWSSLK ASDTAMYYCARLHYYNS EEFDVWGQGTMVTVSS | 17 | TSWIV | 18 | MIDPSDSY TSYSPSFQ G | 19 | LHYYNS EEFDV | 20 |
| mAbB | VL | EIVLTQSPGTLSLSPGER ATLSCRASQSVSSSYLA WYQQKPGQAPRLLIYGQ SSRTRGIPDRFSGSGSG TDFTLTISRLEPEDFAVYY CQQFGESQLFTFGQGTK LEIK | 21 | RASQSVSSS YLA | 22 | GQSSRTR | 23 | QQFGE SQLFT | 24 |

Example 7: Activity of Bispecific Anti-FIX(a)/FX(a) Antibodies in a Thrombin Generation Test (TGT) in Human Haemophilia A-Like Platelet-Poor Plasma The procoagulant activity of the bispecific antibodies bimAb6B, bimAb5B, bimAb4B, bimAb3B, bimAb2B, bimAb1B, bimAb8B, bimAb7B, bimAb1A, bimAb2A, bimAb3A, bimAb4A, bimAb5A, bimAb6A, bimAb7A and bimAb8A were determined based on their ability to promote thrombin generation in the presence of procoagulant synthetic phospholipid membrane according to the principles described by Hemker et al. (Pathophysiology. An emicizumab sequence identical analogue (SIA) was included for comparison. Each bispecific antibody (test compound) was tested in a thrombin generation test (TGT) using normal human platelet-poor plasma (NHP) supplemented with neutralizing anti-FVIII polyclonal antibody (hereafter named HA-PPP).

Materials and Methods

Thrombin Generation Test

Thrombin generation tests (TGT) in NHP (from healthy volunteers) supplemented with sheep anti-human FVIII polyclonal antibody (pAb, Haematologic Technologies Inc., VT, USA) were performed by standard calibrated automated thrombography using a 96-well plate fluorometer (Fluoroscan Ascent FL, Thermolabsystems, Helsinki, Finland). Reaction mixtures contained 36 μl NHP preincubated with 0.1 μg/ml anti-FVIII pAb, 4 μl test compound dilution (diluted in 20 mM HEPES, 140 mM NaCl, pH 7.4, 2% BSA), 10 μl of either 1 μM tissue factor (TF, pppLow, from Thrombinoscope BV, Maastricht, The Netherlands) or 8.3 U/ml human factor XIa (Enzyme Research Laboratories, IN, USA) and 10 μl FluCa Substrate (Thrombinoscope BV, Maastricht, The Netherlands). The TGT was calibrated using Thrombin calibrator (Thrombinoscope BV, Maastricht, The Netherlands), where 10 μl Thrombin calibrator was mixes with 36 μl NHP preincubated with 0.1 μg/ml anti-FVIII pAb, 4 μl buffer (20 mM HEPES, 140 mM NaCl, pH 7.4, 2% BSA). TGT was performed at eight concentrations of test compound (0.32, 0.96, 2.88, 8.64, 25.9, 77, 233, and 700 nM, final plasma concentration) or added buffer (20 mM HEPES, 140 mM NaCl, pH 7.4, 2% BSA) only (representing HA control). The concentration ranges were tested in at least three independent experiments in HA-PPP from the same stock. Normal control levels in TGT were measured using NHP added buffer (20 mM HEPES, 140 mM NaCl, pH 7.4, 2% BSA) only. The TGT was allowed to proceed for a total of 60 minutes and the TGT parameter Peak Thrombin Height (nM) was analysed by Thrombinoscope software (Thrombinoscope BV).

Results and Discussion

Tables 4 and 5 show the measured peak thrombin generation rates for each bispecific antibody at the concentrations tested in HA-PPP trigger with tissue factor and human FXIa, respectively. The data show that all test compounds increase the peak thrombin formation above the level observed in the absence of antibody, i.e. exhibit procoagulant activity. In addition, bimAb6B, bimAb5B, bimAb4B, bimAb3B, bimAb2B, bimAb1B, bimAb8B, bimAb1A, bimAb2A, bimAb3A, bimAb4A, bimAb5A, bimAb6A and bimAb8A all exhibits higher concentration-dependent thrombin generation rates than that observed for emicizumab SIA when bimAb concentration was above 8.64 nM and 1 μM tissue factor trigger was used, demonstrating superior potency. bimAb7B was superior to emicizumab SIA between 2.88 and 233 nM bimAb.

Furthermore, bimAb6B, bimAb5B, bimAb4B, bimAb3B, bimAb2B, bimAb1B, bimAb8B, bimAb7B, bimAb1A, bimAb2A, bimAb3A, bimAb4A, bimAb5A, bimAb6A, bimAb7A and bimAb8A all exhibit higher thrombin generation potential than observed for emicizumab SIA at all tested concentrations when triggering coagulation with 8.3 mU/IL human FXIa.

TABLE 4

Thrombin generation test (TGT) in HA-PPP triggered with tissue factor
Thrombin generation test (TGT) of the bispecific antibodies bimAb6B, bimAb5B, bimAb4B, bimAb3B, bimAb2B, bimAb1B, bimAb8B, bimAb7B, bimAb1A, bimAb2A, bimAb3A, bimAb4A, bimAb5A, bimAb6A, bimAb7A and bimAb8A were tested in induced haemophilia A plasmas (HA-PPP) triggered with human tissue factor (pppLow). Mean peak thrombin generation levels ± standard deviation measured at each of the tested compound concentrations in at least three independent experiments in HA-PPP. Standard deviation is omitted if a measurement was discarded due to poor data quality.

| | Mean ± SD in nM | | | | | | | |
|---|---|---|---|---|---|---|---|---|
| | 0.32 nM bimAb | 0.96 nM bimAb | 2.88 nM bimAb | 8.64 nM bimAb | 25.9 nM bimAb | 77 nM bimAb | 233 nM bimAb | 700 nM bimAb |
| emicizumab SIA | 11.757 ± 0.804 | 12.295 ± 0.918 | 12.7 ± 0.603 | 12.52 ± 0.474 | 13.638 ± 2.087 | 16.412 ± 3.234 | 20.095 ± 4.591 | 25.935 ± 8.212 |
| bimAb6B | 12.297 ± 0.616 | 12.19 ± 0.37 | 13.84 ± 0.49 | 21.7 ± 4.313 | 54.19 ± 28.595 | 62.643 ± 6.386 | 85.773 ± 2.413 | 87.52 ± 4.908 |
| bimAb5B | 12.187 ± 0.777 | 13.287 ± 1.174 | 14.179 ± 0.639 | 19.925 ± 0.997 | 36.995 ± 1.336 | 64.863 ± 5.259 | 92.925 ± 12.099 | 85.235 ± 4.66 |
| bimAb4B | 14.697 ± 3.43 | 14.08 ± 0.442 | 16.013 ± 0.351 | 22.49 ± 0.042 | 43.363 ± 1.777 | 74.563 ± 2.706 | 96.837 ± 1.035 | 141.16 ± 68.837 |
| bimAb3B | 12.167 ± 0.46 | 13.263 ± 1.223 | 15.67 ± 0.858 | 22.43 ± 1.117 | 51.313 ± 19.507 | 76.197 ± 7.939 | 98.673 ± 5.969 | 101.293 ± 5.679 |
| bimAb2B | 12.57 ± 0.661 | 13.01 ± 0.815 | 15.493 ± 1.262 | 18.97 ± 0.905 | 36.905 ± 6.993 | 64.173 ± 2.873 | 100.657 ± 38.835 | 97.54 ± 8.809 |
| bimAb1B | 12.7 ± 0.315 | 13.357 ± 1.066 | 14.587 ± 0.954 | 20.79 ± 2.517 | 35.595 ± 0.587 | 59.197 ± 1.2 | 81.197 ± 0.432 | 82.06 ± 5.523 |
| bimAb8B | 13.153 ± 0.435 | 13.693 ± 0.713 | 17.163 ± 2.405 | 23.575 ± 4.589 | 38.303 ± 1.483 | 67.56 ± 0.336 | 86.605 ± 3.684 | 91.21 ± 3.734 |

TABLE 4-continued

Thrombin generation test (TGT) in HA-PPP triggered with tissue factor
Thrombin generation test (TGT) of the bispecific antibodies bimAb6B, bimAb5B, bimAb4B, bimAb3B, bimAb2B, bimAb1B, bimAb8B, bimAb7B, bimAb1A, bimAb2A, bimAb3A, bimAb4A, bimAb5A, bimAb6A, bimAb7A and bimAb8A were tested in induced haemophilia A plasmas (HA-PPP) triggered with human tissue factor (pppLow). Mean peak thrombin generation levels ± standard deviation measured at each of the tested compound concentrations in at least three independent experiments in HA-PPP. Standard deviation is omitted if a measurement was discarded due to poor data quality.

| | Mean ± SD in nM | | | | | | | |
|---|---|---|---|---|---|---|---|---|
| | 0.32 nM bimAb | 0.96 nM bimAb | 2.88 nM bimAb | 8.64 nM bimAb | 25.9 nM bimAb | 77 nM bimAb | 233 nM bimAb | 700 nM bimAb |
| bimAb7B | 12.607 ± 1.241 | 13.1 ± 0.735 | 20.573 ± 4.276 | 20.3 ± 2.249 | 38.9 ± 2.927 | 72.2 ± 10.063 | 93.117 ± 8.994 | 65.567 ± 45.288 |
| bimAb1A | 12.653 ± 0.242 | 15.157 ± 1.086 | 18.645 ± 2.185 | 52.83 ± 15.076 | 54.77 ± 12.106 | 76.857 ± 9.861 | 100.007 ± 13.953 | 108.323 ± 20.072 |
| bimAb2A | 12.567 ± 0.941 | 14.237 ± 0.395 | 16.99 ± 0.014 | 20.13 ± 2.515 | 48.38 | 76.78 ± 8.905 | 90.003 ± 3.125 | 99.303 ± 7.73 |
| bimAb3A | 13.163 ± 0.66 | 14.677 ± 0.95 | 15.28 | 35.93 ± 13.52 | 73.965 ± 11.109 | 82.467 ± 16.114 | 100.403 ± 5.612 | 102.367 ± 12.884 |
| bimAb4A | 12.93 ± 0.877 | 17.795 ± 2.468 | 18.98 | 34.64 ± 8.966 | 64.81 ± 0.933 | 82.927 ± 9.592 | 106.087 ± 4.06 | 108.72 ± 6.408 |
| bimAb5A | 12.843 ± 0.746 | 13.96 ± 0.728 | 16.32 | 26.42 | 36.61 | 77.427 ± 15.045 | 108.677 ± 7.963 | 97.06 ± 8.499 |
| bimAb6A | 12.503 ± 0.672 | 15.885 ± 3.924 | 15.083 ± 0.974 | 21.69 ± 0.997 | 39.717 ± 6.457 | 70.787 ± 10.296 | 92.307 ± 8.908 | 97.267 ± 5.801 |
| bimAb7A | 12.807 ± 0.649 | 14.36 ± 0.386 | 16.86 | 30.103 ± 7.234 | 50.81 ± 6.449 | 62.723 ± 44.24 | 68.013 ± 47.923 | 75.483 ± 55.161 |
| bimAb8A | 12.687 ± 0.717 | 14.98 ± 0.832 | 19.66 ± 1.527 | 31.81 ± 7.891 | 73.195 ± 27.57 | 86.44 ± 11.112 | 112.02 ± 7.889 | 114.757 ± 8.234 |

TABLE 5

Thrombin generation test (TGT) in HA-PPP triggered with human FXIa
Thrombin generation test (TGT) of the bispecific antibodies bimAb6B, bimAb5B, bimAb4B, bimAb3B, bimAb2B, bimAb1B, bimAb8B, bimAb7B, bimAb1A, bimAb2A, bimAb3A, bimAb4A, bimAb5A, bimAb6A, bimAb7A and bimAb8A were tested in induced haemophilia A plasmas (HA-PPP) triggered with human factor XIa (FXIa). Mean peak thrombin generation levels ± standard deviation measured at each of the tested compound concentrations in at least three independent experiments in HA-PPP.

| | Mean ± SD in nM | | | | | | | |
|---|---|---|---|---|---|---|---|---|
| | 0.32 nM bimAb | 0.96 nM bimAb | 2.88 nM bimAb | 8.64 nM bimAb | 25.9 nM bimAb | 77 nM bimAb | 233 nM bimAb | 700 nM bimAb |
| emicizumab SIA | 12.525 ± 0.078 | 28.98 ± 4.192 | 61.46 ± 10.318 | 104.27 ± 9.919 | 166.36 ± 15.498 | 219.627 ± 17.738 | 259.522 ± 18.304 | 301.968 ± 12.363 |
| bimAb6B | 83.78 ± 11.929 | 129.657 ± 14.848 | 180.823 ± 8.564 | 231.533 ± 13.804 | 283.75 ± 11.562 | 331.267 ± 12.757 | 353.323 ± 14.897 | 361.26 ± 16.757 |
| bimAb5B | 89.943 ± 13.608 | 136.033 ± 11.417 | 179.673 ± 8.294 | 230.817 ± 13.731 | 281.1 ± 11.174 | 316.283 ± 12.008 | 346.78 ± 14.804 | 350.21 ± 8.887 |
| bimAb4B | 100.687 ± 2.706 | 153.22 ± 6.189 | 208.257 ± 6.214 | 251.857 ± 5.284 | 302.89 ± 8.495 | 337.387 ± 10.372 | 358.493 ± 13.78 | 365.033 ± 21.438 |
| bimAb3B | 99.523 ± 9.208 | 151.67 ± 0.417 | 202.377 ± 3.045 | 251.38 ± 18.415 | 301.857 ± 19.307 | 338.097 ± 23.138 | 357.743 ± 24.169 | 379.673 ± 14.326 |
| bimAb2B | 83.153 ± 4.214 | 135.03 ± 7.345 | 183.667 ± 10.355 | 228.707 ± 3.131 | 281.627 ± 12.507 | 322.93 ± 16.787 | 349.877 ± 17.96 | 357.703 ± 13.882 |
| bimAb1B | 89.61 ± 1.615 | 139.6 ± 9.428 | 198.657 ± 10.553 | 239.44 ± 3.052 | 290.56 ± 10.469 | 328.903 ± 22.423 | 343.56 ± 18.137 | 350.76 ± 17.533 |
| bimAb8B | 94.04 ± 6.112 | 149.267 ± 4.531 | 196.313 ± 13.3 | 238.94 ± 7.088 | 297.757 ± 1.024 | 335.59 ± 11.946 | 349.247 ± 6.836 | 362.773 ± 17.255 |
| bimAb7B | 101.23 ± 2.884 | 154.61 ± 12.642 | 206.82 ± 9.014 | 247.543 ± 10.334 | 308.45 ± 17.045 | 338.807 ± 16.747 | 361.917 ± 17.368 | 354.6 ± 1.612 |
| bimAb1A | 98.1 ± 6.291 | 152.817 ± 14.063 | 201.567 ± 18.383 | 248.71 ± 15.142 | 295.157 ± 19.277 | 333.927 ± 23.675 | 354.703 ± 17.593 | 380.45 ± 26.151 |
| bimAb2A | 88.515 ± 12.495 | 136.583 ± 10.702 | 185.413 ± 12.825 | 225.327 ± 14.225 | 276.897 ± 9.791 | 318.21 ± 16.657 | 339.887 ± 15.865 | 361.7 ± 3.882 |
| bimAb3A | 100.27 ± 15.641 | 157.333 ± 20.291 | 210.063 ± 19.272 | 248.093 ± 22.251 | 304.703 ± 22.452 | 344.15 ± 24.814 | 365.073 ± 24.443 | 381.857 ± 27.939 |
| bimAb4A | 109.493 ± 22.37 | 162.417 ± 24.775 | 216.673 ± 25.138 | 256.993 ± 26.534 | 310.857 ± 25.345 | 350.563 ± 26.038 | 369.607 ± 15.477 | 375.2 ± 22.209 |
| bimAb5A | 90.753 ± 13.161 | 137.513 ± 9.09 | 185.11 ± 8.402 | 235.28 ± 15.43 | 284.483 ± 23.557 | 324.417 ± 23.098 | 350.543 ± 23.502 | 358.47 ± 14.292 |

TABLE 5-continued

Thrombin generation test (TGT) in HA-PPP triggered with human FXIa
Thrombin generation test (TGT) of the bispecific antibodies bimAb6B, bimAb5B, bimAb4B, bimAb3B, bimAb2B, bimAb1B, bimAb8B, bimAb7B, bimAb1A, bimAb2A, bimAb3A, bimAb4A, bimAb5A, bimAb6A, bimAb7A and bimAb8A were tested in induced haemophilia A plasmas (HA-PPP) triggered with human factor XIa (FXIa). Mean peak thrombin generation levels ± standard deviation measured at each of the tested compound concentrations in at least three independent experiments in HA-PPP.

| | Mean ± SD in nM | | | | | | | |
|---|---|---|---|---|---|---|---|---|
| | 0.32 nM bimAb | 0.96 nM bimAb | 2.88 nM bimAb | 8.64 nM bimAb | 25.9 nM bimAb | 77 nM bimAb | 233 nM bimAb | 700 nM bimAb |
| bimAb6A | 90.497 ± 21.308 | 139.677 ± 18.024 | 180.807 ± 15.901 | 233.057 ± 26.276 | 276.047 ± 22.223 | 320.073 ± 28.67 | 343.383 ± 18.583 | 355.823 ± 15.235 |
| bimAb7A | 130.47 ± 28.242 | 184.4 ± 23.109 | 231.67 ± 25.266 | 273.803 ± 30.982 | 324.84 ± 12.898 | 367.083 ± 22.996 | 373.353 ± 18.066 | 388.523 ± 10.901 |
| bimAb8A | 101.767 ± 15.815 | 148.277 ± 13.37 | 199.86 ± 14.783 | 240.503 ± 12.784 | 292.173 ± 9.706 | 333.24 ± 10.464 | 354.79 ± 8.803 | 375.083 ± 16.98 |

Example 8: Equivalent FVIII Activity of Bispecific Antibodies

To estimate the equivalent FVIII activity of bimAbs in vitro, a plasma-based Thrombin generation assay was established to allow for a broad dose response for recombinant, B-domain truncated FVIII between 1 and 100 IU/dL using the peak Thrombin levels. The dose response curve for recombinant, B-domain truncated FVIII is used as standard curve for analysis of the Thrombin generation from bimAbs to estimate equivalent FVIII activity.

Method:

Thrombin generation was measured as described in Example 7, however using 1 U/ml human factor XIa (Enzyme Research Laboratories, IN, USA) as trigger. In addition, an 8-point dilution series of recombinant, B-domain truncated FVIII (NovoEight, Novo Nordisk A/S) from 100 IU/dL and two-fold downwards was included as a FVIII standard curve.

Determination of FVIII Equivalent Activity of Bispecific Antibodies:

Dose-response data for recombinant, B-domain truncated FVIII was fitted to "[Agonist] vs. response (three parameters)" (Eq. 1) using the non-linear analysis function of GraphPad Prism version 8.0.2:

$$\text{Peak thrombin} = \text{Bottom} + [FVIII] * (\text{Top} - \text{Bottom})/(EC50 + [FVIII]). \quad \text{Eq. 1}$$

where [FVIII] is the FVIII concentration in IU/mL, EC50 is the concentration of FVIII that gives 50% activity, Bottom and Top are the plateaus of the fit.

By solving for [FVIII], the modified equation (Eq. 2) can be used to estimate the concentration of FVIII which generates the same thrombin peak as a particular bispecific antibody:

$$[FVIII] = -EC50 * \frac{(Y - \text{Bottom})}{(Y - \text{Top})}. \quad \text{Eq. 2}$$

where Y is the measured peak thrombin.

Results:

A non-linear fit of FVIII dose-response curve yields the following constants: EC50=20.3±2.73, Top=476±18.7 and Bottom=−22.6±10.1. Using Eq. 2 the equivalent FVIII activity is estimated for the bispecific antibodies described in Example 6, see Table 6 below.

TABLE 6

Equivalent FVIII activity of bispecific antibodies.
Estimated FVIII equivalent activity of bimAbs tested at four different bimAb concentration (10, 30, 100 and 300 nM, corresponding to 1.45, 4.36, 14.55 and 43.64 μg/mL, respectively).
Results in FVIII equivalents (IU/dL) are stated as mean ± SD (n = 3).

| Bispecific mAb | 10 nM bimAb | 30 nM bimAb | 100 nM bimAb | 300 nM bimAb |
|---|---|---|---|---|
| bimAb1A | 7.62 ± 0.30 IU/dL | 13.73 ± 0.43 IU/dL | 22.00 ± 2.06 IU/dL | 28.45 ± 2.60 IU/dL |
| bimAb2A | 6.93 ± 0.47 IU/dL | 12.03 ± 0.44 IU/dL | 20.51 ± 0.53 IU/dL | 26.22 ± 2.71 IU/dL |
| bimAb3A | 9.03 ± 0.48 IU/dL | 14.69 ± 0.92 IU/dL | 24.33 ± 1.46 IU/dL | 30.83 ± 2.32 IU/dL |
| bimAb4A | 9.29 ± 0.28 IU/dL | 16.16 ± 1.04 IU/dL | 26.27 ± 2.44 IU/dL | 32.51 ± 4.11 IU/dL |
| bimAb5A | 7.53 ± 0.35 IU/dL | 13.54 ± 0.84 IU/dL | 22.08 ± 1.54 IU/dL | 28.23 ± 2.41 IU/dL |
| bimAb6A | 6.77 ± 0.19 IU/dL | 12.40 ± 0.70 IU/dL | 20.66 ± 1.73 IU/dL | 27.21 ± 2.41 IU/dL |
| bimAb7A | 8.76 ± 0.52 IU/dL | 15.35 ± 1.18 IU/dL | 24.41 ± 2.44 IU/dL | 30.75 ± 3.60 IU/dL |
| bimAb8A | 9.50 ± 1.09 IU/dL | 15.82 ± 1.22 IU/dL | 25.09 ± 2.28 IU/dL | 33.01 ± 3.91 IU/dL |
| bimAb1B | 7.01 ± 0.48 IU/dL | 12.74 ± 0.70 IU/dL | 21.07 ± 1.83 IU/dL | 29.68 ± 2.53 IU/dL |
| bimAb2B | 6.98 ± 0.57 IU/dL | 11.70 ± 0.37 IU/dL | 19.53 ± 0.58 IU/dL | 28.46 ± 1.12 IU/dL |
| bimAb3B | 8.13 ± 0.38 IU/dL | 14.72 ± 1.14 IU/dL | 24.61 ± 1.17 IU/dL | 33.95 ± 4.28 IU/dL |
| bimAb4B | 8.55 ± 0.48 IU/dL | 15.39 ± 1.08 IU/dL | 26.41 ± 3.37 IU/dL | 34.60 ± 4.61 IU/dL |
| bimAb5B | 6.67 ± 0.38 IU/dL | 12.64 ± 0.50 IU/dL | 22.56 ± 2.21 IU/dL | 28.35 ± 3.05 IU/dL |
| bimAb6B | 6.21 ± 0.31 IU/dL | 11.58 ± 0.60 IU/dL | 19.95 ± 1.12 IU/dL | 28.18 ± 1.98 IU/dL |
| bimAb7B | 8.51 ± 0.81 IU/dL | 14.74 ± 1.44 IU/dL | 23.47 ± 2.10 IU/dL | 32.40 ± 4.93 IU/dL |
| bimAb8B | 8.27 ± 0.54 IU/dL | 15.07 ± 1.27 IU/dL | 25.58 ± 2.28 IU/dL | 34.84 ± 3.61 IU/dL |

Example 9: Activity of Monovalent Anti-FIX(a) Antibodies in a FXa Generation Assay To avoid any potential avidity effects arising as a consequence of the bivalency of the conventional IgG antibody format, the stimulatory activity of anti-FIX(a) antibodies on FIXa enzymatic activity towards FX was determined following reformatting into a monovalent one-armed (OA) antibody format (Example 5). Tested antibodies are listed in Table 7 below. The monovalent OA versions of the anti-FIXa antibody ACE910 were included for comparison. The stimulatory activity of OA antibodies was measured in assay buffer (50 mM HEPES, 100 mM NaCl, 5 mM CaCl2, 0.1% (w/v) PEG8000, pH 7.3+1 mg/ml BSA) at fixed concentrations of phosphatidyl serine (PS): phosphatidyl choline (PC) phospholipid vesicles (final concentration of 500 µM; Haematologic Technologies Inc, USA) and plasma-derived FIXa (final concentrations of 0.025 or 0.1 nM; Haematologic Technologies Inc, USA). The concentration of FIXa was chosen to ensure that less than 15% of the substrate FX was converted into FXa. Following pre-incubation in the presence of monovalent OA antibody (final concentrations listed in Table 7), 100 nM plasma-derived FX (Haematologic Technologies Inc, USA) was added to give a final reaction volume of 50 µl, and activation was allowed to proceed for 20 min at room temperature. The reaction was then quenched by addition of 25 µl quench buffer (50 mM HEPES, 100 mM NaCl, 60 mM EDTA, 0.1% PEG8000, pH 7.3+1 mg/ml BSA) and the amount of FXa generated was determined by further addition of 25 µl 2 mM S-2765 chromogenic substrate (Chromogenix, Sweden) and measurement of chromogenic substrate conversion by absorbance measurement at 405 nm (AOD/min) in a microplate reader. The measured activity was corrected for background activity by subtraction of the signal measured in the same assay but with FIXa and antibody replaced by assay buffer, and then normalized according to the concentration of FIXa present in the assay ([FIXa] total). Dividing this number by the similarly normalized rate of FXa generation in the absence of antibody (AFIXa.norm), an antibody stimulation index was calculated providing the fold stimulation of FIXa activity by the antibody at the concentration used. Due to slow rate of FXa generation by free FIXa, activation reactions in the absence of antibody were carried out as described above but with 5, 10, or 20 nM FIXa present. Measured activities were then background subtracted and normalized according to the FIXa concentration in the assay. For the calculation of the stimulation index, the average of the three normalized activities of free FIXa was used.

Determination of Stimulation Index

In summary, calculation of the stimulation index can be described as follows $$\text{Stimulation index} = \left((A_{FIXa+OA} - A_{bckg})/[FIXa]_{total}\right)/A_{FIXa,norm} \quad \text{Eq. 3}$$

where $A_{FIXa+OA}$ is the activity measured in the presence of OA antibody, $A_{bckg}$ is the background activity measured in the absence of FIXa and OA antibody, $[FIXa]_{total}$ is the FIXa concentration in the assay, and AFixa, norm is average normalized activity of free FIXa.

Determination of FIXa Saturation

The fraction of FIXa saturated with OA antibody in the assay is determined by the concentrations of FIXa and OA antibody, and the equilibrium dissociation constant ($K_d$) governing their interaction. The latter can be measured by techniques known in the art, such as isothermal titration calorimetry (ITC).

Since the stimulation index will increase as the concentration of OA antibody is increased until saturation of FIXa is reached, the concentration of OA antibody in the assay should be chosen to ensure at least 80% saturation of FIXa in the assay to provide a proper determination of the stimulation index at full FIXa saturation.

The fraction of FIXa bound to OA antibody at equilibrium ($f_{FIXa+OA}$), can be calculated from the total concentrations of FIXa ([FIXa] total) and OA antibody ([OA] total) in the assay and the equilibrium dissociation constant ($K_d$) for their interaction using the quadractic binding equation as described by Krishnaswamy et al. (1992) *J. Biol. Chem.,* 267:23696-23706 and detailed in Eq. 4 and 5 below, wherein

[FIXa+OA] assay represents the calculated concentration of FIXa–OA antibody complex at equilibrium in the assay $f_{FIXa+OA}$ represents the calculated fraction (in percent) of FIXa, which is bound to OA antibody at equilibrium in the assay $$[FIXa+OA]_{assay} = \frac{([FIXa]_{total} + [OA]_{total} + K_d) - \sqrt{([FIXa]_{total} + [OA]_{total} + K_d)^2 - 4 \times [FIXa]_{total} \times [OA]_{total}}}{2} \quad \text{Eq. 4}$$

$$f_{FIXa+OA} = 100\% \times \frac{[FIXa+OA]_{assay}}{[FIXa]_{total}} \quad \text{Eq. 5}$$

The stimulation index for each OA antibody is provided in Table 7. In the case of the OA emicizumab antibody, FIXa stimulation was determined at eight different antibody concentrations which allowed for the estimation of the stimulation index at full FIXa saturation using the quadratic binding equation as outlined above. This also provided an estimated equilibrium dissociation constant ($K_d$) for the interaction of emicizumab with FIXa of 1.1 µM, which is in good agreement with the value of 1.52 µM reported by Kitazawa et al. (2017) Thromb Haemost, 117:1348-1357. For the remaining antibodies, the degree of FIXa saturation was not known and the listed stimulation indices therefore represent conservative estimates of the stimulation that would be obtained at a degree of FIXa saturation of 80% or greater. For the tested antibodies the measured stimulation index was found to be higher than that measured for the OA emicizumab antibody.

TABLE 7

Stimulation of FIXa activity by monovalent one-armed (OA) anti-FIXa antibodies
The anti-FIX mAb ID refers to the ID of the antibody used for reformatting into the OA format. Columns labelled 'OA antibody concentration (nM)' and 'Stimulation index' list the concentration of OA antibody (nM) used in the assay and the corresponding stimulation of FIXa activity measured relative to free FIXa. In the case of emicizumab, the estimated stimulation index at full FIXa saturation is provided.

| anti-FIX mAb ID | OA antibody concentration (nM) | Stimulation Index |
|---|---|---|
| emicizumab | saturation | 1372 |
| mAb1 | 1599 | 9841 |
| mAb2 | 5640 | 14228 |
| mAb3 | 749 | 8649 |
| mAb4 | 1217 | 10537 |
| mAb5 | 1463 | 11241 |
| mAb6 | 3547 | 13510 |
| mAb7 | 851 | 8727 |
| mAb8 | 1276 | 10089 |

Example 10: SEC-HPLC Analysis of Non-Specific Binding

Low non-specific binding is an important feature of pharmaceutical antibodies. High propensity of non-specific binding can lead to issues such as compromised in vivo half-life (Hötzel, I., et al., mAbs, 2012 & Avery, L. B., mAbs, 2018) and decreased solubility (*Kohli*, N., mAbs, 2015 & Wolf Perez, A. M., mAbs, 2019). To evaluate the non-specific binding of the anti-FIX(a) mAbs listed in table 8 below we have used a SEC-HPLC method where mAb-column interactions leads to delayed elution. Thus, prolonged retention times is a measure of non-specific binding. We have used a method previously described (Wolf Perez, A. M., mAbs, 2019) and highly similar to the method described in (Dobson, C. L., *Sci Rep,* 2016; 6: 38644). For BimAbs1-8 there is a decrease in non-specific binding relative to emicizumab $V_H/V_L$ SIA prepared as described in example 4, see table 8.

Materials and Methods

Size Exclusion Chromatography HPLC (SEC-HPLC) analysis was performed with a HPLC system (1200 model, Agilent Technologies) and a TSK G3000 SWXL SEC Column (5 μm, 7.8×300 mm; Tosoh Bioscience). The mobile phase consisted of 122 mM $Na_2HPO_4$, 78 mM $NaH_2PO_4$, 300 mM NaCl and 4% 2-propanol at pH 6.8. each analysis ran for 24 mins with a flow rate of 0.8 mL/min, with a column temperature of 28° C. 15 μl of protein solution was injected on the column and elution was followed with 280 nm absorbance. Data processing was performed using Astra v.7 (Wyatt technology).

TABLE 8

Change in retention time

| BimAb ID | Change in retention time relative to emicizumab (min) | BimAb ID | Change in retention time relative to emicizumab (min) |
|---|---|---|---|
| bimAb3A | −0.40 | bimAb3B | −0.40 |
| bimAb7A | −0.39 | bimAb7B | −0.40 |
| bimAb1A | −0.36 | bimAb1B | −0.37 |
| bimAb4A | −0.36 | bimAb4B | −0.37 |
| bimAb8A | −0.36 | bimAb8B | −0.37 |
| bimAb2A | −0.35 | bimAb2B | −0.35 |
| bimAb5A | −0.35 | bimAb5B | −0.35 |
| bimAb6A | −0.31 | bimAb6B | −0.31 |
| emicizumab | 0.00 | emicizumab | 0.00 |

The invention claimed is:

1. A bispecific antibody or an antigen-binding fragment thereof capable of binding to FIX (SEQ ID NO:89) and/or the activated form thereof (FIXa), and capable of binding to FX (SEQ ID NO:90) and/or the activated form thereof (FXa), wherein said bispecific antibody comprises an anti-FIX(a) antibody or an antigen-binding fragment thereof comprising a heavy chain and a light chain, and an anti-FX(a) antibody or an antigen-binding fragment thereof comprising a heavy chain and a light chain, wherein a) the heavy chain of the anti-FIX(a) antibody or the antigen-binding fragment thereof comprises CDR1-3 sequences identified by SEQ ID NOs: 26, 27 and 28, respectively, and the light chain of the anti-FIX(a) antibody or the antigen-binding fragment thereof comprises CDR1-3 sequences identified by SEQ ID NOs: 30, 31 and 32, respectively, and the heavy chain of the anti-FX(a) antibody or the antigen-binding fragment thereof comprises CDR1-3 sequences identified by SEQ ID NOs: 18, 19 and 20, respectively, and the light chain of the anti-FX(a) antibody or the antigen-binding fragment thereof comprises CDR1-3 sequences identified by SEQ ID NOs: 22, 23 and 24, respectively; or b) the heavy chain of the anti-FIX(a) antibody or the antigen-binding fragment thereof comprises CDR1-3 sequences identified by SEQ ID NOs: 26, 27 and 28, respectively, and the light chain of the anti-FIX(a) antibody or the antigen-binding fragment thereof comprises CDR1-3 sequences identified by SEQ ID NOs: 30, 31 and 32, respectively, and the heavy chain of the anti-FX(a) antibody or the antigen-binding fragment thereof comprises CDR1-3 sequences identified by SEQ ID NOs: 2, 3 and 4, respectively, and the light chain of the anti-FX(a) antibody or the antigen-binding fragment thereof comprises CDR1-3 sequences identified by SEQ ID NOs: 6, 7 and 8, respectively; or c) the heavy chain of the anti-FIX(a) antibody or the antigen-binding fragment thereof comprises CDR1-3 sequences identified by SEQ ID NOs: 34, 35 and 36, respectively, and the light chain of the anti-FIX(a) antibody or the antigen-binding fragment thereof comprises CDR1-3 sequences identified by SEQ ID NOs: 38, 39 and 40, respectively, and the heavy chain of the anti-FX(a) antibody or the antigen-binding fragment thereof comprises CDR 1-3 sequences identified by SEQ ID NOs: 18, 19 and 20, respectively, and the light chain of the anti-FX(a) antibody or the antigen-binding fragment thereof comprises CDR1-3 sequences identified by SEQ ID NOs: 22, 23 and 24, respectively; or d) the heavy chain of the anti-FIX(a) antibody or the antigen-binding fragment thereof comprises CDR1-3 sequences identified by SEQ ID NOs: 34, 35 and 36, respectively, and the light chain of the anti-FIX(a) antibody or the antigen-binding fragment thereof comprises CDR1-3 sequences identified by SEQ ID NOs: 38, 39 and 40, respectively, and the heavy chain of the anti-FX(a) antibody or the antigen-binding fragment thereof comprises CDR1-3 sequences identified by SEQ ID NOs: 2, 3 and 4, respectively, and the light chain of the anti-FX(a) antibody or the antigen-binding fragment thereof comprises CDR1-3 sequences identified by SEQ ID NOs: 6, 7 and 8, respectively; or e) the heavy chain of the anti-FIX(a) antibody or the antigen-binding fragment thereof comprises CDR1-3 sequences identified by SEQ ID NOs: 42, 43 and 44, respectively, and the light chain of the anti-FIX(a) antibody or the antigen-binding fragment thereof comprises CDR1-3 sequences identified by SEQ ID NOs: 46, 47 and 48, respectively, and the heavy chain of the anti-FX(a) antibody or the antigen-binding fragment thereof comprises CDR1-3 sequences identified by SEQ ID NOs: 18, 19 and 20, respectively, and the light chain of the anti-FX(a) antibody or the antigen-binding fragment thereof comprises CDR1-3 sequences identified by SEQ ID NOs: 22, 23 and 24, respectively; or f) the heavy chain of the anti-FIX(a) antibody or the antigen-binding fragment thereof comprises CDR1-3 sequences identified by SEQ ID NOs: 42, 43 and 44, respectively, and the light chain of the anti-FIX(a) antibody or the antigen-binding fragment thereof comprises CDR1-3 sequences identified by SEQ ID NOs: 46, 47 and 48, respectively, and the heavy chain of the anti-FX(a) antibody or the antigen-binding fragment thereof comprises CDR1-3 sequences identified by SEQ ID NOs: 2, 3 and 4, respectively, and the light chain of the anti-FX(a) antibody or the antigen-binding fragment thereof comprises CDR1-3 sequences identified by SEQ ID NOs: 6, 7 and 8, respectively; or g) the heavy chain of the anti-FIX(a) antibody or the antigen-binding fragment thereof comprises CDR1-3 sequences identified by SEQ ID NOs: 50, 51 and 52, respectively, and the light chain of the anti-FIX(a) antibody or the antigen-binding fragment thereof comprises CDR1-3 sequences identified by SEQ ID NOs: 54, 55 and 56, respectively, and the heavy chain of the anti-FX(a) antibody or the antigen-binding fragment thereof comprises CDR1-3 sequences identified by SEQ ID NOs: 18, 19 and 20, respectively, and the light chain of the anti-FX(a) antibody or the antigen-binding fragment thereof comprises CDR1-3 sequences identified by SEQ ID NOs: 22, 23 and 24, respectively; or h) the heavy chain of the anti-FIX(a) antibody or the antigen-binding fragment thereof comprises CDR1-3 sequences identified by SEQ ID NOs: 50, 51 and 52, respectively, and the light chain of the anti-FIX(a) antibody or the antigen-binding fragment thereof comprises CDR1-3 sequences identified by SEQ ID NOs: 54, 55 and 56, respectively, and the heavy chain of the anti-FX(a) antibody or the antigen-binding fragment thereof comprises CDR1-3 sequences identified by SEQ ID NOs: 2, 3 and 4, respectively, and the light chain of the anti-FX(a) antibody or the antigen-binding fragment thereof comprises CDR1-3 sequences identified by SEQ ID NOs: 6, 7 and 8, respectively; or i) the heavy chain of the anti-FIX(a) antibody or the antigen-binding fragment thereof comprises CDR1-3 sequences identified by SEQ ID NOs: 58, 59 and 60, respectively, and the light chain of the anti-FIX(a) antibody or the antigen-binding fragment thereof comprises CDR1-3 sequences identified by SEQ ID NOs: 62, 63 and 64, respectively, and the heavy chain of the anti-FX(a) antibody or the antigen-binding fragment thereof comprises CDR1-3 sequences identified by SEQ ID NOs: 18, 19 and 20, respectively, and the light chain of the anti-FX(a) antibody or the antigen-binding fragment thereof comprises CDR1-3 sequences identified by SEQ ID NOs: 22, 23 and 24, respectively; or j) the heavy chain of the anti-FIX(a) antibody or the antigen-binding fragment thereof comprises CDR1-3 sequences identified by SEQ ID NOs: 58, 59 and 60, respectively, and the light chain of the anti-FIX(a) antibody or the antigen-binding fragment thereof comprises CDR1-3 sequences identified by SEQ ID NOs: 62, 63 and 64, respectively, and the heavy chain of the anti-FX(a) antibody or the antigen-binding fragment thereof comprises CDR1-3 sequences identified by SEQ ID NOs: 2, 3 and 4, respectively, and the light chain of the anti-FX(a) antibody or the antigen-binding fragment thereof comprises CDR1-3 sequences identified by SEQ ID NOs: 6, 7 and 8, respectively; or k) the heavy chain of the anti-FIX(a) antibody or the antigen-binding fragment thereof comprises CDR1-3 sequences identified by SEQ ID NOs: 66, 67 and 68, respectively, and the light chain of the anti-FIX(a) antibody or the antigen-binding fragment thereof comprises CDR1-3 sequences identified by SEQ ID NOs: 70, 71 and 72, respectively, and the heavy chain of the anti-FX(a) antibody or the antigen-binding fragment thereof comprises CDR1-3 sequences identified by SEQ ID NOs: 18, 19 and 20, respectively, and the light chain of the anti-FX(a) antibody or the antigen-binding fragment thereof comprises CDR1-3 sequences identified by SEQ ID NOs: 22, 23 and 24, respectively; or l) the heavy chain of the anti-FIX(a) antibody or the antigen-binding fragment thereof comprises CDR1-3 sequences identified by SEQ ID NOs: 66, 67 and 68, respectively, and the light chain of the anti-FIX(a) antibody or the antigen-binding fragment thereof comprises CDR1-3 sequences identified by SEQ ID NOs: 70, 71 and 72, respectively, and the heavy chain of the anti-FX(a) antibody or the antigen-binding fragment thereof comprises CDR1-3 sequences identified by SEQ ID NOs: 2, 3 and 4, respectively, and the light chain of the anti-FX(a) antibody or the antigen-binding fragment thereof comprises CDR1-3 sequences identified by SEQ ID NOs: 6, 7 and 8, respectively; or m) the heavy chain of the anti-FIX(a) antibody or the antigen-binding fragment thereof comprises CDR1-3 sequences identified by SEQ ID NOs: 74, 75 and 76, respectively, and the light chain of the anti-FIX(a) antibody or the antigen-binding fragment thereof comprises CDR1-3 sequences identified by SEQ ID NOs: 78, 79 and 80, respectively, and the heavy chain of the anti-FX(a) antibody or the antigen-binding fragment thereof comprises CDR1-3 sequences identified by SEQ ID NOs: 18, 19 and 20, respectively, and the light chain of the anti-FX(a) antibody or the antigen-binding fragment thereof comprises CDR1-3 sequences identified by SEQ ID NOs: 22, 23 and 24, respectively; or n) the heavy chain of the anti-FIX(a) antibody or the antigen-binding fragment thereof comprises CDR1-3 sequences identified by SEQ ID NOs: 74, 75 and 76, respectively, and the light chain of the anti-FIX(a) antibody or the antigen-binding fragment thereof comprises CDR1-3 sequences identified by SEQ ID NOs: 78, 79 and 80, respectively, and the heavy chain of the anti-FX(a) antibody or the antigen-binding fragment thereof comprises CDR1-3 sequences identified by SEQ ID NOs: 2, 3 and 4, respectively, and the light chain of the anti-FX(a) antibody or the antigen-binding fragment thereof comprises CDR1-3 sequences identified by SEQ ID NOs: 6, 7 and 8, respectively; or o) the heavy chain of the anti-FIX(a) antibody or the antigen-binding fragment thereof comprises CDR1-3 sequences identified by SEQ ID NOs: 82, 83 and 84, respectively, and the light chain of the anti-FIX(a) antibody or the antigen-binding fragment thereof comprises CDR1-3 sequences identified by SEQ ID NOs: 86, 87 and 88, respectively, and the heavy chain of the anti-FX(a) antibody or the antigen-binding fragment thereof comprises CDR1-3 sequences identified by SEQ ID NOs: 18, 19 and 20, respectively, and the light chain of the anti-FX(a) antibody or the antigen-binding fragment thereof comprises CDR1-3 sequences identified by SEQ ID NOs: 22, 23 and 24, respectively; or p) the heavy chain of the anti-FIX(a) antibody or the antigen-binding fragment thereof comprises CDR1-3 sequences identified by SEQ ID NOs: 82, 83 and 84, respectively, and the light chain of the anti-FIX(a) antibody or the antigen-binding fragment thereof comprises CDR1-3 sequences identified by SEQ ID NOs: 86, 87 and 88, respectively, and the heavy chain of the anti-FX(a) antibody or the antigen-binding fragment thereof comprises CDR1-3 sequences identified by SEQ ID NOs: 2, 3 and 4, respectively, and the light chain of the anti-FX(a) antibody or the antigen-binding fragment thereof comprises CDR1-3 sequences identified by SEQ ID NOs: 6, 7 and 8, respectively.

2. The bispecific antibody or the antigen-binding fragment thereof according to claim 1 wherein the anti-FIX(a) antibody or the antigen-binding fragment thereof comprises a. a heavy chain variable domain identified by SEQ ID NO:25 and a light chain variable domain identified by SEQ ID NO:29; or
b. a heavy chain variable domain identified by SEQ ID NO:33 and a light chain variable domain identified by SEQ ID NO:37; or
c. a heavy chain variable domain identified by SEQ ID NO:41 and a light chain variable domain identified by SEQ ID NO:45; or
d. a heavy chain variable domain identified by SEQ ID NO:49 and a light chain variable domain identified by SEQ ID NO:53; or
e. a heavy chain variable domain identified by SEQ ID NO:57 and a light chain variable domain identified by SEQ ID NO:61; or
f. a heavy chain variable domain identified by SEQ ID NO:65 and a light chain variable domain identified by SEQ ID NO:69; or
g. a heavy chain variable domain identified by SEQ ID NO:73 and a light chain variable domain identified by SEQ ID NO:77; or
h. a heavy chain variable domain identified by SEQ ID NO:81 and a light chain variable domain identified by SEQ ID NO:85;

and wherein the anti-FX(a) antibody or the antigen-binding fragment thereof comprises i. a heavy chain variable domain identified by SEQ ID NO:17 and a light chain variable domain identified by SEQ ID NO:21; or
ii. a heavy chain variable domain identified by SEQ ID NO:1 and a light chain variable domain identified by SEQ ID NO:5.

3. The bispecific antibody or the antigen-binding fragment thereof according to claim 1, wherein the isotype of the bispecific antibody is IgG1 or IgG4.

4. The bispecific antibody or the antigen-binding fragment thereof according to claim 1, wherein said antibody or antigen-binding fragment thereof is a procoagulant antibody or antigen-binding fragment thereof.

5. The bispecific antibody or the antigen-binding fragment thereof according to claim 1, wherein said antibody or antigen-binding fragment thereof is capable of stimulating the enzymatic activity of FIXa.

6. A pharmaceutical composition comprising the bispecific antibody or the antigen-binding fragment thereof according to claim 1 and one or more pharmaceutically acceptable carrier(s).

7. A method of treating a subject suffering from haemophilia, comprising administering the bispecific antibody or the antigen-binding fragment thereof according to claim 1 to said subject.

8. A method of treating a subject suffering from haemophilia A with or without inhibitors, comprising administering the bispecific antibody or the antigen-binding fragment thereof according to claim 1 to said subject.

9. A method of prophylactic treating a subject suffering from haemophilia A with or without inhibitors, comprising administering the bispecific antibody or the antigen-binding fragment thereof according to claim 1 to said subject.

10. A method of treating a subject suffering from haemophilia A with or without inhibitors, comprising administering to said subject the bispecific antibody or the antigen-binding fragment thereof or composition according to claim 2.

11. The method according to claim 10, wherein the treatment is prophylactic treatment.

12. A method of treating a subject suffering from haemophilia, comprising administering the bispecific antibody or the antigen-binding fragment thereof according to claim 2 to said subject.

13. An antibody or an antigen-binding fragment thereof which is capable of binding to FIX (SEQ ID NO:89) and/or the activated form thereof (FIXa) comprising a heavy chain and a light chain wherein a) the heavy chain comprises CDR1-3 sequences identified by SEQ ID NOs: 26, 27 and 28, respectively, and the light chain comprises CDR1-3 sequences identified by SEQ ID NOs: 30, 31 and 32, respectively; or b) the heavy chain comprises CDR1-3 sequences identified by SEQ ID NOs: 34, 35 and 36, respectively, and the light chain comprises CDR1-3 sequences identified by SEQ ID NOs: 38, 39 and 40, respectively; or c) the heavy chain comprises CDR1-3 sequences identified by SEQ ID NOs: 42, 43 and 44, respectively, and the light chain comprises CDR1-3 sequences identified by SEQ ID NOs: 46, 47 and 48, respectively; or d) the heavy chain comprises CDR1-3 sequences identified by SEQ ID NOs: 50, 51 and 52, respectively, and the light chain comprises CDR1-3 sequences identified by SEQ ID NOs: 54, 55 and 56, respectively; or e) the heavy chain comprises CDR1-3 sequences identified by SEQ ID NOs: 58, 59 and 60, respectively, and the light chain comprises CDR1-3 sequences identified by SEQ ID NOs: 62, 63 and 64, respectively; or f) the heavy chain comprises CDR1-3 sequences identified by SEQ ID NOs: 66, 67 and 68, respectively, and the light chain comprises CDR1-3 sequences identified by SEQ ID NOs: 70, 71 and 72, respectively; or g) the heavy chain comprises CDR1-3 sequences identified by SEQ ID NOs: 74, 75 and 76, respectively, and the light chain comprises CDR1-3 sequences identified by SEQ ID NOs: 78, 79 and 80, respectively; or h) the heavy chain comprises CDR1-3 sequences identified by SEQ ID NOs: 82, 83 and 84, respectively, and the light chain comprises CDR1-3 sequences identified by SEQ ID NOs: 86, 87 and 88, respectively.

14. The antibody or antigen-binding fragment thereof according to claim 13, wherein said antibody or antigen-binding fragment thereof is a procoagulant antibody or antigen-binding fragment thereof.

15. The antibody or antigen-binding fragment thereof according to claim 13, wherein said antibody or antigen-binding fragment thereof is capable of stimulating the enzymatic activity of FIXa.

16. A kit comprising (i) the bispecific antibody or antigen-binding fragment thereof according to claim 1, optionally comprised by an injection device and (ii) instructions for use.

17. A kit comprising (i) the bispecific antibody or antigen-binding fragment thereof according to claim 2, optionally comprised by an injection device and (ii) instructions for use.

18. The bispecific antibody or the antigen-binding fragment thereof according to claim 2, wherein the isotype of the bispecific antibody is IgG1 or IgG4.

19. The bispecific antibody or the antigen-binding fragment thereof according to claim 2, wherein said antibody or antigen-binding fragment thereof is a procoagulant antibody or antigen-binding fragment thereof.

20. The bispecific antibody or the antigen-binding fragment thereof according to claim 2, wherein said antibody or antigen-binding fragment thereof is capable of stimulating the enzymatic activity of FIXa.

21. A pharmaceutical composition comprising the bispecific antibody or the antigen-binding fragment thereof according to claim 2, and one or more pharmaceutically acceptable carrier(s).

* * * * *

SEQUENCE LISTING

<160> NUMBER OF SEQ ID NOS: 95

<210> SEQ ID NO 1
<211> LENGTH: 120
<212> TYPE: PRT
<213> ORGANISM: Artificial Sequence
<220> FEATURE:
<223> OTHER INFORMATION: Synthetic

<400> SEQUENCE: 1

Glu Val Gln Leu Val Gln Ser Gly Ala Glu Val Lys Lys Pro Gly Glu
1 5 10 15

Ser Leu Arg Ile Ser Cys Lys Gly Ser Gly Tyr Ser Phe Ser Thr Ser
20 25 30

Trp Ile Val Trp Val Arg Gln Met Pro Gly Lys Gly Leu Glu Trp Met
35 40 45

Gly Met Ile Asp Pro Ser Asp Ser Phe Thr Ser Tyr Ser Pro Ser Phe
50 55 60

Gln Gly His Val Thr Ile Ser Ala Asp Lys Ser Ile Ser Thr Ala Tyr
65 70 75 80

Leu Gln Trp Ser Ser Leu Lys Ala Ser Asp Thr Ala Met Tyr Tyr Cys
85 90 95

Ala Arg Leu His Tyr Tyr Asn Ser Glu Glu Phe Asp Val Trp Gly Gln
100 105 110

Gly Thr Leu Val Thr Val Ser Ser
115 120

<210> SEQ ID NO 2
<211> LENGTH: 5
<212> TYPE: PRT
<213> ORGANISM: Artificial Sequence
<220> FEATURE:
<223> OTHER INFORMATION: Synthetic

<400> SEQUENCE: 2

Thr Ser Trp Ile Val
1 5

<210> SEQ ID NO 3
<211> LENGTH: 17
<212> TYPE: PRT
<213> ORGANISM: Artificial Sequence
<220> FEATURE:
<223> OTHER INFORMATION: Synthetic

<400> SEQUENCE: 3

Met Ile Asp Pro Ser Asp Ser Phe Thr Ser Tyr Ser Pro Ser Phe Gln
1 5 10 15

Gly

<210> SEQ ID NO 4
<211> LENGTH: 11
<212> TYPE: PRT
<213> ORGANISM: Artificial Sequence
<220> FEATURE:
<223> OTHER INFORMATION: Synthetic

<400> SEQUENCE: 4

Leu His Tyr Tyr Asn Ser Glu Glu Phe Asp Val
1 5 10

<210> SEQ ID NO 5
<211> LENGTH: 109
<212> TYPE: PRT
<213> ORGANISM: Artificial Sequence
<220> FEATURE:
<223> OTHER INFORMATION: Synthetic

<400> SEQUENCE: 5

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Gln Ser Ser Arg Thr Arg Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Phe Gly Asp Ser Gln
85 90 95

Leu Phe Thr Phe Gly Gln Gly Thr Lys Leu Glu Ile Lys
100 105

<210> SEQ ID NO 6
<211> LENGTH: 12
<212> TYPE: PRT
<213> ORGANISM: Artificial Sequence
<220> FEATURE:
<223> OTHER INFORMATION: Synthetic

<400> SEQUENCE: 6

Arg Ala Ser Gln Ser Val Ser Ser Ser Tyr Leu Ala
1 5 10

<210> SEQ ID NO 7
<211> LENGTH: 7
<212> TYPE: PRT

<213> ORGANISM: Artificial Sequence
<220> FEATURE:
<223> OTHER INFORMATION: Synthetic

<400> SEQUENCE: 7

Gly Gln Ser Ser Arg Thr Arg
1               5

<210> SEQ ID NO 8
<211> LENGTH: 10
<212> TYPE: PRT
<213> ORGANISM: Artificial Sequence
<220> FEATURE:
<223> OTHER INFORMATION: Synthetic

<400> SEQUENCE: 8

Gln Gln Phe Gly Asp Ser Gln Leu Phe Thr
1               5                   10

<210> SEQ ID NO 9

<400> SEQUENCE: 9

000

<210> SEQ ID NO 10

<400> SEQUENCE: 10

000

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

```
<210> SEQ ID NO 17
<211> LENGTH: 120
<212> TYPE: PRT
<213> ORGANISM: Artificial Sequence
<220> FEATURE:
<223> OTHER INFORMATION: Synthetic

<400> SEQUENCE: 17

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Ser
            20                  25                  30

Trp Ile Val Trp Val Arg Gln Met Pro Gly Lys Gly Leu Glu Trp Met
        35                  40                  45

Gly Met Ile Asp Pro Ser Asp Ser Tyr Thr Ser Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu His Tyr Tyr Asn Ser Glu Glu Phe Asp Val Trp Gly Gln
            100                 105                 110

Gly Thr Met Val Thr Val Ser Ser
        115                 120


<210> SEQ ID NO 18
<211> LENGTH: 5
<212> TYPE: PRT
<213> ORGANISM: Artificial Sequence
<220> FEATURE:
<223> OTHER INFORMATION: Synthetic

<400> SEQUENCE: 18

Thr Ser Trp Ile Val
1               5


<210> SEQ ID NO 19
<211> LENGTH: 17
<212> TYPE: PRT
<213> ORGANISM: Artificial Sequence
<220> FEATURE:
<223> OTHER INFORMATION: Synthetic

<400> SEQUENCE: 19

Met Ile Asp Pro Ser Asp Ser Tyr Thr Ser Tyr Ser Pro Ser Phe Gln
1               5                   10                  15

Gly


<210> SEQ ID NO 20
<211> LENGTH: 11
<212> TYPE: PRT
<213> ORGANISM: Artificial Sequence
<220> FEATURE:
<223> OTHER INFORMATION: Synthetic

<400> SEQUENCE: 20

Leu His Tyr Tyr Asn Ser Glu Glu Phe Asp Val
1               5                   10


<210> SEQ ID NO 21
<211> LENGTH: 109
<212> TYPE: PRT
<213> ORGANISM: Artificial Sequence
```

<220> FEATURE:
<223> OTHER INFORMATION: Synthetic

<400> SEQUENCE: 21

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Gln Ser Ser Arg Thr Arg Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Phe Gly Glu Ser Gln
85 90 95

Leu Phe Thr Phe Gly Gln Gly Thr Lys Leu Glu Ile Lys
100 105

<210> SEQ ID NO 22
<211> LENGTH: 12
<212> TYPE: PRT
<213> ORGANISM: Artificial Sequence
<220> FEATURE:
<223> OTHER INFORMATION: Synthetic

<400> SEQUENCE: 22

Arg Ala Ser Gln Ser Val Ser Ser Ser Tyr Leu Ala
1 5 10

<210> SEQ ID NO 23
<211> LENGTH: 7
<212> TYPE: PRT
<213> ORGANISM: Artificial Sequence
<220> FEATURE:
<223> OTHER INFORMATION: Synthetic

<400> SEQUENCE: 23

Gly Gln Ser Ser Arg Thr Arg
1 5

<210> SEQ ID NO 24
<211> LENGTH: 10
<212> TYPE: PRT
<213> ORGANISM: Artificial Sequence
<220> FEATURE:
<223> OTHER INFORMATION: Synthetic

<400> SEQUENCE: 24

Gln Gln Phe Gly Glu Ser Gln Leu Phe Thr
1 5 10

<210> SEQ ID NO 25
<211> LENGTH: 122
<212> TYPE: PRT
<213> ORGANISM: Artificial Sequence
<220> FEATURE:
<223> OTHER INFORMATION: Synthetic

<400> SEQUENCE: 25

Glu Val Gln Leu Val Glu Ser Gly Gly Gly Leu Val Gln Pro Gly Arg
1 5 10 15

Ser Leu Arg Leu Ser Cys Ala Ala Ser Gly Phe Thr Phe His Asp Tyr

```
            20                  25                  30

Ala Met His Trp Val Arg Gln Val Pro Gly Lys Gly Leu Glu Trp Val
        35                  40                  45

Ser Gly Ile Ser Trp Arg Gly Asp Ile Gly Gly Tyr Val Lys Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120


<210> SEQ ID NO 26
<211> LENGTH: 5
<212> TYPE: PRT
<213> ORGANISM: Artificial Sequence
<220> FEATURE:
<223> OTHER INFORMATION: Synthetic

<400> SEQUENCE: 26

Asp Tyr Ala Met His
1               5


<210> SEQ ID NO 27
<211> LENGTH: 17
<212> TYPE: PRT
<213> ORGANISM: Artificial Sequence
<220> FEATURE:
<223> OTHER INFORMATION: Synthetic

<400> SEQUENCE: 27

Gly Ile Ser Trp Arg Gly Asp Ile Gly Gly Tyr Val Lys Ser Val Lys
1               5                   10                  15

Gly


<210> SEQ ID NO 28
<211> LENGTH: 13
<212> TYPE: PRT
<213> ORGANISM: Artificial Sequence
<220> FEATURE:
<223> OTHER INFORMATION: Synthetic

<400> SEQUENCE: 28

Ser Tyr Gly Ser Gly Ser Phe Tyr Asn Ala Phe Asp Ser
1               5                   10


<210> SEQ ID NO 29
<211> LENGTH: 107
<212> TYPE: PRT
<213> ORGANISM: Artificial Sequence
<220> FEATURE:
<223> OTHER INFORMATION: Synthetic

<400> SEQUENCE: 29

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45
```

Tyr Lys Gly Ser Lys Ala Asp Arg Gly Thr Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Leu Glu Tyr Glu Ser Tyr Ile Arg
85 90 95

Thr Phe Gly Gln Gly Thr Lys Val Glu Ile Lys
100 105

<210> SEQ ID NO 30
<211> LENGTH: 11
<212> TYPE: PRT
<213> ORGANISM: Artificial Sequence
<220> FEATURE:
<223> OTHER INFORMATION: Synthetic

<400> SEQUENCE: 30

Arg Ala Ser Gln Ser Ile Ser Ser Trp Leu Ala
1 5 10

<210> SEQ ID NO 31
<211> LENGTH: 7
<212> TYPE: PRT
<213> ORGANISM: Artificial Sequence
<220> FEATURE:
<223> OTHER INFORMATION: Synthetic

<400> SEQUENCE: 31

Lys Gly Ser Lys Ala Asp Arg
1 5

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Leu Glu Tyr Glu Ser Tyr Ile Arg Thr
1 5

<210> SEQ ID NO 33
<211> LENGTH: 122
<212> TYPE: PRT
<213> ORGANISM: Artificial Sequence
<220> FEATURE:
<223> OTHER INFORMATION: Synthetic

<400> SEQUENCE: 33

Glu Val Gln Leu Val Glu Ser Gly Gly Gly Leu Val Gln Pro Gly Arg
1 5 10 15

Ser Leu Arg Leu Ser Cys Ala Ala Ser Gly Phe Thr Phe His Asp Tyr
20 25 30

Ala Met His Trp Val Arg Gln Val Pro Gly Lys Gly Leu Glu Trp Val
35 40 45

Ser Gly Ile Ser Trp Arg Gly Asp Ile Gly Gly Tyr Val Lys Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Leu Tyr Tyr Cys
85 90 95

Val Lys Ser Tyr Gly Ser Gly Ser Phe Tyr Asn Ala Phe Asp Ser Trp
100 105 110

Gly Gln Gly Thr Leu Val Thr Val Ser Ser
115 120

<210> SEQ ID NO 34
<211> LENGTH: 5
<212> TYPE: PRT
<213> ORGANISM: Artificial Sequence
<220> FEATURE:
<223> OTHER INFORMATION: Synthetic

<400> SEQUENCE: 34

Asp Tyr Ala Met His
1 5

<210> SEQ ID NO 35
<211> LENGTH: 17
<212> TYPE: PRT
<213> ORGANISM: Artificial Sequence
<220> FEATURE:
<223> OTHER INFORMATION: Synthetic

<400> SEQUENCE: 35

Gly Ile Ser Trp Arg Gly Asp Ile Gly Gly Tyr Val Lys Ser Val Lys
1 5 10 15

Gly

<210> SEQ ID NO 36
<211> LENGTH: 13
<212> TYPE: PRT
<213> ORGANISM: Artificial Sequence
<220> FEATURE:
<223> OTHER INFORMATION: Synthetic

<400> SEQUENCE: 36

Ser Tyr Gly Ser Gly Ser Phe Tyr Asn Ala Phe Asp Ser
1 5 10

<210> SEQ ID NO 37
<211> LENGTH: 107
<212> TYPE: PRT
<213> ORGANISM: Artificial Sequence
<220> FEATURE:
<223> OTHER INFORMATION: Synthetic

<400> SEQUENCE: 37

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Ser Ser Trp
20 25 30

Leu Ala Trp Tyr Gln Gln Lys Pro Gly Lys Ala Pro Lys Phe Leu Ile
35 40 45

Tyr Lys Gly Ser Lys Gln Asp Arg Gly Thr Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Leu Glu Tyr Ser Ser Tyr Ile Arg
85 90 95

Thr Phe Gly Gln Gly Thr Lys Val Glu Ile Lys
100 105

<210> SEQ ID NO 38
<211> LENGTH: 11
<212> TYPE: PRT
<213> ORGANISM: Artificial Sequence
<220> FEATURE:
<223> OTHER INFORMATION: Synthetic

<400> SEQUENCE: 38

Arg Ala Ser Gln Ser Ile Ser Ser Trp Leu Ala
1               5                   10

<210> SEQ ID NO 39
<211> LENGTH: 7
<212> TYPE: PRT
<213> ORGANISM: Artificial Sequence
<220> FEATURE:
<223> OTHER INFORMATION: Synthetic

<400> SEQUENCE: 39

Lys Gly Ser Lys Gln Asp Arg
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic

<400> SEQUENCE: 40

Leu Glu Tyr Ser Ser Tyr Ile Arg Thr
1               5

<210> SEQ ID NO 41
<211> LENGTH: 122
<212> TYPE: PRT
<213> ORGANISM: Artificial Sequence
<220> FEATURE:
<223> OTHER INFORMATION: Synthetic

<400> SEQUENCE: 41

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
        35                  40                  45

Ser Gly Ile Ser Trp Arg Gly Asp Ile Gly Gly Tyr Val Lys Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120

<210> SEQ ID NO 42
<211> LENGTH: 5
<212> TYPE: PRT
<213> ORGANISM: Artificial Sequence
<220> FEATURE:

<223> OTHER INFORMATION: Synthetic

<400> SEQUENCE: 42

Asp Tyr Ala Met His
1 5

<210> SEQ ID NO 43
<211> LENGTH: 17
<212> TYPE: PRT
<213> ORGANISM: Artificial Sequence
<220> FEATURE:
<223> OTHER INFORMATION: Synthetic

<400> SEQUENCE: 43

Gly Ile Ser Trp Arg Gly Asp Ile Gly Gly Tyr Val Lys Ser Val Lys
1 5 10 15

Gly

<210> SEQ ID NO 44
<211> LENGTH: 13
<212> TYPE: PRT
<213> ORGANISM: Artificial Sequence
<220> FEATURE:
<223> OTHER INFORMATION: Synthetic

<400> SEQUENCE: 44

Ser Tyr Gly Ser Gly Ser Phe Tyr Asn Ala Phe Asp Ser
1 5 10

<210> SEQ ID NO 45
<211> LENGTH: 107
<212> TYPE: PRT
<213> ORGANISM: Artificial Sequence
<220> FEATURE:
<223> OTHER INFORMATION: Synthetic

<400> SEQUENCE: 45

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Ser Ser Trp
20 25 30

Leu Ala Trp Tyr Gln Gln Lys Pro Gly Lys Ala Pro Lys Phe Leu Ile
35 40 45

Tyr Lys Gly Ser Lys Thr Asp Arg Gly Thr Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Leu Glu Tyr Glu Ser Tyr Ile Arg
85 90 95

Thr Phe Gly Gln Gly Thr Lys Val Glu Ile Lys
100 105

<210> SEQ ID NO 46
<211> LENGTH: 11
<212> TYPE: PRT
<213> ORGANISM: Artificial Sequence
<220> FEATURE:
<223> OTHER INFORMATION: Synthetic

<400> SEQUENCE: 46

Arg Ala Ser Gln Ser Ile Ser Ser Trp Leu Ala
1 5 10

<210> SEQ ID NO 47
<211> LENGTH: 7
<212> TYPE: PRT
<213> ORGANISM: Artificial Sequence
<220> FEATURE:
<223> OTHER INFORMATION: Synthetic

<400> SEQUENCE: 47

Lys Gly Ser Lys Thr Asp Arg
1 5

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Leu Glu Tyr Glu Ser Tyr Ile Arg Thr
1 5

<210> SEQ ID NO 49
<211> LENGTH: 122
<212> TYPE: PRT
<213> ORGANISM: Artificial Sequence
<220> FEATURE:
<223> OTHER INFORMATION: Synthetic

<400> SEQUENCE: 49

Glu Val Gln Leu Val Glu Ser Gly Gly Gly Leu Val Gln Pro Gly Arg
1 5 10 15

Ser Leu Arg Leu Ser Cys Ala Ala Ser Gly Phe Thr Phe His Asp Tyr
20 25 30

Ala Met His Trp Val Arg Gln Val Pro Gly Lys Gly Leu Glu Trp Val
35 40 45

Ser Gly Ile Ser Trp Arg Gly Asp Ile Gly Gly Tyr Val Lys Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Leu Tyr Tyr Cys
85 90 95

Val Lys Ser Tyr Gly Ser Gly Ser Phe Tyr Asn Ala Phe Asp Ser Trp
100 105 110

Gly Gln Gly Thr Leu Val Thr Val Ser Ser
115 120

<210> SEQ ID NO 50
<211> LENGTH: 5
<212> TYPE: PRT
<213> ORGANISM: Artificial Sequence
<220> FEATURE:
<223> OTHER INFORMATION: Synthetic

<400> SEQUENCE: 50

Asp Tyr Ala Met His
1 5

<210> SEQ ID NO 51
<211> LENGTH: 17
<212> TYPE: PRT
<213> ORGANISM: Artificial Sequence
<220> FEATURE:

<223> OTHER INFORMATION: Synthetic

<400> SEQUENCE: 51

Gly Ile Ser Trp Arg Gly Asp Ile Gly Gly Tyr Val Lys Ser Val Lys
1 5 10 15

Gly

<210> SEQ ID NO 52
<211> LENGTH: 13
<212> TYPE: PRT
<213> ORGANISM: Artificial Sequence
<220> FEATURE:
<223> OTHER INFORMATION: Synthetic

<400> SEQUENCE: 52

Ser Tyr Gly Ser Gly Ser Phe Tyr Asn Ala Phe Asp Ser
1 5 10

<210> SEQ ID NO 53
<211> LENGTH: 107
<212> TYPE: PRT
<213> ORGANISM: Artificial Sequence
<220> FEATURE:
<223> OTHER INFORMATION: Synthetic

<400> SEQUENCE: 53

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Ser Ser Trp
20 25 30

Leu Ala Trp Tyr Gln Gln Lys Pro Gly Lys Ala Pro Lys Phe Leu Ile
35 40 45

Tyr Lys Ser Glu Lys Leu Asp Arg Gly Thr Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Leu Glu Tyr Glu Ser Tyr Ile Arg
85 90 95

Thr Phe Gly Gln Gly Thr Lys Val Glu Ile Lys
100 105

<210> SEQ ID NO 54
<211> LENGTH: 11
<212> TYPE: PRT
<213> ORGANISM: Artificial Sequence
<220> FEATURE:
<223> OTHER INFORMATION: Synthetic

<400> SEQUENCE: 54

Arg Ala Ser Gln Ser Ile Ser Ser Trp Leu Ala
1 5 10

<210> SEQ ID NO 55
<211> LENGTH: 7
<212> TYPE: PRT
<213> ORGANISM: Artificial Sequence
<220> FEATURE:
<223> OTHER INFORMATION: Synthetic

<400> SEQUENCE: 55

Lys Ser Glu Lys Leu Asp Arg
1 5

<210> SEQ ID NO 56
<211> LENGTH: 9
<212> TYPE: PRT
<213> ORGANISM: Artificial Sequence
<220> FEATURE:
<223> OTHER INFORMATION: Synthetic

<400> SEQUENCE: 56

Leu Glu Tyr Glu Ser Tyr Ile Arg Thr
1 5

<210> SEQ ID NO 57
<211> LENGTH: 122
<212> TYPE: PRT
<213> ORGANISM: Artificial Sequence
<220> FEATURE:
<223> OTHER INFORMATION: Synthetic

<400> SEQUENCE: 57

Glu Val Gln Leu Val Glu Ser Gly Gly Gly Leu Val Gln Pro Gly Arg
1 5 10 15

Ser Leu Arg Leu Ser Cys Ala Ala Ser Gly Phe Thr Phe His Asp Tyr
20 25 30

Ala Met His Trp Val Arg Gln Val Pro Gly Lys Gly Leu Glu Trp Val
35 40 45

Ser Gly Ile Ser Trp Arg Gly Asp Ile Gly Gly Tyr Val Lys Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Leu Tyr Tyr Cys
85 90 95

Val Lys Ser Tyr Gly Ser Gly Ser Phe Tyr Asn Ala Phe Asp Ser Trp
100 105 110

Gly Gln Gly Thr Leu Val Thr Val Ser Ser
115 120

<210> SEQ ID NO 58
<211> LENGTH: 5
<212> TYPE: PRT
<213> ORGANISM: Artificial Sequence
<220> FEATURE:
<223> OTHER INFORMATION: Synthetic

<400> SEQUENCE: 58

Asp Tyr Ala Met His
1 5

<210> SEQ ID NO 59
<211> LENGTH: 17
<212> TYPE: PRT
<213> ORGANISM: Artificial Sequence
<220> FEATURE:
<223> OTHER INFORMATION: Synthetic

<400> SEQUENCE: 59

Gly Ile Ser Trp Arg Gly Asp Ile Gly Gly Tyr Val Lys Ser Val Lys
1 5 10 15

Gly

<210> SEQ ID NO 60
<211> LENGTH: 13
<212> TYPE: PRT

```
<213> ORGANISM: Artificial Sequence
<220> FEATURE:
<223> OTHER INFORMATION: Synthetic

<400> SEQUENCE: 60

Ser Tyr Gly Ser Gly Ser Phe Tyr Asn Ala Phe Asp Ser
1               5                   10


<210> SEQ ID NO 61
<211> LENGTH: 107
<212> TYPE: PRT
<213> ORGANISM: Artificial Sequence
<220> FEATURE:
<223> OTHER INFORMATION: Synthetic

<400> SEQUENCE: 61

Asp Ile Gln Met Thr Gln Ser Pro Ser Thr Leu Ser Ala Ser Val Gly
1               5                   10                  15

Asp Glu Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Gly Glu Lys Leu Asp Arg Gly Thr Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Leu Glu Tyr Ser Ser Tyr Ile Arg
                85                  90                  95

Thr Phe Gly Gln Gly Thr Lys Val Glu Ile Lys
            100                 105


<210> SEQ ID NO 62
<211> LENGTH: 11
<212> TYPE: PRT
<213> ORGANISM: Artificial Sequence
<220> FEATURE:
<223> OTHER INFORMATION: Synthetic

<400> SEQUENCE: 62

Arg Ala Ser Gln Ser Ile Ser Ser Trp Leu Ala
1               5                   10


<210> SEQ ID NO 63
<211> LENGTH: 7
<212> TYPE: PRT
<213> ORGANISM: Artificial Sequence
<220> FEATURE:
<223> OTHER INFORMATION: Synthetic

<400> SEQUENCE: 63

Lys Gly Glu Lys Leu Asp Arg
1               5


<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Leu Glu Tyr Ser Ser Tyr Ile Arg Thr
1               5
```

<210> SEQ ID NO 65
<211> LENGTH: 122
<212> TYPE: PRT
<213> ORGANISM: Artificial Sequence
<220> FEATURE:
<223> OTHER INFORMATION: Synthetic

<400> SEQUENCE: 65

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
        35                  40                  45

Ser Gly Ile Ser Trp Arg Gly Asp Ile Gly Gly Tyr Val Lys Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120
```

<210> SEQ ID NO 66
<211> LENGTH: 5
<212> TYPE: PRT
<213> ORGANISM: Artificial Sequence
<220> FEATURE:
<223> OTHER INFORMATION: Synthetic

<400> SEQUENCE: 66

```
Asp Tyr Ala Met His
1               5
```

<210> SEQ ID NO 67
<211> LENGTH: 17
<212> TYPE: PRT
<213> ORGANISM: Artificial Sequence
<220> FEATURE:
<223> OTHER INFORMATION: Synthetic

<400> SEQUENCE: 67

```
Gly Ile Ser Trp Arg Gly Asp Ile Gly Gly Tyr Val Lys Ser Val Lys
1               5                   10                  15

Gly
```

<210> SEQ ID NO 68
<211> LENGTH: 13
<212> TYPE: PRT
<213> ORGANISM: Artificial Sequence
<220> FEATURE:
<223> OTHER INFORMATION: Synthetic

<400> SEQUENCE: 68

```
Ser Tyr Gly Ser Gly Ser Phe Tyr Asn Ala Phe Asp Ser
1               5                   10
```

<210> SEQ ID NO 69
<211> LENGTH: 107
<212> TYPE: PRT

<213> ORGANISM: Artificial Sequence
<220> FEATURE:
<223> OTHER INFORMATION: Synthetic

<400> SEQUENCE: 69

Asp Ile Gln Met Thr Gln Ser Pro Ser Thr Leu Ser Ala Ser Val Gly
1 5 10 15

Asp Glu Val Thr Ile Thr Cys Arg Ala Ser Gln Ser Ile Ser Ser Trp
20 25 30

Leu Ala Trp Tyr Gln Gln Lys Pro Gly Lys Ala Pro Lys Phe Leu Ile
35 40 45

Tyr Lys Gly Ser Lys Leu Asp Arg Gly Thr Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Leu Glu Tyr Ser Ser Tyr Ile Arg
85 90 95

Thr Phe Gly Gln Gly Thr Lys Val Glu Ile Lys
100 105

<210> SEQ ID NO 70
<211> LENGTH: 11
<212> TYPE: PRT
<213> ORGANISM: Artificial Sequence
<220> FEATURE:
<223> OTHER INFORMATION: Synthetic

<400> SEQUENCE: 70

Arg Ala Ser Gln Ser Ile Ser Ser Trp Leu Ala
1 5 10

<210> SEQ ID NO 71
<211> LENGTH: 7
<212> TYPE: PRT
<213> ORGANISM: Artificial Sequence
<220> FEATURE:
<223> OTHER INFORMATION: Synthetic

<400> SEQUENCE: 71

Lys Gly Ser Lys Leu Asp Arg
1 5

<210> SEQ ID NO 72
<211> LENGTH: 9
<212> TYPE: PRT
<213> ORGANISM: Artificial Sequence
<220> FEATURE:
<223> OTHER INFORMATION: Synthetic

<400> SEQUENCE: 72

Leu Glu Tyr Ser Ser Tyr Ile Arg Thr
1 5

<210> SEQ ID NO 73
<211> LENGTH: 122
<212> TYPE: PRT
<213> ORGANISM: Artificial Sequence
<220> FEATURE:
<223> OTHER INFORMATION: Synthetic

<400> SEQUENCE: 73

Glu Val Gln Leu Val Glu Ser Gly Gly Gly Leu Val Gln Pro Gly Arg
1 5 10 15

```
Ser Leu Arg Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
        35                  40                  45

Ser Gly Ile Ser Trp Arg Gly Asp Ile Gly Gly Tyr Val Lys Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120


<210> SEQ ID NO 74
<211> LENGTH: 5
<212> TYPE: PRT
<213> ORGANISM: Artificial Sequence
<220> FEATURE:
<223> OTHER INFORMATION: Synthetic

<400> SEQUENCE: 74

Asp Tyr Ala Met His
1               5


<210> SEQ ID NO 75
<211> LENGTH: 17
<212> TYPE: PRT
<213> ORGANISM: Artificial Sequence
<220> FEATURE:
<223> OTHER INFORMATION: Synthetic

<400> SEQUENCE: 75

Gly Ile Ser Trp Arg Gly Asp Ile Gly Gly Tyr Val Lys Ser Val Lys
1               5                   10                  15

Gly


<210> SEQ ID NO 76
<211> LENGTH: 13
<212> TYPE: PRT
<213> ORGANISM: Artificial Sequence
<220> FEATURE:
<223> OTHER INFORMATION: Synthetic

<400> SEQUENCE: 76

Ser Tyr Gly Ser Gly Ser Phe Tyr Asn Ala Phe Asp Ser
1               5                   10


<210> SEQ ID NO 77
<211> LENGTH: 107
<212> TYPE: PRT
<213> ORGANISM: Artificial Sequence
<220> FEATURE:
<223> OTHER INFORMATION: Synthetic

<400> SEQUENCE: 77

Asp Ile Gln Met Thr Gln Ser Pro Ser Thr Leu Ser Ala Ser Val Gly
1               5                   10                  15

Asp Glu Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
```

```
        35                  40                  45

Tyr Lys Ala Glu Lys Leu Asp Arg Gly Thr Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Leu Glu Tyr Glu Ser Tyr Ile Arg
                85                  90                  95

Thr Phe Gly Gln Gly Thr Lys Val Glu Ile Lys
            100                 105


<210> SEQ ID NO 78
<211> LENGTH: 11
<212> TYPE: PRT
<213> ORGANISM: Artificial Sequence
<220> FEATURE:
<223> OTHER INFORMATION: Synthetic

<400> SEQUENCE: 78

Arg Ala Ser Gln Ser Ile Ser Ser Trp Leu Ala
1               5                   10


<210> SEQ ID NO 79
<211> LENGTH: 7
<212> TYPE: PRT
<213> ORGANISM: Artificial Sequence
<220> FEATURE:
<223> OTHER INFORMATION: Synthetic

<400> SEQUENCE: 79

Lys Ala Glu Lys Leu Asp Arg
1               5


<210> SEQ ID NO 80
<211> LENGTH: 9
<212> TYPE: PRT
<213> ORGANISM: Artificial Sequence
<220> FEATURE:
<223> OTHER INFORMATION: Synthetic

<400> SEQUENCE: 80

Leu Glu Tyr Glu Ser Tyr Ile Arg Thr
1               5


<210> SEQ ID NO 81
<211> LENGTH: 122
<212> TYPE: PRT
<213> ORGANISM: Artificial Sequence
<220> FEATURE:
<223> OTHER INFORMATION: Synthetic

<400> SEQUENCE: 81

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asp Tyr
            20                  25                  30

Ala Met His Trp Val Arg Gln Val Pro Gly Lys Gly Leu Glu Trp Val
        35                  40                  45

Ser Gly Ile Ser Trp Arg Gly Asp Ile Gly Gly Tyr Val Lys Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
```

```
                85                  90                  95

Val Lys Ser Tyr Gly Ser Gly Ser Phe Tyr Asn Ala Phe Asp Ser Trp
            100                 105                 110

Gly Gln Gly Thr Leu Val Thr Val Ser Ser
        115                 120


<210> SEQ ID NO 82
<211> LENGTH: 5
<212> TYPE: PRT
<213> ORGANISM: Artificial Sequence
<220> FEATURE:
<223> OTHER INFORMATION: Synthetic

<400> SEQUENCE: 82

Asp Tyr Ala Met His
1               5


<210> SEQ ID NO 83
<211> LENGTH: 17
<212> TYPE: PRT
<213> ORGANISM: Artificial Sequence
<220> FEATURE:
<223> OTHER INFORMATION: Synthetic

<400> SEQUENCE: 83

Gly Ile Ser Trp Arg Gly Asp Ile Gly Gly Tyr Val Lys Ser Val Lys
1               5                   10                  15

Gly


<210> SEQ ID NO 84
<211> LENGTH: 13
<212> TYPE: PRT
<213> ORGANISM: Artificial Sequence
<220> FEATURE:
<223> OTHER INFORMATION: Synthetic

<400> SEQUENCE: 84

Ser Tyr Gly Ser Gly Ser Phe Tyr Asn Ala Phe Asp Ser
1               5                   10


<210> SEQ ID NO 85
<211> LENGTH: 107
<212> TYPE: PRT
<213> ORGANISM: Artificial Sequence
<220> FEATURE:
<223> OTHER INFORMATION: Synthetic

<400> SEQUENCE: 85

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Glu Lys Leu Asp Arg Gly Thr Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Leu Glu Tyr Glu Ser Tyr Ile Arg
                85                  90                  95

Thr Phe Gly Gln Gly Thr Lys Val Glu Ile Lys
            100                 105
```

<210> SEQ ID NO 86
<211> LENGTH: 11
<212> TYPE: PRT
<213> ORGANISM: Artificial Sequence
<220> FEATURE:
<223> OTHER INFORMATION: Synthetic

<400> SEQUENCE: 86

Arg Ala Ser Gln Ser Ile Ser Ser Trp Leu Ala
1               5                   10

<210> SEQ ID NO 87
<211> LENGTH: 7
<212> TYPE: PRT
<213> ORGANISM: Artificial Sequence
<220> FEATURE:
<223> OTHER INFORMATION: Synthetic

<400> SEQUENCE: 87

Lys Ala Glu Lys Leu Asp Arg
1               5

<210> SEQ ID NO 88
<211> LENGTH: 9
<212> TYPE: PRT
<213> ORGANISM: Artificial Sequence
<220> FEATURE:
<223> OTHER INFORMATION: Synthetic

<400> SEQUENCE: 88

Leu Glu Tyr Glu Ser Tyr Ile Arg Thr
1               5

<210> SEQ ID NO 89
<211> LENGTH: 415
<212> TYPE: PRT
<213> ORGANISM: Human

<400> SEQUENCE: 89

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Gly
        35                  40                  45

Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
    130                 135                 140

Arg Ala Glu Ala Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn

```
                165                 170                 175

Asp Phe Thr Arg Val Val Gly Gly Glu Asp Ala Lys Pro Gly Gln Phe
            180                 185                 190

Pro Trp Gln Val Val Leu Asn Gly Lys Val Asp Ala Phe Cys Gly Gly
        195                 200                 205

Ser Ile Val Asn Glu Lys Trp Ile Val Thr Ala Ala His Cys Val Glu
    210                 215                 220

Thr Gly Val Lys Ile Thr Val Val Ala Gly Glu His Asn Ile Glu Glu
225                 230                 235                 240

Thr Glu His Thr Glu Gln Lys Arg Asn Val Ile Arg Ile Ile Pro His
                245                 250                 255

His Asn Tyr Asn Ala Ala Ile Asn Lys Tyr Asn His Asp Ile Ala Leu
            260                 265                 270

Leu Glu Leu Asp Glu Pro Leu Val Leu Asn Ser Tyr Val Thr Pro Ile
        275                 280                 285

Cys Ile Ala Asp Lys Glu Tyr Thr Asn Ile Phe Leu Lys Phe Gly Ser
    290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Arg Ser Thr Lys Phe Thr Ile Tyr Asn Asn Met Phe Cys Ala Gly
            340                 345                 350

Phe His Glu Gly Gly Arg Asp Ser Cys Gln Gly Asp Ser Gly Gly Pro
        355                 360                 365

His Val Thr Glu Val Glu Gly Thr Ser Phe Leu Thr Gly Ile Ile Ser
    370                 375                 380

Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr
                405                 410                 415


<210> SEQ ID NO 90
<211> LENGTH: 448
<212> TYPE: PRT
<213> ORGANISM: Human

<400> SEQUENCE: 90

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125
```

-continued

Pro Tyr Pro Cys Gly Lys Gln Thr Leu Glu Arg Arg Lys Arg Ser Val
    130                 135                 140

Ala Gln Ala Thr Ser Ser Ser Gly Glu Ala Pro Asp Ser Ile Thr Trp
145                 150                 155                 160

Lys Pro Tyr Asp Ala Ala Asp Leu Asp Pro Thr Glu Asn Pro Phe Asp
                165                 170                 175

Leu Leu Asp Phe Asn Gln Thr Gln Pro Glu Arg Gly Asp Asn Asn Leu
            180                 185                 190

Thr Arg Ile Val Gly Gly Gln Glu Cys Lys Asp Gly Glu Cys Pro Trp
        195                 200                 205

Gln Ala Leu Leu Ile Asn Glu Glu Asn Glu Gly Phe Cys Gly Gly Thr
    210                 215                 220

Ile Leu Ser Glu Phe Tyr Ile Leu Thr Ala Ala His Cys Leu Tyr Gln
225                 230                 235                 240

Ala Lys Arg Phe Lys Val Arg Val Gly Asp Arg Asn Thr Glu Gln Glu
                245                 250                 255

Glu Gly Gly Glu Ala Val His Glu Val Glu Val Val Ile Lys His Asn
            260                 265                 270

Arg Phe Thr Lys Glu Thr Tyr Asp Phe Asp Ile Ala Val Leu Arg Leu
        275                 280                 285

Lys Thr Pro Ile Thr Phe Arg Met Asn Val Ala Pro Ala Cys Leu Pro
    290                 295                 300

Glu Arg Asp Trp Ala Glu Ser Thr Leu Met Thr Gln Lys Thr Gly Ile
305                 310                 315                 320

Val Ser Gly Phe Gly Arg Thr His Glu Lys Gly Arg Gln Ser Thr Arg
                325                 330                 335

Leu Lys Met Leu Glu Val Pro Tyr Val Asp Arg Asn Ser Cys Lys Leu
            340                 345                 350

Ser Ser Ser Phe Ile Ile Thr Gln Asn Met Phe Cys Ala Gly Tyr Asp
        355                 360                 365

Thr Lys Gln Glu Asp Ala Cys Gln Gly Asp Ser Gly Gly Pro His Val
    370                 375                 380

Thr Arg Phe Lys Asp Thr Tyr Phe Val Thr Gly Ile Val Ser Trp Gly
385                 390                 395                 400

Glu Gly Cys Ala Arg Lys Gly Lys Tyr Gly Ile Tyr Thr Lys Val Thr
                405                 410                 415

Ala Phe Leu Lys Trp Ile Asp Arg Ser Met Lys Thr Arg Gly Leu Pro
            420                 425                 430

Lys Ala Lys Ser His Ala Pro Glu Val Ile Thr Ser Ser Pro Leu Lys
        435                 440                 445

<210> SEQ ID NO 91
<211> LENGTH: 326
<212> TYPE: PRT
<213> ORGANISM: Artificial Sequence
<220> FEATURE:
<223> OTHER INFORMATION: Synthetic

<400> SEQUENCE: 91

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

```
Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325


<210> SEQ ID NO 92
<211> LENGTH: 326
<212> TYPE: PRT
<213> ORGANISM: Artificial Sequence
<220> FEATURE:
<223> OTHER INFORMATION: Synthetic

<400> SEQUENCE: 92

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80
```

```
Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Leu Leu Tyr Ser
        275                 280                 285

Lys Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325
```

<210> SEQ ID NO 93
<211> LENGTH: 107
<212> TYPE: PRT
<213> ORGANISM: Artificial Sequence
<220> FEATURE:
<223> OTHER INFORMATION: Synthetic

<400> SEQUENCE: 93

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 94
<211> LENGTH: 329
<212> TYPE: PRT
<213> ORGANISM: Artificial Sequence
<220> FEATURE:
<223> OTHER INFORMATION: Synthetic

<400> SEQUENCE: 94

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Asp Glu
225 230 235 240

Leu Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Leu
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly
325

<210> SEQ ID NO 95
<211> LENGTH: 329
<212> TYPE: PRT
<213> ORGANISM: Artificial Sequence
<220> FEATURE:

-continued

<223> OTHER INFORMATION: Synthetic

<400> SEQUENCE: 95

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```